US012748106B2

(12) United States Patent
Diwu et al.

(10) Patent No.: US 12,748,106 B2
(45) Date of Patent: Sep. 29, 2026

(54) UV EXCITABLE POLYFLUORENE BASED CONJUGATES AND THEIR USE IN METHODS OF ANALYTE DETECTION

(71) Applicants: AAT Bioquest, Inc., Sunnyvale, CA (US); Affymetrix, Inc., Carlsbad, CA (US)

(72) Inventors: Zhenjun Diwu, Sunnyvale, CA (US); Haitao Guo, Sunnyvale, CA (US); Ruogu Peng, San Jose, CA (US); Travis Jennings, Poway, CA (US)

(73) Assignees: AAT Bioquest, Inc., Sunnyvale, CA (US); Affymetrix, Inc., Carlsbad, CA (US)

( * ) Notice: Subject to any disclaimer, the term of this patent is extended or adjusted under 35 U.S.C. 154(b) by 1077 days.

(21) Appl. No.: 17/793,173

(22) PCT Filed: Jan. 28, 2021

(86) PCT No.: PCT/US2021/015405
§ 371 (c)(1),
(2) Date: Jul. 15, 2022

(87) PCT Pub. No.: WO2021/154933
PCT Pub. Date: Aug. 5, 2021

(65) Prior Publication Data

US 2023/0131000 A1 Apr. 27, 2023

Related U.S. Application Data

(60) Provisional application No. 62/967,800, filed on Jan. 30, 2020.

(51) Int. Cl.

| | |
|---|---|
| ***G01N 33/533*** | (2006.01) |
| ***C07K 17/08*** | (2006.01) |
| ***C08G 73/06*** | (2006.01) |

(52) U.S. Cl.
CPC .......... *G01N 33/533* (2013.01); *C07K 17/08* (2013.01); *C08G 73/0688* (2013.01)

(58) Field of Classification Search
CPC .................. G01N 33/533; C07K 17/08; C08G 73/0688; C08G 61/121; C08G 2261/122; C08G 2261/1412; C08G 2261/1424; C08G 2261/143; C08G 2261/1432; C08G 2261/18; C08G 2261/3142; C08G 2261/344; C08G 2261/411; C08G 2261/522; C08G 2261/64; C08G 2261/76; C08G 2261/77; C08G 2261/80; C08G 2261/94; C09D 165/00; C09K 11/06
See application file for complete search history.

(56) References Cited

U.S. PATENT DOCUMENTS

2017/0275418 A1* 9/2017 Diwu .................... C08G 61/12

FOREIGN PATENT DOCUMENTS

| | | |
|---|---|---|
| WO | 2008/100344 A2 | 8/2008 |
| WO | 2017/172608 A1 | 10/2017 |

OTHER PUBLICATIONS

May 18, 2021—(WO) International Search Report & Written Opinion—App. No. PCT/US2021/015405.

Office Action for Chinese Application No. 202180016154.8, mailed Dec. 10, 2025.

* cited by examiner

*Primary Examiner* — Shafiqul Haq
(74) *Attorney, Agent, or Firm* — Klarquist Sparkman, LLP

(57) ABSTRACT

The invention provides for UV excitable polyfluorene based conjugates and their use in methods of analyte detection.

19 Claims, 16 Drawing Sheets

Synthetic pathway of fluorene based polymer bioconjugates
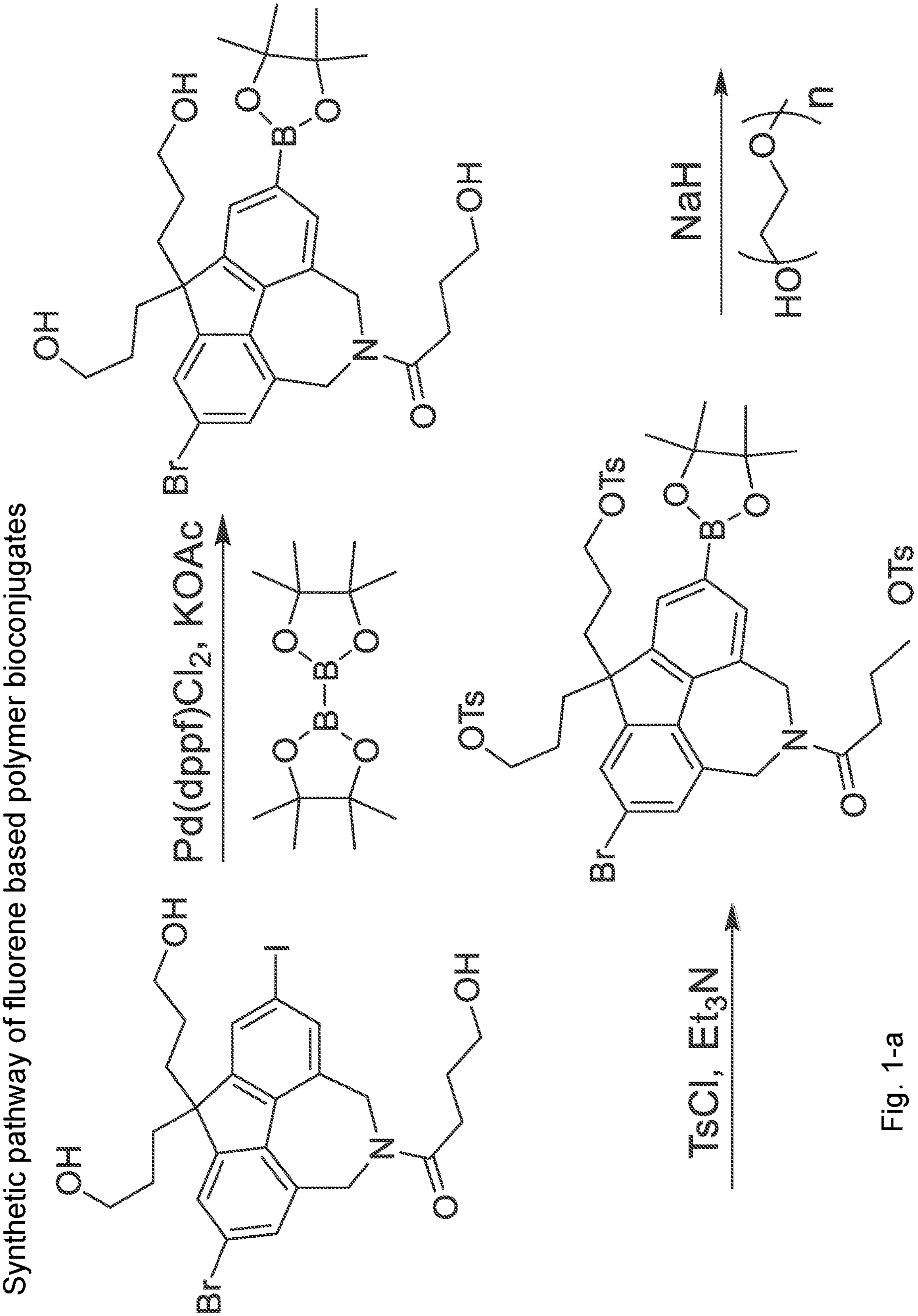
Fig. 1-a

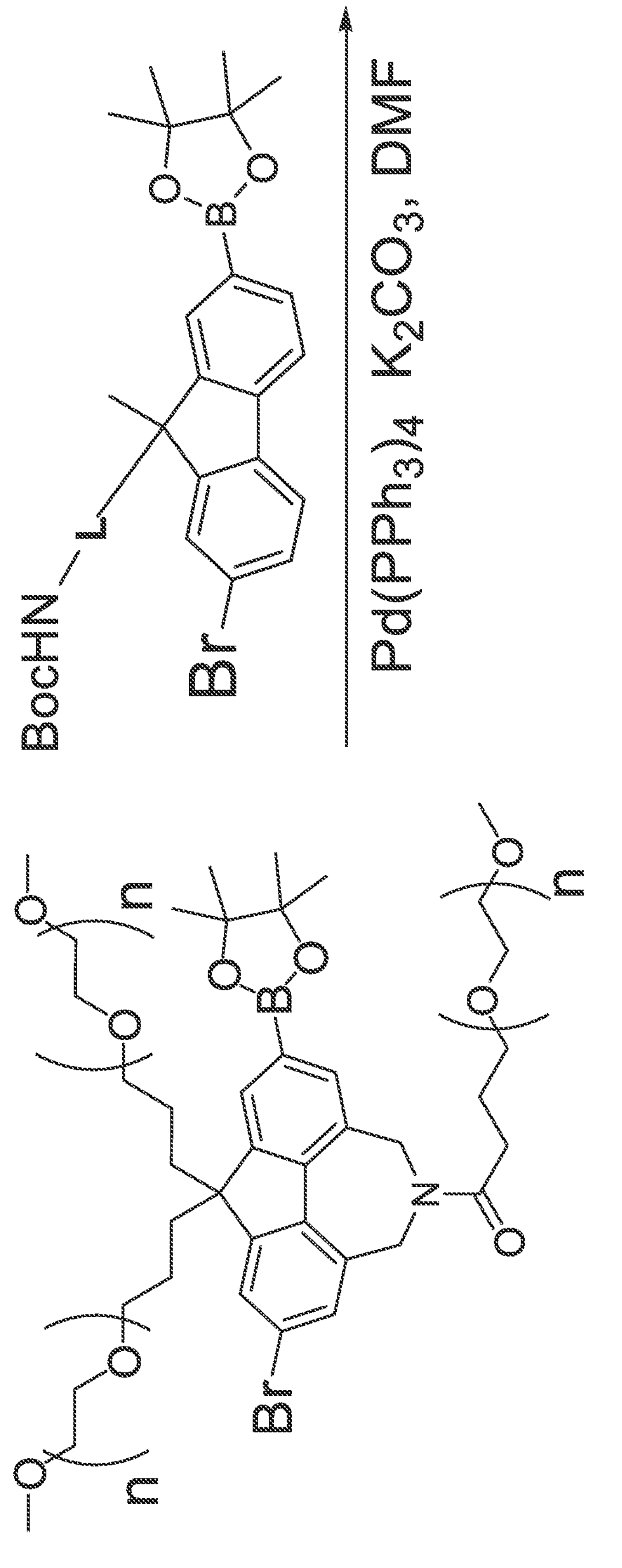
Fig. 1-b

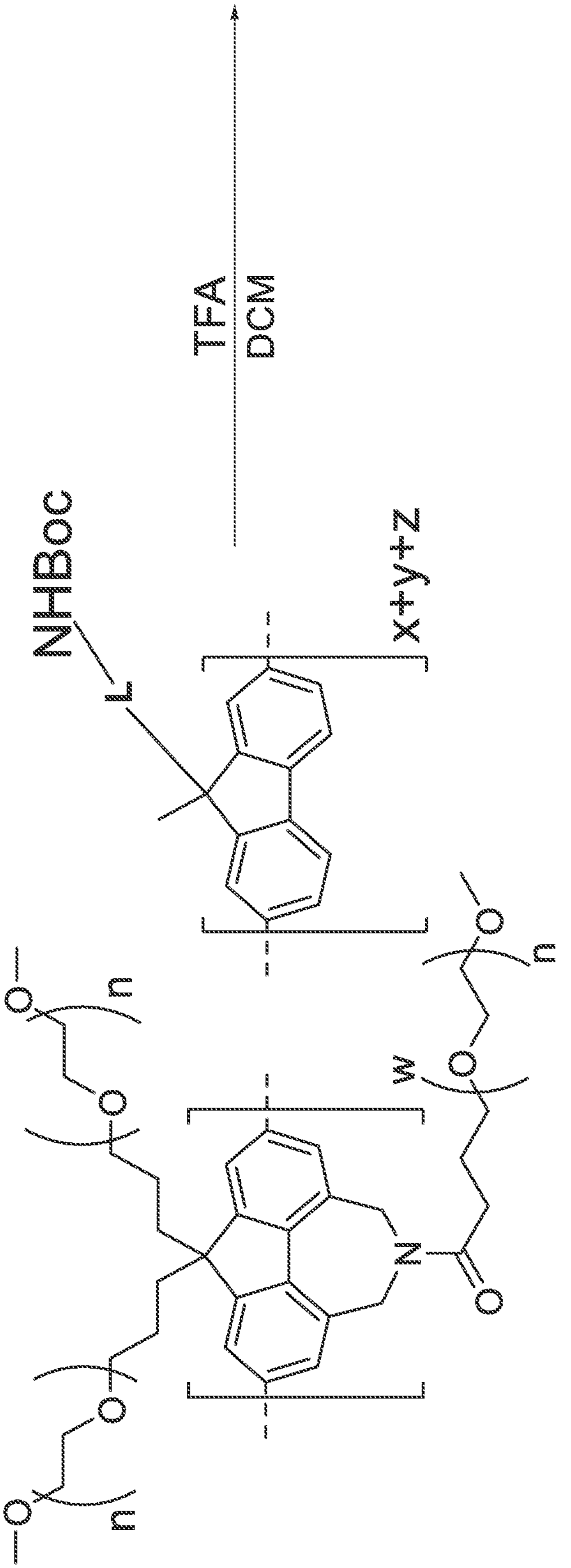
Fig. 1-c

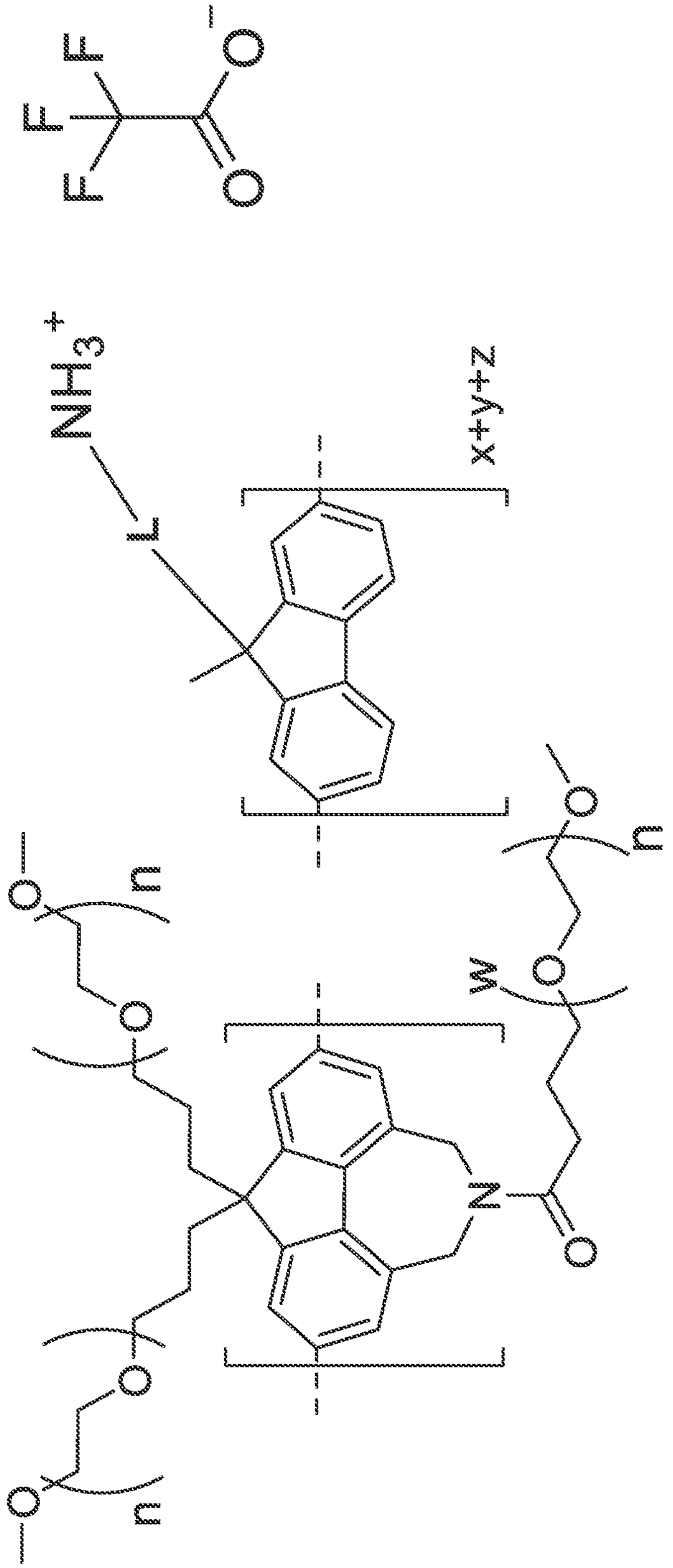
Fig. 1-d

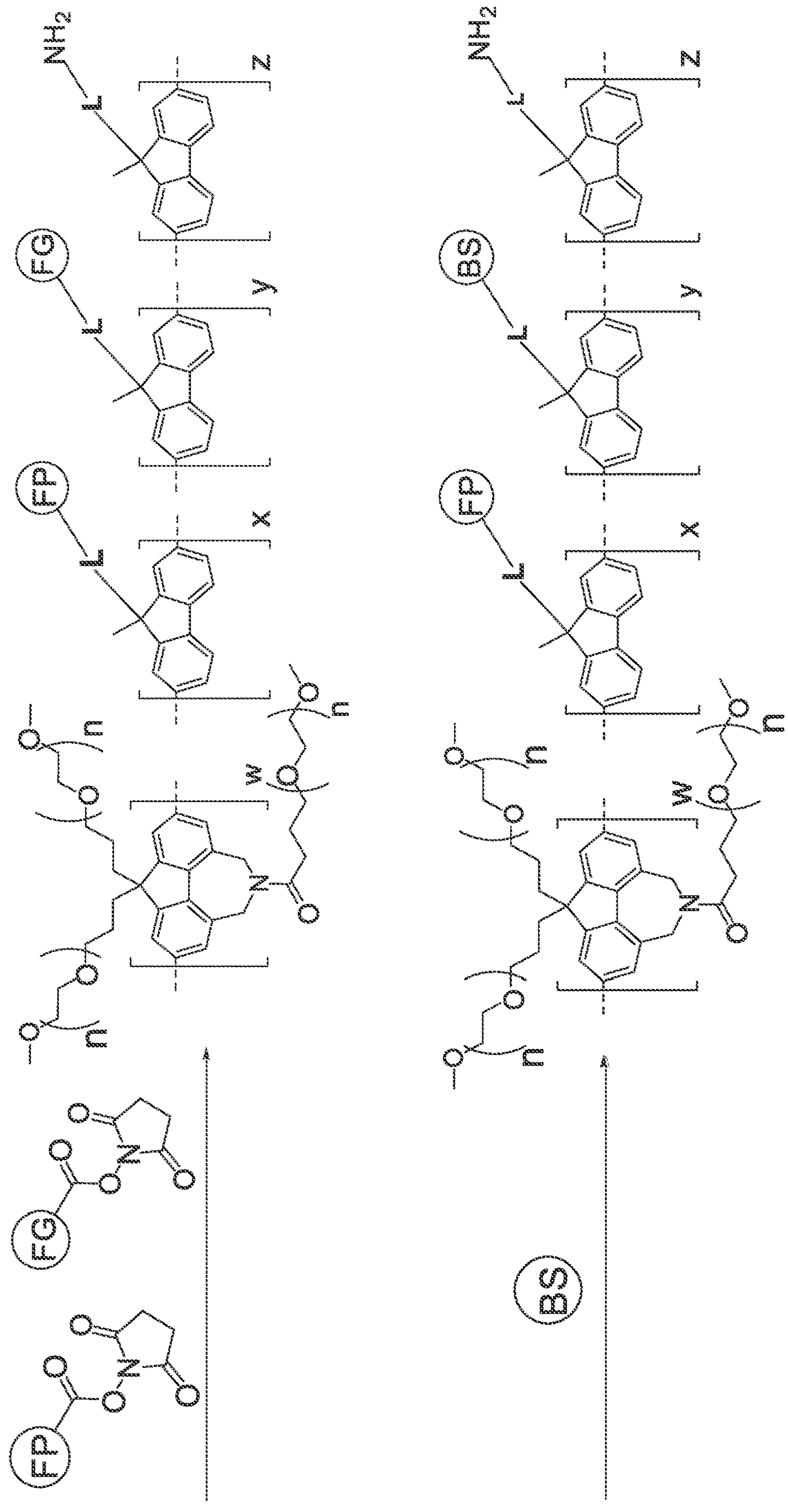
Fig. 1-e

UV EXCITABLE POLYFLUORENE BASED CONJUGATES AND THEIR USE IN METHODS OF ANALYTE DETECTION

RELATED APPLICATION DATA

This application is a National Stage Application under 35 U.S.C. 371 of co-pending PCT application PCT/US2021/015405 designating the United States and filed Jan. 28, 2021; which claims priority to U.S. Provisional Application No. 62/967,800 filed on Jan. 30, 2020, which are hereby incorporated herein by reference in their entireties for all purposes.

FIELD

The invention relates in general to fluorescent polymer conjugates and their methods of analyte detection.

BACKGROUND

Fluorescent probes are valuable reagents for the analysis and separation of molecules and cells and for the detection and quantification of other materials. A very small number of fluorescent molecules can be detected under optimal circumstances. Barak and Webb visualized fewer than 50 fluorescent lipid analogs associated with the LDL reception of cells using a SIT camera, J. CELL BIOL., 90, 595-604 (1981). Flow cytometry can be used to detect fewer than 10,000 fluorescein molecules associated with particles or certain cells (Muirhead, Horan and Poste, BIOTECHNOLOGY, 3, 337-356 (1985)). Some specific examples of the application of fluorescent probes are (1) identification and separation of subpopulations of cells in a mixture of cells by the techniques of fluorescence flow cytometry, fluorescence-activated cell sorting and fluorescence microscopy; (2) determination of the concentration of a substance that binds to a second species (e.g., antigen-antibody reactions) in the technique of fluorescence immunoassay; and (3) localization of substances in gels and other insoluble supports by the techniques of fluorescence staining. These techniques are described by Herzenberg, et al., "CELLULAR IMMUNOLOGY" 3rd ed., Chapter 22; Blackwell Scientific Publications (1978); and by Goldman, "FLUORESCENCE ANTIBODY METHODS", Academic Press, New York, (1968); and by Taylor, et al., APPLICATIONS OF FLUORESCENCE IN THE BIOMEDICAL SCIENCES, Alan Liss Inc., (1986).

When employing fluorescent polymers for the above purposes, there are many constraints on the choice of the fluorescent polymer. One constraint is the absorption and emission characteristics of the fluorescent polymer, since many ligands, receptors, and materials in the sample under test, e.g. blood, urine, cerebrospinal fluid, will fluoresce and interfere with an accurate determination of the fluorescence of the fluorescent label. This phenomenon is called autofluorescence or background fluorescence. Another consideration is the ability to conjugate the fluorescent polymer to ligands and receptors and other biological and non-biological materials and the effect of such conjugation on the fluorescent polymer. In many situations, conjugation to another molecule may result in a substantial change in the fluorescent characteristics of the fluorescent polymer and, in some cases, substantially destroy or reduce the quantum efficiency of the fluorescent polymer. It is also possible that conjugation with the fluorescent polymer will inactivate the function of the molecule that is labeled. A third consideration is the quantum efficiency of the fluorescent polymers which should be high for sensitive detection. A fourth consideration is the light absorbing capability, or extinction coefficient, of the fluorescent polymers, which should also be as large as possible. Also of concern is whether the fluorescent molecules will interact with each other when in close proximity, resulting in self-quenching. An additional concern is whether there is non-specific binding of the fluorescent polymers to other compounds or container walls, either by themselves or in conjunction with the compound to which the fluorescent polymer is conjugated.

The applicability and value of the methods indicated above are closely tied to the availability of suitable fluorescent compounds. In particular, there is a need for fluorescent substances that have strong absorption in the ultraviolet range (e.g., 355 nm), and emit fluorescence with a large Stokes shift, since excitation of these fluorophores produces less autofluorescence and also multiple chromophores fluorescing at different wavelengths can be analyzed simultaneously if the full visible and near infrared regions of the spectrum can be utilized. In recent years, violet lasers (405 nm) have been increasingly installed in commercial fluorescence instruments since it gives a much larger emission wavelength window than other lasers (e.g., argon laser at 488 nm and He—Ne laser at 633 nm) and ultraviolet lasers are also starting to be introduced. Phycobiliproteins have made an important contribution because of their high extinction coefficient and high quantum yield. These fluorophore-containing proteins can be covalently linked to many proteins and are used in fluorescence antibody assays in microscopy and flow cytometry. However, the phycobiliproteins have a few disadvantages that limit their biological applications, e.g., (1) the phycobiliproteins are relatively complex and tend to dissociate in highly diluted solutions; (2) they are extremely unstable and fade quickly upon illumination; and (3) the phycobiliproteins have very weak absorption from ultraviolet excitation.

Brightly fluorescent polymers permit detection or location of the attached materials with great sensitivity. Certain polyfluorene polymers have demonstrated utility as labeling reagents for immunological applications, e.g. U.S. Pat. Nos. 8,158,444; 8,455,613; 8,354,239; 8,362,193; and 8,575,303 to Gaylord, et al.; also WO 2013/101902 to Chiu et al. The other biological applications of polyfluorene polymers have been well documented by Thomas I I I et al. (Chem. Rev. 2007, 107, 1339); Zhu et al (Chem. Rev. 2012, 112, 4687) and Zhu et al. (Chem. Soc. Rev., 2011, 40, 3509). Nevertheless, all the existing water-soluble polyfluorene polymers are based on unsubstituted fluorenes due to the commercial unavailability of the required key intermediates. No efforts have been devoted to explore the biological applications of substituted fluorene polymers. The unsubstituted polyfluorene polymers are known to share certain disadvantages, e.g. (1) the existing polyfluorene polymers have emission wavelength close the UV edge of visible wavelength (400-800 nm); (2) the existing polyfluorene polymers also have a very strong tendency to self-aggregate (i.e. stack), which can significantly reduce the fluorescence quantum yields, as described in the extensive review by Mishra, et al., CHEM. REV., 100, 1973 (2000); and (3) the existing polyfluorene polymers allow the free rotation/vibration of two benzene units around the middle single bond that significantly reduces the polymer linearity and planarity. This phenomenon is called 'loose belt effect' that is described in "MODERN MOLECULAR PHOTOCHEMISTRY", Chapters 5 and 6, University Science Books, Sausalito, CA, authored by Nicholas J. Turro (1991). There remains a need for fluorescent polymers with improved fluorescent characteristics that can be excited with ultraviolet light.

SUMMARY

The present invention addresses this need and is based on the discovery that the so-called 'loose belt effect' can be eliminated by the crosslinking of the two benzene rings. It has been surprisingly found that rigid fluorene-based polymers unexpectedly yielded the desired biological properties. These polymer conjugates have (1) high fluorescence quantum yield; (2) red-shifted emission; (3) high water solubility; (4) high linearity; (5) high planarity; (6) high fluorescence resonance energy transfer (FRET) efficiency when a second dye coupled to the polymer; and (7) high photostability.

The core fluorene structure is shown below.

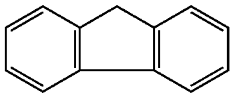

Fluorene

The rigid and bridged fluorene structure is shown below.

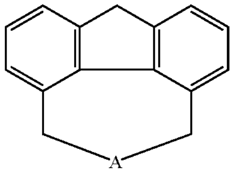

Rigid and Bridged Fluorene (A=N—, P—, O═P—, O═P—O—, —C—, —Si—, —S—, O═S—, O═S(O)—)

The disclosure provides a polymer comprising monomer units of formula A

A

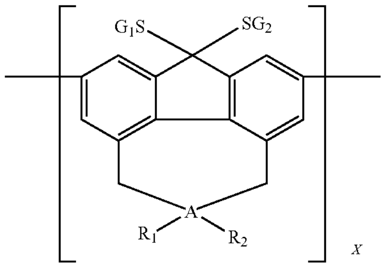

wherein X is the number of monomer units of formula A in the polymer wherein the monomer units of formula A are consecutive or nonconsecutive and wherein X is from 10 to 200, and one or more monomer units of formula B

B

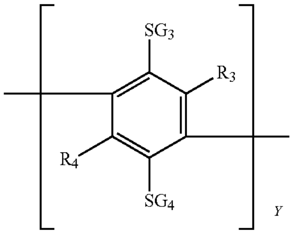

wherein Y is the number of monomer units of formula B in the polymer wherein the monomer units of formula B are consecutive or nonconsecutive and wherein Y is from 0 to 100, and, optionally one or more monomer units of formula C

C

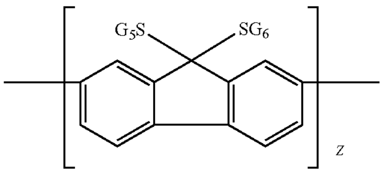

wherein Z is the number of monomer units of formula C in the polymer wherein the monomer units of formula C are consecutive or nonconsecutive and wherein Z is from 0 to 100, wherein A is O, S, N, or C;

wherein $SG_1$, $SG_2$, $SG_5$, $SG_6$, $R_1$ and $R_2$ independently is a hydrogen, an alkyl, an amino, a sulfo, a polyethylene glycol (PEG), a water solubilizing group, an acceptor, a linker (L), and/or a biological substrate conjugated via a linker (L-BS);

wherein $SG_3$, SG4, $R_3$ and $R_4$ independently is a hydrogen, a halogen, an amino, a PEG, a linker (L), and/or a biological substrate conjugated via a linker (L-BS);

wherein the polymer ends independently are a hydrogen, an alkyl, a halogen, a boronyl, an aryl, a heteroaryl group or a L-BS;

wherein the ratio of X to Y+Z is 0.3-1.0, and wherein the sum of X+Y+Z is 15 to 50.

In exemplary embodiments, fluoreno oxepine, fluoreno azepine, fluorenocycloheptane refers to O, N and C substitutions accordingly at the "A" substituent position in the ring for monomer units of formula A.

In one embodiment, when Y is present in the polymer in at least 40%, the UV excitation of the polymer is close to 350 nm.

In some embodiments, the monomer units of formula A, B and C are directly connected to one another.

In other embodiments, the acceptor comprises a fluorophore or a fluorescent dye and the ratio of the acceptor to polymer is 0.01-0.2.

In still other embodiments, the linker comprises an alkyl, a PEG, a carboxamide, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamides, a sulfonate ester, a 1,2,3-triazole, a pyradazine, a thiazolidine, a 2-diphenylphosphonyl-benzoamide, an isoxazole or a succinimide group.

In certain embodiments, (i) $SG_1$, $SG_2$, $SG_5$ and $SG_6$ independently represent a PEG, an alkyl, a carboxyalkyl, a sulfonylalkyl, a phosphonylalkyl, an aminoalkyl or L-BS; and/or (ii) $SG_3$, $SG_4$, $R_3$ and $R_4$ independently represent a hydrogen, a halogen, a PEG, or a linker (L), and/or (iii) L is an alkyl chain or a PEG chain; and/or (iv) BS is an antibody, a peptide, a protein, an oligonucleotide, a nucleic acid or a carbohydrate; and/or (v) a hydrogen, an alkyl, a halogen, a boronyl, an aryl, a heteroaryl group or a L-BS; and/or (vi) X, Y and Z are each an integer independently selected from 0 to 200, with ratio of X/Y+Z>0.4 and sum of X+Y+Z is 20 to 200.

In certain other embodiments, $SG_1$, $SG_2$, $SG_5$ and $SG_6$ are independently PEG3 to PEG30. In still other embodiments, $SG_1$-$SG_6$ and $R_1$-$R_4$ independently represent a hydrogen, a carboxyaryl, or a L-BS.

In certain embodiments, the monomer units of formula B comprises

B

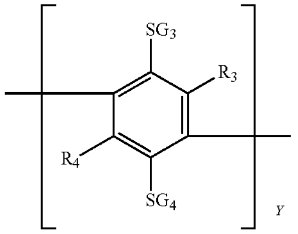

wherein Y is the number of monomer units of formula B in the polymer wherein the monomer units of formula B are consecutive or nonconsecutive and wherein Y is from 0 to 100; and wherein $SG_3$, $SG_4$, $R_3$ and $R_4$ independently is an alkyl, fluoro, hydrogen, a polyethylene glycol (PEG), or an acceptor.

In certain other embodiments, the A is C; and wherein $R_1$ and $R_2$ each is a polyethylene glycol (PEG).

In still other embodiments, the A is N; and wherein $R_1$ is non-existent and $R_2$ is

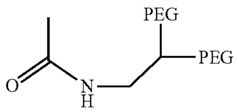

or

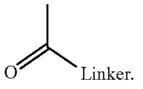

In some embodiments, the acceptor further comprises a fluorescein, a rhodamine, a rhodol, a cyanine, a BODIPY, a squaraine, a coumarin, a perylenediimide, a diketopyrrolopyrrole, a porphyrin or a phthalocyanine.

In certain embodiments, formula A, B and C comprise

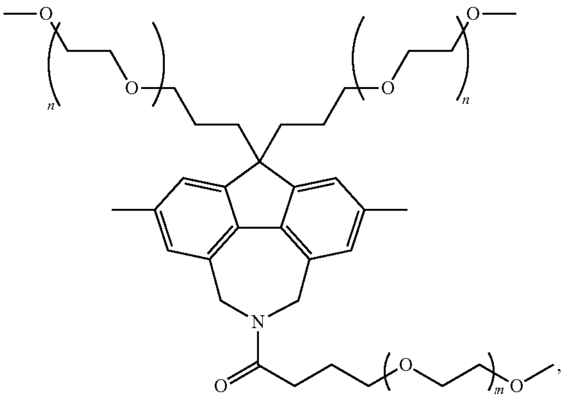

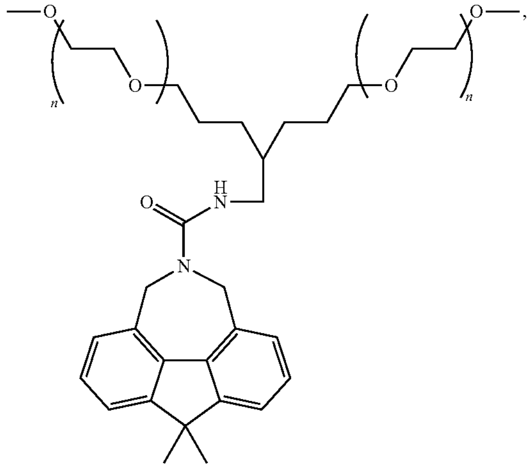

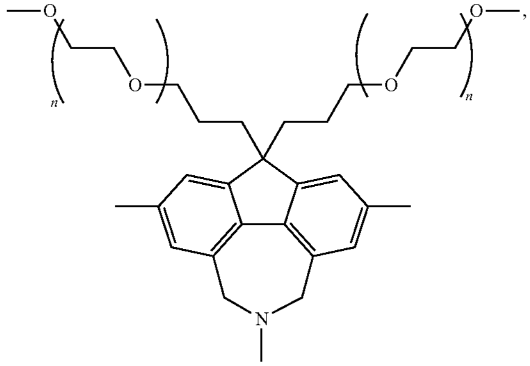

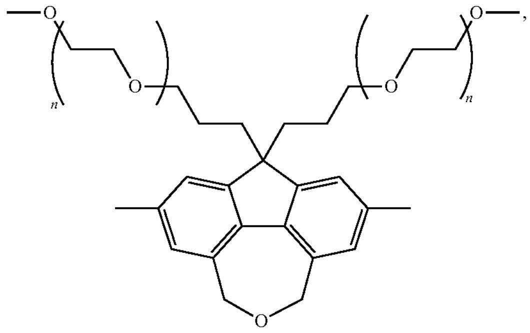

-continued
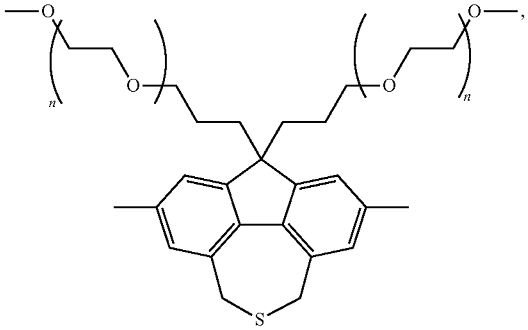
,
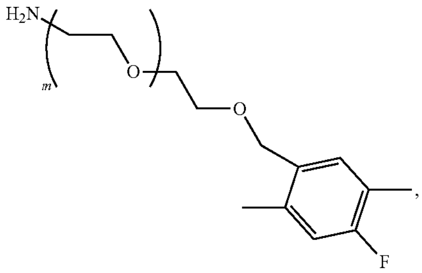
,
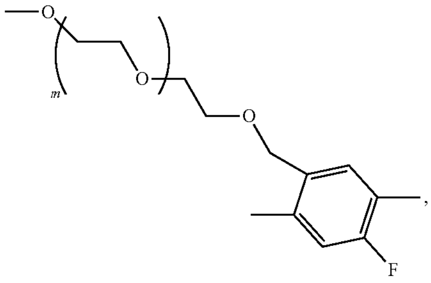
,
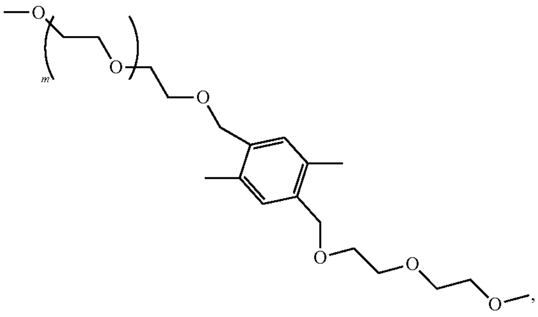
, or
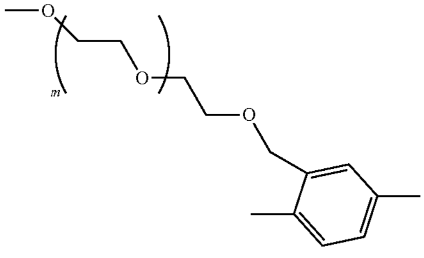
wherein m and n are from 5 to 20.
In some embodiments, the acceptor comprises:
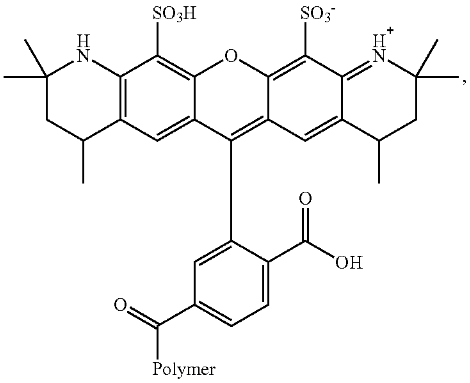
,
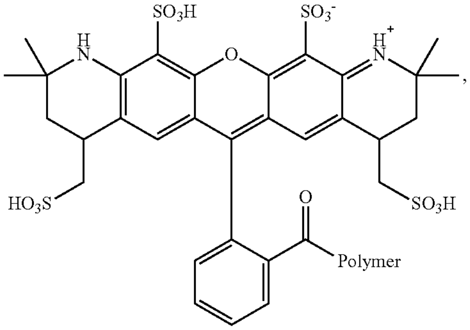
,
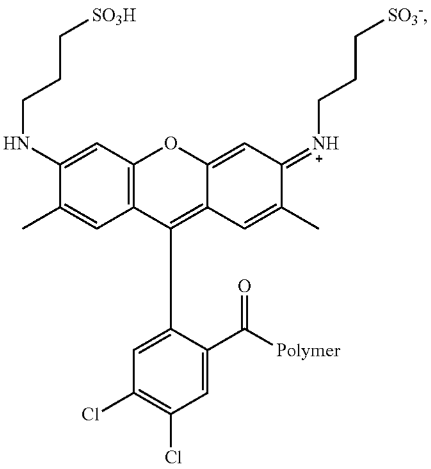
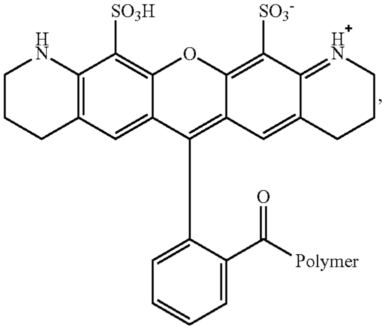
, -continued
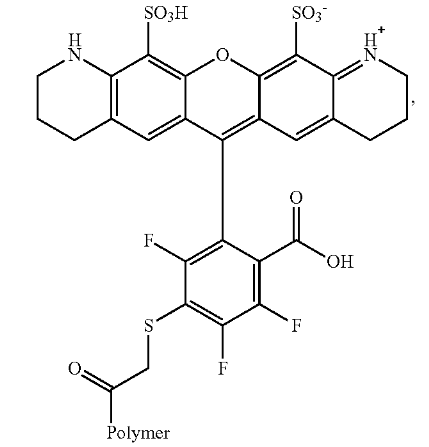
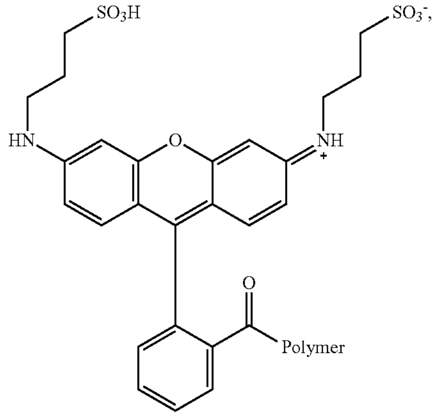
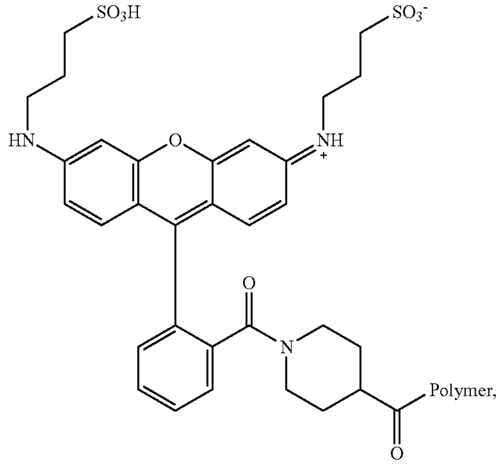
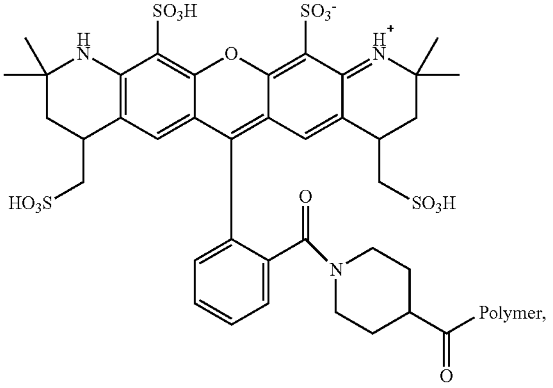
-continued
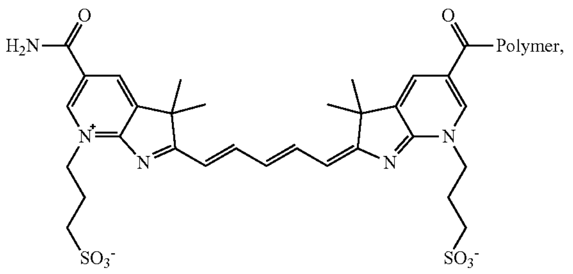
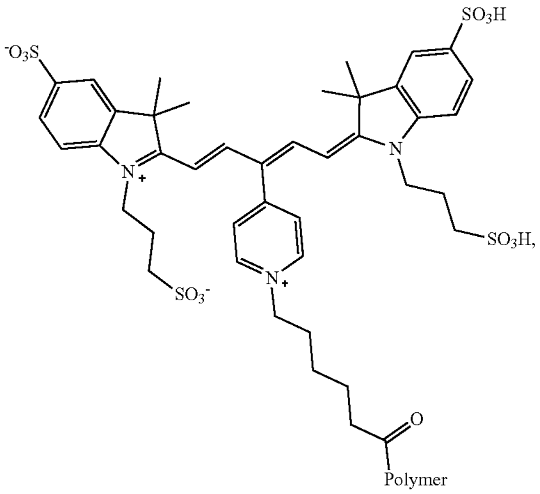
or
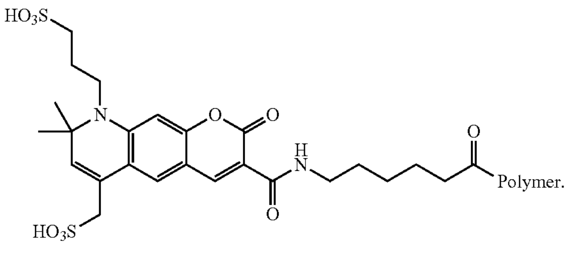

The present disclosure provides a polymer conjugate of Formula I.

Formula I

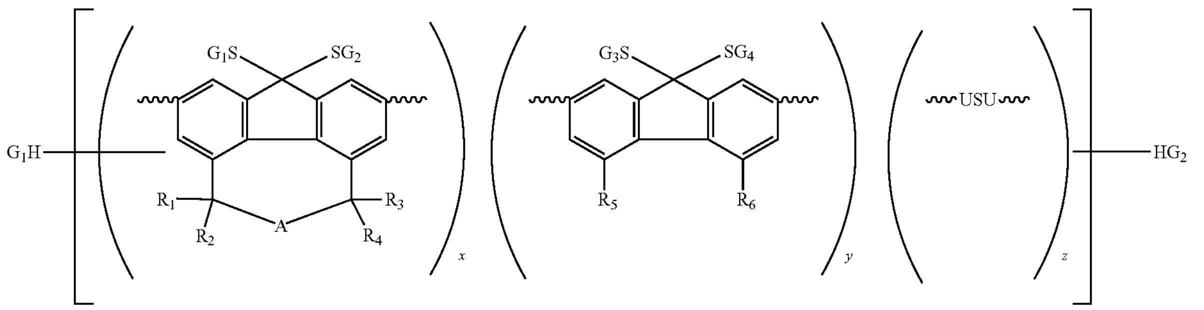

wherein the polymer conjugate comprises three monomer units shown within the parenthesis marked by x, y and z above, wherein the wiggly lines represent the connection point of the monomers, wherein USU represents an unsaturated unit, a double bond, a triple bond, an aryl, or a heteroaryl, wherein SG represents a water soluble group, wherein HG represents a head group, wherein the monomer units are randomly distributed along the polymer main chain; wherein A=N—$R_{10}$, P—$R_{11}$, O═P—$R_{11}$, O═P—$OR_{11}$, $R_{11}$—C—$R_{12}$, $R_{11}$—Si—$R_{12}$, $R_{11}$—S—$R_{11}$, O═S—$R_{11}$, O═S(O)—$R_{11}$; USU is an unsaturated unit, a double bond, a triple bond, an aryl, or a heteroaryl; $R_1$ to $R_{12}$ independently represent hydrogen, an alkyl, a polyethylene glycol (PEG), an aryl, a heteroaryl group, or a linked biological substrate (L-BS) wherein linker (L) is an alkyl or a PEG; wherein $SG_1$ to $SG_4$ independently represent an alkyl, a water soluble group or a L-BS; wherein HG1 and HG2 independently represent a hydrogen, an aryl, a halogen or a boronyl, an aryl, a heteroaryl group, or a L-BS; and wherein x, y and z are integers from 0-100, provided that (1) the ratio of BS/polymer is 0.2-3, (2) the ratio of x/(y+z) is >1, and (3) the sum of x+y+z is >10.

In one embodiment, the disclosure provides the polymer conjugate of formula I, wherein R1 to R6 independently represent hydrogen, methyl, or ethyl; wherein SG1 to SG4 independently represent a PEG, an alkyl, a carboxyalkyl, a sulfonylalkyl, a phosphonylalkyl, an aminoalkyl or L-BS; wherein L is an alkyl chain or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; and wherein x, y and z are integer from 0-80, provided that (1) the ratio of BS/polymer is 1-2, (2) the ratio of x/(y+z) is >1, and (3) the sum of x+y+z is >20.

In another embodiment, the disclosure provides the polymer conjugate of formula I, wherein R1 to R6 are hydrogen; wherein SG1 and SG2 are PEG; wherein SG3 to SG4 independently represent a PEG, an alkyl, a carboxyalkyl, a sulfonylalkyl, a phosphonylalkyl, an aminoalkyl or a L-BS; wherein L is an alkyl chain or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; and wherein x, y and z are integer from 0-80, provided that (1) the ratio of BS/polymer is 1-2, (2) the ratio of x/(y+z) is >1, and (3) the sum of x+y+z is >20.

In one embodiment, the disclosure provides the polymer conjugate of formula I, wherein SG3 to SG4 independently represent a PEG, an alkyl, a carboxyalkyl, or a L-BS.

In another embodiment, the disclosure provides the polymer conjugate of formula I, wherein SG3 to SG4 independently represent a PEG, an alkyl, an aminoalkyl or a L-BS.

In one embodiment, the disclosure provides the polymer conjugate of formula I, wherein SG1 and SG2 are independently PEG6 to PEG18.

In another embodiment, the disclosure provides the polymer conjugate of formula I, wherein the ratio of BS/polymer is 1; and wherein the sum of x+y+z is 30-80.

In one embodiment, the disclosure provides the polymer conjugate of formula I, wherein SG3 to SG4 independently represent a PEG, a methyl, a carboxyalkyl or a L-BS.

In another embodiment, the disclosure provides the polymer conjugate of formula I, wherein SG3 to SG4 independently represent a PEG, a methyl, an aminoalkyl or a L-BS.

In one embodiment, the disclosure provides the polymer conjugate of formula I, wherein R1 to R6 are hydrogen; wherein SG1 to SG4 independently represent a PEG, an alkyl, a carboxyalkyl, a sulfonylalkyl, a phosphonylalkyl, or an aminoalkyl; wherein HG1 and HG2 independently represent a hydrogen, an aryl, a halogen, a boronyl or or a L-BS; wherein L is an alkyl chain or a PEG chain; wherein BS is an antibody, a peptide, a protein, an oligonucleotide, a nucleic acid or a carbohydrate; and wherein x, y and z are integer from 0-80, provided that (1) the ratio of BS/polymer is 1-2, (2) the ratio of x/(y+z) is >1, and (3) the sum of x+y+z is >20.

In another embodiment, the disclosure provides the polymer conjugate of formula I, wherein the ratio of BS/polymer is 1; and wherein the sum of x+y+z is 30-80.

In one embodiment, the disclosure provides the polymer conjugate of formula I, wherein HG1 and HG2 independently represent a hydrogen, a carboxyaryl, or a L-BS.

In another embodiment, the disclosure provides the polymer conjugate of formula I, wherein HG1 and HG2 independently represent a halogen, a boronyl, a carboxyaryl, or a L-BS.

The present disclosure provides a polymer conjugate of Formula II.

Formula II

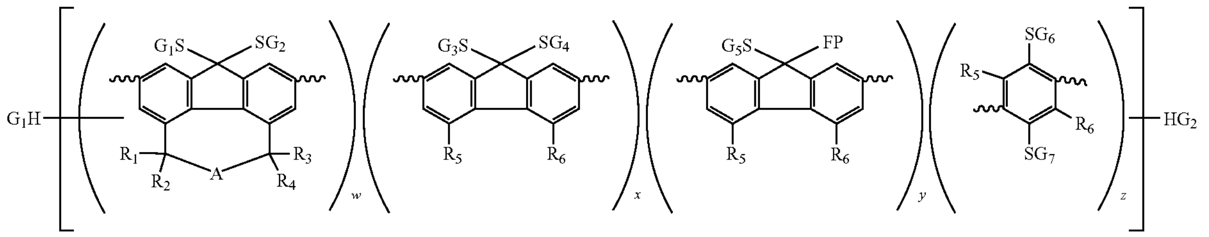

wherein the polymer conjugate comprises four monomer units shown within the parenthesis marked by w, x, y and z above, wherein the wiggly lines represent the connection point of the monomers, wherein SG represents a water soluble group, wherein HG represents a head group, wherein the monomer units that randomly distributed along the polymer main chain; wherein fluorophore (FP) is a fluorescent dye that has absorption maximum longer than 370 nm, and emission maximum longer than 400 nm with fluorescence quantum yield larger than 5%; wherein A=N—$R_{10}$, P—$R_{11}$, O═P—$R_{11}$, O═P—$OR_{11}$, $R_{11}$—C—$R_{12}$, $R_{11}$—Si—$R_{12}$, $R_{11}$—S—$R_{11}$, O═S—$R_{11}$, O═S(O)—$R_{11}$; R1 to R12 independently represent hydrogen, an alkyl, a PEG, an aryl, a heteroaryl group, or a L-BS; wherein L is an alkyl, a PEG or a FP; wherein SG1 to SG7 independently represent an alkyl, a water soluble group or a L-BS; wherein HG1 and HG2 independently represent an hydrogen, a halogen, a boronyl, an alkyl, an aryl, a heteroaryl group, or a L-BS; wherein w, x and z are integers from 0-100; and wherein y is an integer from 1 to 20, provided that (1) the ratio of BS/polymer is 0.2-3, (2) the ratio of w/(x+y+z) is >1, and (3) the sum of w+x+y+z is >10.

In one embodiment, the disclosure provides the polymer conjugate of formula II, wherein FP is a fluorescein, a rhodamine, a rhodol, a cyanine, a BODIPY, a squaraine, a coumarin, a perylenediimide, a diketopyrrolopyrrole, a porphyrin or a phthalocyanine; wherein R1 to R6 independently represent hydrogen, methyl, or ethyl; wherein SG1 to SG7 independently represent a PEG, an alkyl, a carboxyalkyl, a sulfonylalkyl, a phosphonylalkyl, an aminoalkyl or a L-BS; wherein L is an alkyl chain, a FP or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; wherein w, x and z are integers from 0-80; and wherein y is an integer from 1 to 10, provided that (1) the ratio of BS/polymer is 1-2, (2) the ratio of w/(x+y+z) is >1, and (3) the sum of w+x+y+z is >20.

In another embodiment, the disclosure provides the polymer conjugate of formula II, wherein R1 to R6 are hydrogen.

In one embodiment, the disclosure provides the polymer conjugate of formula II, wherein the ratio of BS/polymer is 1; wherein the sum of w+x+y+z is 30-80.

In another embodiment, the disclosure provides the polymer conjugate of formula II, wherein FP is a fluorescein, a rhodamine, a cyanine, a BODIPY, a squaraine, a perylenediimide, or a phthalocyanine.

In one embodiment, the disclosure provides the polymer conjugate of formula II, wherein FP is a rhodamine.

In another embodiment, the disclosure provides the polymer conjugate of formula II, wherein FP is a cyanine.

In one embodiment, the disclosure provides the polymer conjugate of formula II, wherein FP is a fluorescein, a rhodamine, a rhodol, a cyanine, a BODIPY, a squaraine, a coumarin, a perylenediimide, a diketopyrrolopyrrole, a porphyrin or a phthalocyanine; wherein R1 to R6 are hydrogen; wherein SG1 to SG7 independently represent a PEG, an alkyl, a carboxyalkyl, a sulfonylalkyl, a phosphonylalkyl, or an aminoalkyl; wherein HG1 and HG2 independently represent a hydrogen, an aryl, a halogen, a boronyl or a L-BS; wherein L is an alkyl chain, a FP or a PEG chain; wherein BS is an antibody, a peptide, a protein, an oligonucleotide, a nucleic acid or a carbohydrate; wherein w, x and z are integers from 0-80; and wherein y is an integer from 1 to 10, provided that (1) the ratio of BS/polymer is 1-2, (2) the ratio of w/(x+y+z) is >1, and (3) the sum of w+x+y+z is >20.

In another embodiment, the disclosure provides the polymer conjugate of formula II, wherein the ratio of BS/polymer is 1; and wherein the sum of x+y+z is 30-80.

In one embodiment, the disclosure provides the polymer conjugate of formula II, wherein HG1 and HG2 independently represent a hydrogen, a carboxyaryl, or a L-BS.

In another embodiment, the disclosure provides the polymer conjugate of formula II, wherein HG1 and HG2 independently represent a halogen, a boronyl, a carboxyaryl, or a L-BS.

The present disclosure provides a polymer conjugate of Formula III:

lp;4p

Formula III

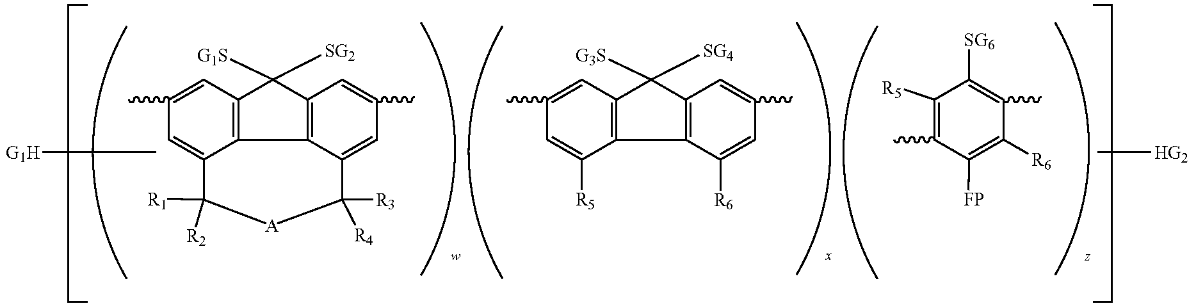

wherein the polymer conjugate comprises three monomer units shown within the parenthesis marked by w, x, and z above, wherein the wiggly lines represent the connection point of the monomers, wherein SG represents a water soluble group, wherein HG represents a head group, wherein the monomer units are randomly distributed along the polymer main chain; wherein fluorophore (FP) is a fluorescent dye that has absorption maximum longer than 370 nm, and emission maximum longer than 400 nm with fluorescence quantum yield larger than 5%; wherein A=N—$R_{10}$, P—$R_{11}$, O═P—$R_{11}$, O═P—$OR_{11}$, $R_{11}$—C—$R_{12}$, $R_{11}$—Si—$R_{12}$, $R_{11}$—S—$R_{11}$, O═S—$R_{11}$, O═S(O)—$R_{11}$; R1 to R12 independently represent hydrogen, an alkyl, a PEG, an aryl, a heteroaryl group, or a L-BS; wherein L is an alkyl, a PEG or a FP; wherein SG1 to SG6 independently represent an alkyl, a water soluble group or a L-BS; wherein HG1 and HG2 independently represent an hydrogen, a halogen, a boronyl, an alkyl, an aryl, a heteroaryl group, or a L-BS; wherein w, x and z are integers from 0-100; and wherein z is an integer from 1 to 20, provided that (1) the ratio of BS/polymer is 0.2-3, (2) the ratio of w/(x+z) is >1, and (3) the sum of w+x+z is >10.

In one embodiment, the disclosure provides the polymer conjugate of formula III, wherein FP is a fluorescein, a rhodamine, a rhodol, a cyanine, a BODIPY, a squaraine, a coumarin, a perylenediimide, a diketopyrrolopyrrole, a porphyrin or a phthalocyanine; wherein R1 to R6 independently represent hydrogen, methyl, or ethyl; wherein SG1 to SG6 independently represent a PEG, an alkyl, a carboxyalkyl, a sulfonylalkyl, a phosphonylalkyl, an aminoalkyl or a L-BS; wherein L is an alkyl chain, a FP or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; wherein w, x and z are integers from 0-80; and wherein z is an integer from 1 to 10, provided that (1) the ratio of BS/polymer is 1-2, (2) the ratio of w/(x+z) is >1, and (3) the sum of w+x+z is >20.

In another embodiment, the disclosure provides the polymer conjugate of formula III, wherein R1 to R6 are hydrogen.

In one embodiment, the disclosure provides the polymer conjugate of formula III, wherein the ratio of BS/polymer is 1; wherein the sum of w+x+z is 30-80.

In another embodiment, the disclosure provides the polymer conjugate of formula III, wherein FP is a fluorescein, a rhodamine, a cyanine, a BODIPY, a squaraine, a perylenediimide, or a phthalocyanine.

In one embodiment, the disclosure provides the polymer conjugate of formula III, wherein FP is a rhodamine.

In another embodiment, the disclosure provides the polymer conjugate of formula III, wherein FP is a cyanine.

In one embodiment, the disclosure provides the polymer conjugate of formula III, wherein FP is a fluorescein, a rhodamine, a rhodol, a cyanine, a BODIPY, a squaraine, a coumarin, a perylenediimide, a diketopyrrolopyrrole, a porphyrin or a phthalocyanine; wherein R1 to R6 are hydrogen; wherein SG1 to SG6 independently represent a PEG, an alkyl, a carboxyalkyl, a sulfonylalkyl, a phosphonylalkyl, or an aminoalkyl; wherein HG1 and HG2 independently represent a hydrogen, an aryl, a halogen, a boronyl or a L-BS; wherein L is an alkyl chain, a FP or a PEG chain; wherein BS is an antibody, a peptide, a protein, an oligonucleotide, a nucleic acid or a carbohydrate; wherein w, x and z are integers from 0-80; and wherein z is an integer from 1 to 10, provided that (1) the ratio of BS/polymer is 1-2, (2) the ratio of w/(x+z) is >1, and (3) the sum of w+x+z is >20.

In another embodiment, the disclosure provides the polymer conjugate of formula II, wherein the ratio of BS/polymer is 1; and wherein the sum of x+z is 30-80.

In one embodiment, the disclosure provides the polymer conjugate of formula II, wherein HG1 and HG2 independently represent a hydrogen, a carboxyaryl, or a L-BS.

In another embodiment, the disclosure provides the polymer conjugate of formula II, wherein HG1 and HG2 independently represent a halogen, a boronyl, a carboxyaryl, or a L-BS.

The present disclosure provides a polymer conjugate of Formula IV:

Formula IV

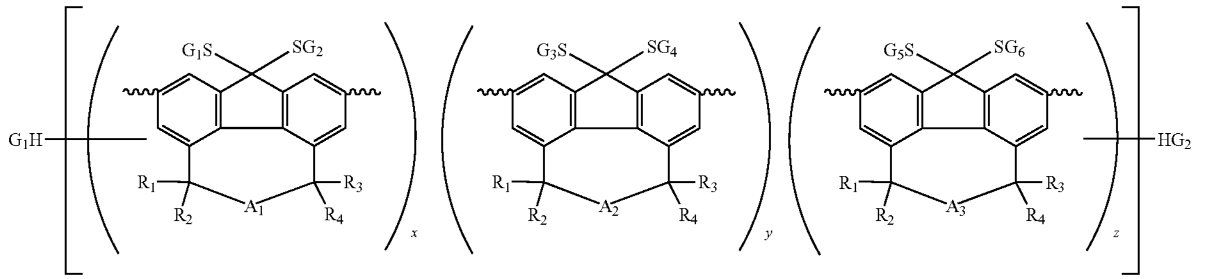

wherein the polymer conjugate comprises three monomer units shown within the parenthesis marked by x, y and z above, wherein the wiggly lines represent the connection point of the monomers, wherein SG represents a water soluble group, wherein HG represents a head group, wherein the polymer conjugate comprises three monomer units that are randomly distributed along the polymer main chain; wherein A1, A2 or A3=N—$R_{10}$, P—$R_{11}$, O═P—$R_{11}$, O═P—$OR_{11}$, $R_{11}$—C—$R_{12}$, $R_{11}$—Si—$R_{12}$, $R_{11}$—S—$R_{12}$, O═S—$R_{11}$, O═S(O)—$R_{11}$; R1 to R12 independently represent hydrogen, an alkyl, a polyethylene glycol (PEG), an aryl, a heteroaryl group, or a linked biological substrate (L-BS); wherein linker (L) is an alkyl or a PEG; wherein SG1 to SG6 independently represent an alkyl, a water soluble group or a L-BS; wherein HG1 and HG2 independently represent a hydrogen, an aryl, a halogen or a boronyl, an aryl, a heteroaryl group, or a L-BS; and wherein x, y and z are integers from 0-100, provided that (1) the ratio of BS/polymer is 0.2-3, and (2) the sum of x+y+z is >10.

In one embodiment, the disclosure provides the polymer conjugate of formula IV, wherein R1 to R4 independently represent hydrogen, methyl, or ethyl; wherein SG1 to SG6 independently represent a PEG, an alkyl, a carboxyalkyl, a sulfonylalkyl, a phosphonylalkyl, an aminoalkyl or L-BS; wherein L is an alkyl chain or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; and wherein x, y and z are integer from 0-80, provided that (1) the ratio of BS/polymer is 1-2, and (2) the sum of x+y+z is >20.

In another embodiment, the disclosure provides the polymer conjugate of formula IV, wherein R1 to R4 are hydrogen; wherein SG1 and SG2 are PEG; wherein SG3 to SG6 independently represent a PEG, an alkyl, a carboxyalkyl, a sulfonylalkyl, a phosphonylalkyl, an aminoalkyl or a L-BS; wherein L is an alkyl chain or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; and wherein x, y and z are integer from 0-80, provided that (1) the ratio of BS/polymer is 1-2, and (2) the sum of x+y+z is >20.

In one embodiment, the disclosure provides the polymer conjugate of formula IV, wherein SG3 to SG6 independently represent a PEG, an alkyl, a carboxyalkyl, or a L-BS.

In another embodiment, the disclosure provides the polymer conjugate of formula IV, wherein SG3 to SG6 independently represent a PEG, an alkyl, an aminoalkyl or a L-BS.

In one embodiment, the disclosure provides the polymer conjugate of formula IV, wherein the ratio of BS/polymer is 1; and wherein the sum of x+y+z is 30-80.

In another embodiment, the disclosure provides the polymer conjugate of formula IV, wherein SG3 to SG6 independently represent a PEG, a methyl, a carboxyalkyl or a L-BS.

In one embodiment, the disclosure provides the polymer conjugate of formula IV, wherein SG3 to SG6 independently represent a PEG, a methyl, an aminoalkyl or a L-BS.

In another embodiment, the disclosure provides the polymer conjugate of formula IV, wherein $R_1$ to $R_4$ are hydrogen; wherein SG1 to SG6 independently represent a PEG, an alkyl, a carboxyalkyl, a sulfonylalkyl, a phosphonylalkyl, or an aminoalkyl; wherein HG1 and HG2 independently represent a hydrogen, an aryl, a halogen, a boronyl or or a L-BS; wherein L is an alkyl chain or a PEG chain; wherein BS is an antibody, a peptide, a protein, an oligonucleotide, a nucleic acid or a carbohydrate; and wherein x, y and z are integer from 0-80, provided that (1) the ratio of BS/polymer is 1-2, (2) the ratio of x/(y+z) is >1, and (3) the sum of x+y+z is >20.

In one embodiment, the disclosure provides the polymer conjugate of formula IV, wherein the ratio of BS/polymer is 1; and wherein the sum of x+y+z is 30-80.

In another embodiment, the disclosure provides the polymer conjugate of formula IV, wherein HG1 and HG2 independently represent a hydrogen, a carboxyaryl, or a L-BS.

In another embodiment, the disclosure provides the polymer conjugate of formula IV, wherein HG1 and HG2 independently represent a halogen, a boronyl, a carboxyaryl, or a L-BS.

The present disclosure provides a polymer conjugate of Formula V:

Formula V

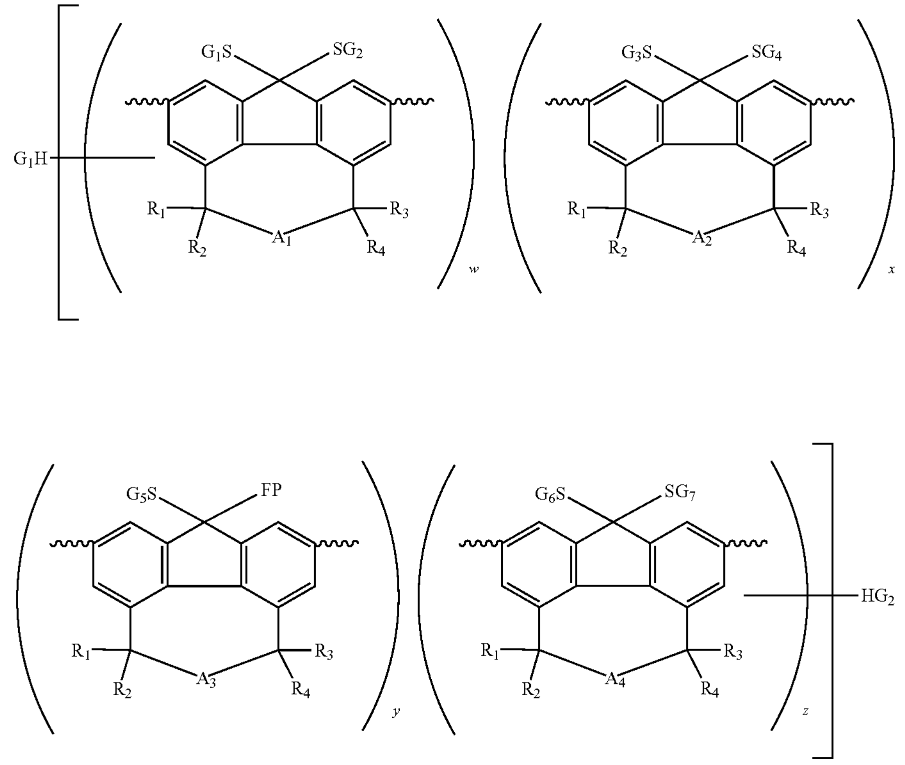

wherein the polymer conjugate comprises four monomer units shown within the parenthesis marked by w, x, y and z above, wherein the wiggly lines represent the connection point of the monomers, wherein SG represents a water soluble group, wherein HG represents a head group, wherein the monomer units are randomly distributed along the polymer main chain; wherein fluorophore (FP) is a fluorescent dye that has absorption maximum longer than 370 nm, and emission maximum longer than 400 nm with fluorescence quantum yield larger than 5%; wherein A1, A2, A3 or A4=N—$R_{10}$, P—$R_{11}$, O=P—$R_{11}$, O=P—$OR_{11}$, $R_{11}$—C—$R_{12}$, $R_{11}$—Si—$R_{12}$, $R_{11}$—S—$R_{12}$, O=S—$R_{11}$, O=S(O)—$R_{11}$; R1 to R12 independently represent hydrogen, an alkyl, a PEG, an aryl, a heteroaryl group, or a L-BS wherein L is an alkyl, a PEG or a FP; wherein SG1 to SG7 independently represent an alkyl, a water soluble group or a L-BS; wherein HG1 and HG2 independently represent an hydrogen, a halogen, a boronyl, an alkyl, an aryl, a heteroaryl group, or a L-BS; wherein w, x and z are integers from 0-100; and wherein y is an integer from 1 to 20, provided that (1) the ratio of BS/polymer is 0.2-3, and (2) the sum of w+x+y+z is >10.

In one embodiment, the disclosure provides the polymer conjugate of formula V, wherein FP is a fluorescein, a rhodamine, a rhodol, a cyanine, a BODIPY, a squaraine, a coumarin, a perylenediimide, a diketopyrrolopyrrole, a porphyrin or a phthalocyanine; wherein R1 to R4 independently represent hydrogen, methyl, or ethyl; wherein SG1 to SG7 independently represent a PEG, an alkyl, a carboxyalkyl, a sulfonylalkyl, a phosphonylalkyl, an aminoalkyl or a L-BS; wherein L is an alkyl chain, a FP or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; wherein w, x and z are integers from 0-80; and wherein y is an integer from 1 to 10, provided that (1) the ratio of BS/polymer is 1-2, and (2) the sum of w+x+y+z is >20.

In another embodiment, the disclosure provides the polymer conjugate of formula V, wherein R1 to R4 are hydrogen.

In one embodiment, the disclosure provides the polymer conjugate of formula V, wherein the ratio of BS/polymer is 1; and wherein the sum of w+x+y+z is 30-80.

In another embodiment, the disclosure provides the polymer conjugate of formula V, wherein FP is a fluorescein, a rhodamine, a cyanine, a BODIPY, a squaraine, a perylenediimide, or a phthalocyanine.

In one embodiment, the disclosure provides the polymer conjugate of formula V, wherein FP is a rhodamine.

In another embodiment, the disclosure provides the polymer conjugate of formula V, wherein FP is a cyanine.

In one embodiment, the disclosure provides the polymer conjugate of formula V, wherein FP is a fluorescein, a rhodamine, a rhodol, a cyanine, a BODIPY, a squaraine, a coumarin, a perylenediimide, a diketopyrrolopyrrole, a porphyrin or a phthalocyanine; wherein R1 to R4 are hydrogen; wherein SG1 to SG7 independently represent a PEG, an alkyl, a carboxyalkyl, a sulfonylalkyl, a phosphonylalkyl, or an aminoalkyl; wherein HG1 and HG2 independently represent a hydrogen, an aryl, a halogen, a boronyl or a L-BS; wherein L is an alkyl chain, a FP or a PEG chain; wherein BS is an antibody, a peptide, a protein, an oligonucleotide, a nucleic acid or a carbohydrate; wherein w, x and z are integers from 0-80; and wherein y is an integer from 1 to 10, provided that (1) the ratio of BS/polymer is 1-2, and (2) the sum of w+x+y+z is >20.

In another embodiment, the disclosure provides the polymer conjugate of formula V, wherein the ratio of BS/polymer is 1; and wherein the sum of w+x+y+z is 30-80.

In one embodiment, the disclosure provides the polymer conjugate of formula V, wherein HG1 and HG2 independently represent a hydrogen, a carboxyaryl, or a L-BS.

In another embodiment, the disclosure provides the polymer conjugate of formula V, wherein HG1 and HG2 independently represent a halogen, a boronyl, a carboxyaryl, or a L-BS.

The present disclosure further provides a method of detecting an analyte in a sample, comprising a) combining said sample with a detection reagent comprising a polymer conjugate having the structure of Formula I under conditions under which said detection reagent will bind said analyte; and
b) detecting the detection reagent bound analyte by fluorescence, wherein the polymer conjugate comprises three monomer units that are randomly distributed along the polymer main chain; wherein R1 to R6 independently represent hydrogen, an alkyl, a polyethylene glycol (PEG), an aryl, a heteroaryl group, or a linked biological substrate (L-BS); wherein linker (L) is an alkyl or a PEG; wherein SG1 to SG6 independently represent an alkyl, a water soluble group or a L-BS; wherein HG1 and HG2 independently represent a hydrogen, an aryl, a halogen or a boronyl, an aryl, a heteroaryl group, or a L-BS; and wherein x, y and z are integers from 0-100, provided that (1) the ratio of BS/polymer is 0.2-3, (2) the ratio of x/(y+z) is >1, and (3) the sum of x+y+z is >10.

The present disclosure provides a method of detecting an analyte in a sample, comprising a) combining said sample with a detection reagent comprising a polymer conjugate having the structure of Formula II under conditions under which said detection reagent will bind said analyte; and
b) detecting the detection reagent bound analyte by fluorescence, wherein the polymer conjugate comprises four monomer units that are randomly distributed along the polymer main chain; wherein fluorophore (FP) is a fluorescent dye that has absorption maximum longer than 370 nm, and emission maximum longer than 400 nm with fluorescence quantum yield larger than 5%; wherein R1 to R6 independently represent hydrogen, an alkyl, a PEG, an aryl, a heteroaryl group, or a L-BS; wherein L is an alkyl, a PEG or a FP; wherein SG1 to SG7 independently represent an alkyl, a water soluble group or a L-BS; wherein HG1 and HG2 independently represent an hydrogen, a halogen, a boronyl, an alkyl, an aryl, a heteroaryl group, or a L-BS; wherein w, x and z are integers from 0-100; and wherein y is an integer from 1 to 20, provided that (1) the ratio of BS/polymer is 0.2-3, (2) the ratio of w/(x+y+z) is >1, and (3) the sum of w+x+y+z is >10.

The present disclosure further provides a method of detecting an analyte in a sample, comprising a) combining said sample with a detection reagent comprising a polymer conjugate having the structure of Formula III under conditions under which said detection reagent will bind said analyte; and
b) detecting the detection reagent bound analyte by fluorescence, wherein the polymer conjugate comprises three monomer units that are randomly distributed along the polymer main chain; wherein R1 to R4 independently represent hydrogen, an alkyl, a polyethylene glycol (PEG), an aryl, a heteroaryl group, or a linked biological substrate (L-BS); wherein linker (L) is an alkyl or a PEG; wherein SG1 to SG6 independently represent an alkyl, a water soluble group or a L-BS; wherein HG1 and HG2 independently represent a hydrogen, an aryl, a halogen or a boronyl, an aryl, a heteroaryl group, or a L-BS; and wherein x, y and z are integers from 0-100, provided that (1) the ratio of BS/polymer is 0.2-3, and (2) the sum of x+y+z is >10.

The present disclosure provides a method of detecting an analyte in a sample, comprising a) combining said sample with a detection reagent comprising a polymer conjugate having the structure of Formula IV under conditions under which said detection reagent will bind said analyte; and
b) detecting the detection reagent bound analyte by fluorescence, wherein the polymer conjugate comprises four monomer units that are randomly distributed along the polymer main chain; wherein fluorophore (FP) is a fluorescent dye that has absorption maximum longer than 370 nm, and emission maximum longer than 400 nm with fluorescence quantum yield larger than 5%; wherein R1 to R4 independently represent hydrogen, an alkyl, a PEG, an aryl, a heteroaryl group, or a L-BS; wherein L is an alkyl, a PEG or a FP; wherein SG1 to SG7 independently represent an alkyl, a water soluble group or a L-BS; wherein HG1 and HG2 independently represent an hydrogen, a halogen, a boronyl, an alkyl, an aryl, a heteroaryl group, or a L-BS; wherein x, y and z are integers from 0-100; and wherein y is an integer from 1 to 20, provided that (1) the ratio of BS/polymer is 0.2-3, and (2) the sum of x+y+z is >10.

The present disclosure provides a method of detecting an analyte in a sample, comprising a) combining said sample with a detection reagent comprising a polymer conjugate having the structure of Formula V under conditions under which said detection reagent will bind said analyte; and
b) detecting the detection reagent bound analyte by fluorescence, wherein the polymer conjugate comprises four monomer units that are randomly distributed along the polymer main chain; wherein fluorophore (FP) is a fluorescent dye that has absorption maximum longer than 370 nm, and emission maximum longer than 400 nm with fluorescence quantum yield larger than 5%; wherein R1 to R4 independently represent hydrogen, an alkyl, a PEG, an aryl, a heteroaryl group, or a L-BS; wherein L is an alkyl, a PEG or a FP; wherein SG1 to SG7 independently represent an alkyl, a water soluble group or a L-BS; wherein HG1 and HG2 independently represent an hydrogen, a halogen, a boronyl, an alkyl, an aryl, a heteroaryl group, or a L-BS; wherein w, x and z are integers from 0-100; and wherein y is an integer from 1 to 20, provided that (1) the ratio of BS/polymer is 0.2-3, and (2) the sum of w+x+y+z is >10.

In one embodiment, the disclosure provides the polymer conjugate of formula I, II, III, IV or V, wherein BS is an antibody.

In another embodiment, the disclosure provides the polymer conjugate of formula I, II, III, IV or V, wherein BS is an anti-digoxigenin antibody.

In yet another embodiment, the disclosure provides the polymer conjugate of formula I, II, III, IV or V, wherein BS is a goat anti-mouse IgG antibody, goat anti-rabbit IgG antibody, goat anti-human IgG antibody, donkey anti-mouse IgG antibody, donkey anti-rabbit IgG antibody, donkey anti-human IgG antibody, chicken anti-mouse IgG antibody, chicken anti-rabbit IgG antibody, or chicken anti-human IgG antibody.

In one embodiment, the disclosure provides the polymer conjugate of formula I, II, III, IV or V, wherein BS is an avidin, streptavidin, neutravidin, or avidin.

In another embodiment, the disclosure provides the polymer conjugate of formula I, II, III, IV or V, wherein the analyte is a target protein expressed on a cell surface.

In another embodiment, the disclosure provides the polymer conjugate of formula I, II, III, IV or V, wherein the analyte is a target protein is an intracellular protein detected within the cell.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. These and other embodiments are disclosed or are obvious from and encompassed by, the following Detailed Description.

BRIEF DESCRIPTION OF THE DRAWINGS

The foregoing and other features and advantages of the present embodiments will be more fully understood from the following detailed description of illustrative embodiments taken in conjunction with the accompanying drawings in which:

FIG. 1. A typical synthesis of fluorene polymer bioconjugates. BS is a biological substrate (e.g, antibodies). w, x, y and z are the number of monomer units. FG is a functional group used for conjugation as listed in Table 2. FP is a fluorophore as listed in Table 1. L is a linker.

FIG. 3A). Absorption and emission spectra of the foundation polymer. FIG. 3B). Absorption and emission spectra of a tandem version of the same fluoreno oxepine foundation polymer, with energy transfer from the polymer to an acceptor dye emitting around 563 nm.

FIG. 4A). Absorption and emission spectra of the foundation polymer. FIG. 4B). Absorption and emission spectra of a tandem version of the same fluoreno oxepine foundation polymer, with energy transfer from the polymer to an acceptor dye emitting around 805 nm.

FIG. 5A). Absorption and emission spectra of the foundation polymer. FIG. 5B). Absorption and emission spectra of a tandem version of the same fluorenocycloheptane foundation polymer, with energy transfer from the polymer to an acceptor dye emitting around 563 nm.

FIG. 6A). Absorption and emission spectra of the foundation polymer.

FIG. 6B). Absorption and emission spectra of a tandem version of the same fluorenocycloheptane foundation polymer, with energy transfer from the polymer to an acceptor dye emitting around 805 nm.

FIG. 7A). Absorption and emission spectra of the foundation polymer. FIG. 7B). Absorption and emission spectra of a tandem version of the same fluoreno azepine foundation polymer, with energy transfer from the polymer to an acceptor dye emitting around 805 nm.

FIG. 8A). Absorption and emission spectra of the foundation polymer. FIG. 8B). Absorption and emission spectra of a tandem version of the same fluoreno azepine foundation polymer, with energy transfer from the polymer to an acceptor dye emitting around 805 nm.

FIG. 9A). The oxepine-based foundation polymer using Linker 1 was conjugated to anti-mouse CD4 (clone RM4-5) monoclonal antibody and used to stain mouse splenocytes that were analyzed by flow cytometry. The conjugated antibodies identified the CD3-positive, CD4-positive cells, as shown in the upper right quadrant. FIG. 9B). The fluoreno oxepine-based tandem polymer using Linker 1 was conjugated to anti-mouse CD4 (clone RM4-5) monoclonal antibody and used to stain mouse splenocytes that were analyzed by flow cytometry. The conjugated antibodies identified the CD3-positive, CD4-positive cells cells, as shown in the upper right quadrant. FIG. 9C). The fluoreno oxepine-based foundation polymer using Linker 2 was conjugated to anti-human CD25 (clone BC96) and used to stain stimulated normal human peripheral blood cells that were analyzed by flow cytometry. The conjugated antibodies identified the CD25-positive cells, as shown in the upper two quadrants. FIG. 9D). The oxepine-based tandem polymer using Linker 2 was conjugated to anti-human TNF alpha (clone MAb11) and used to intracellularly stain stimulated normal human peripheral blood cells that were analyzed by flow cytometry. The conjugated antibodies identified the TNF alpha-positive cells, as shown in the upper two quadrants.

FIG. 10A). The fluorenocycloheptane-based foundation polymer using Linker 1 was conjugated to anti-mouse CD4 (clone RM4-5) and used to stain mouse splenocytes that were analyzed by flow cytometry. The conjugated antibody identified the CD3-positive, CD4-positive cells, as shown in the upper right quadrant. FIG. 10B). The fluorenocycloheptane-based tandem polymer using Linker 1 was conjugated to anti-human CD25 (clone BC96) and used to stain stimulated normal human peripheral blood cells that were analyzed by flow cytometry. The conjugated antibody identified CD25-positive cells as shown in the upper two quadrants. FIG. 10C). The fluorenocycloheptane-based foundation polymer using Linker 2 was conjugated to anti-mouse CD4 (clone RM4-5) and used to stain mouse splenocytes that were analyzed by flow cytometry. The conjugated antibody identified the CD3-positive, CD4-positive cells, as shown in the upper right quadrant. FIG. 10D). The fluorenocycloheptane-based tandem polymer using Linker 2 was conjugated to anti-mouse CD4 (clone RM4-5) and used to stain mouse splenocytes that were analyzed by flow cytometry. The conjugated antibody identified the CD3-positive, CD4-positive cells, as shown in the upper right quadrant.

FIG. 11A). The fluoreno azepine-based foundation polymer using Linker 1 was conjugated to anti-mouse CD4 (clone RM4-5) and used to stain mouse splenocytes that were analyzed by flow cytometry. The conjugated antibody identified the CD3-positive, CD4-positive cells, as shown in the upper right quadrant. FIG. 11B). The fluoreno azepine-based tandem polymer using Linker 1 was conjugated to anti-human CD20 (clone 2H7) and used to stain normal human peripheral blood cells that were analyzed by flow cytometry. The conjugated antibody identified the CD3-negative, CD20-bright cells as shown in the top left quadrant of the data plot, as well as the CD3-positive, CD20-dim cells as shown in the upper right quadrant. FIG. 11C). The fluoreno azepine-based foundation polymer using Linker 2 was conjugated to anti-human TNF alpha (clone MAb11) and used to intracellularly stain stimulated normal human peripheral blood cells that were analyzed by flow cytometry. The conjugated antibody identified the TNF alpha-positive cells, as shown in the upper two quadrants. FIG. 11D). The fluoreno azepine-based tandem polymer using Linker 2 was conjugated to anti-human Ki-67 (clone 20Raj1) and used to intracellularly stain stimulated normal human peripheral blood cells that were analyzed by flow cytometry. The conjugated antibody identified the CD19-negative, Ki-67-positive cells, as shown in the upper left quadrant.

DETAILED DESCRIPTION

Figure 2A:
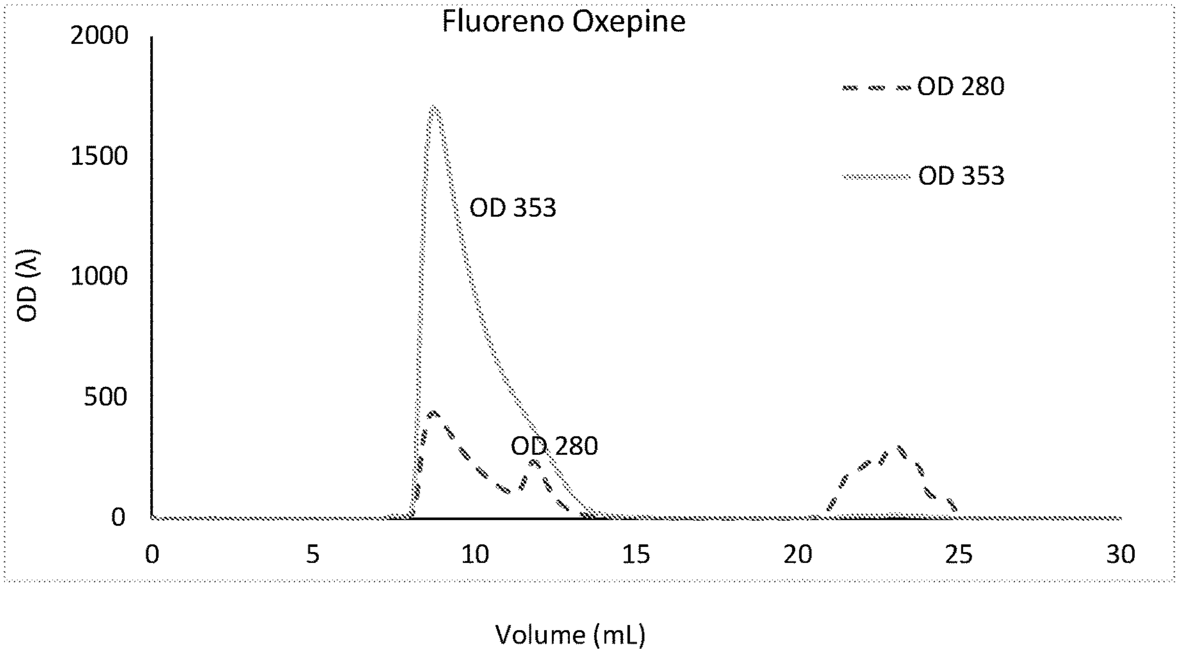
FIGS. 2A-2C. Size exclusion purification of antibody conjugates prepared using fluoreno oxepine (FIG. 2A), fluorenocycloheptane (FIG. 2B), and fluoreno azepine (FIG. 2C) based polymers. The raw conjugated reaction mixture was purified over Superdex 200 increase resin, and the purified conjugate elutes between 7-10 milliliters volume, and is collected separately. The unconjugated "free" antibody elutes around 11.5 milliliters volume and is discarded.

Before the present invention is described in further detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "a probe" includes a plurality of probes, and the like. Additionally, use of specific plural references, such as "two," "three," etc., read on larger numbers of the same subject unless the context clearly dictates otherwise.

Terms such as "connected," "attached," "conjugated" and "linked" are used interchangeably herein and encompass direct as well as indirect connection, attachment, linkage or conjugation unless the context clearly dictates otherwise; in one example, the phrase "conjugated polymer" is used in accordance with its ordinary meaning in the art and refers to a polymer containing an extended series of unsaturated bonds, and that context dictates that the term "conjugated" should be interpreted as something more than simply a direct or indirect connection, attachment or linkage.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

A variety of chemical modifications of fluorene polymers have been tried for exploring their biological detection applications. It has been noted that any substitutions at positions 1, 2, 3, 6, 7, and 8 significantly decrease the fluorescence intensity of the resulted polymer conjugates. In addition, these substituted fluorene polymer conjugates also have poor water solubility. Efforts were focused on positions 4 and 5. The initial efforts on different substitutions and different crosslinking at positions 4 and 5 did not generate the desired polymers. The halogenation, alkylation, amination of positions 4 and 5 and the crosslinking of positions 4 and 5 by 5, 6 and 8-member rings gave undesired fluorene polymer conjugates. However, this instant rigid and bridged fluorene polymer conjugates unexpectedly gave the desired biological properties where positions 4 and 5 of a fluorene are crosslinked by a 7 member ring. It has been found that these polymer conjugates have the following properties: (1) high fluorescence quantum yield; (2) red-shifted emission; (3) high water solubility; (4) high linearity; (5) high planarity; (6) high fluorescence resonance energy transfer (FRET) efficiency when a second fluorophore is coupled to the polymer; and (7) high photostability. It has been discovered that the rigid and bridged polyfluorene polymers described herein unexpectedly mitigated problems discussed in the background section and resulted in fluorescent polymer conjugates that are substantially more fluorescent on proteins, nucleic acids and other biopolymers. The enhanced fluorescence intensity of polymer-biomolecule conjugates of the invention results in greater assay sensitivity.

The present disclosure provides polymer conjugates comprise rigid and bridged fluorene-based polymer conjugates. These biological conjugates are used to locate or detect the interaction or presence of analytes or ligands in a sample. Kits incorporating such polymers or polymer conjugates facilitate their use in such methods.

The present disclosure provides polymer conjugates comprising rigid and bridged fluorene-based polymer conjugate that contains: 1) a polymer comprising rigid and bridged fluorene monomers; and 2) a biological substrate (BS). The polymer conjugates of the invention typically have the structure of Formula I:

Formula I

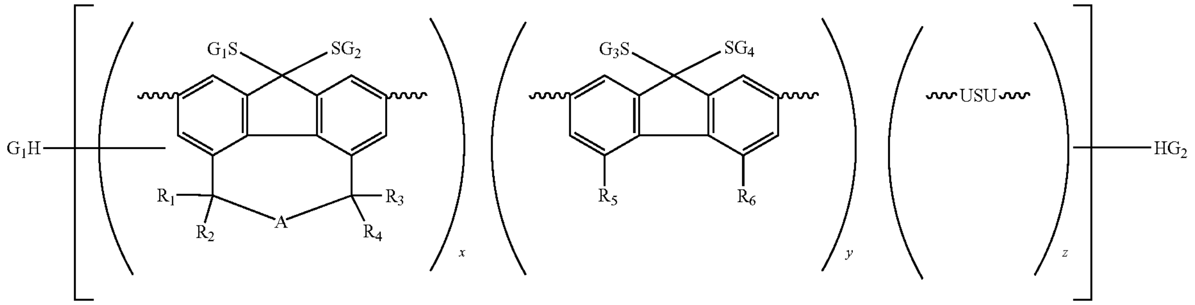

wherein the polymer conjugate comprises three monomer units that are randomly distributed along the polymer main chain; wherein A=N—$R_{10}$, P—$R_{11}$, O═P—$R_{11}$, O═P—$OR_{11}$, $R_{11}$—C—$R_{12}$, $R_{11}$—Si—$R_{12}$, $R_{11}$—S—$R_{12}$, O═S—$R_{11}$, O═S(O)—$R_{11}$; USU is an unsaturated unit, a double bond, a triple bond, an aryl, or a heteroaryl; R1 to R12 independently represent hydrogen, an alkyl, a polyethylene glycol (PEG), an aryl, a heteroaryl group, or a linked biological substrate (L-BS) wherein linker (L) is an alkyl or a PEG; wherein SG1 to SG4 independently represent an alkyl, a water soluble group or a L-BS; wherein HG1 and HG2 independently represent a hydrogen, an aryl, a halogen or a boronyl, an aryl, a heteroaryl group, or a L-BS; and wherein x, y and z are integers from 0-100, provided that (1) the ratio of BS/polymer is 0.2-3, (2) the ratio of x/(y+z) is >1, and (3) the sum of x+y+z is >10.

In one preferred embodiment, the disclosure provides the polymer conjugate of formula I, wherein R1 to R6 independently represent hydrogen, methyl, or ethyl; wherein SG1 to SG4 independently represent a PEG, an alkyl, a carboxyalkyl, a sulfonylalkyl, a phosphonylalkyl, an aminoalkyl or L-BS; wherein L is an alkyl chain or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; and wherein x, y and z are integer from 0-80, provided that (1) the ratio of BS/polymer is 1-2, (2) the ratio of x/(y+z) is >1, and (3) the sum of x+y+z is >20.

In another preferred embodiment, the disclosure provides the polymer conjugate of formula I, wherein R1 to R6 are hydrogen; wherein SG1 and SG2 are PEG; wherein SG3 to SG4 independently represent a PEG, an alkyl, a carboxyalkyl, a sulfonylalkyl, a phosphonylalkyl, an aminoalkyl or a L-BS; wherein L is an alkyl chain or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; and wherein x, y and z are integer from 0-80, provided that (1) the ratio of BS/polymer is 1-2, (2) the ratio of x/(y+z) is >1, and (3) the sum of x+y+z is >20.

In another preferred embodiment, the disclosure provides the polymer conjugate of formula I, wherein SG3 to SG4 independently represent a PEG, an alkyl, a carboxyalkyl, or a L-BS.

In another preferred embodiment, the disclosure provides the polymer conjugate of formula I, wherein SG3 to SG4 independently represent a PEG, an alkyl, an aminoalkyl or a L-BS.

In another preferred embodiment, the disclosure provides the polymer conjugate of formula I, wherein SG1 and SG2 are independently PEG6 to PEG18.

In another preferred embodiment, the disclosure provides the polymer conjugate of formula I, wherein the ratio of BS/polymer is 1; and wherein the sum of x+y+z is 30-80.

In another preferred embodiment, the disclosure provides the polymer conjugate of formula I, wherein SG3 to SG4 independently represent a PEG, a methyl, a carboxyalkyl or a L-BS.

In another preferred embodiment, the disclosure provides the polymer conjugate of formula I, wherein SG3 to SG4 independently represent a PEG, a methyl, an aminoalkyl or a L-BS.

In another preferred embodiment, the disclosure provides the polymer conjugate of formula I, wherein R1 to R6 are hydrogen; wherein SG1 to SG4 independently represent a PEG, an alkyl, a carboxyalkyl, a sulfonylalkyl, a phosphonylalkyl, or an aminoalkyl; wherein HG1 and HG2 independently represent a hydrogen, an aryl, a halogen, a boronyl or or a L-BS; wherein L is an alkyl chain or a PEG chain; wherein BS is an antibody, a peptide, a protein, an oligonucleotide, a nucleic acid or a carbohydrate; and wherein x, y and z are integer from 0-80, provided that (1) the ratio of BS/polymer is 1-2, (2) the ratio of x/(y+z) is >1, and (3) the sum of x+y+z is >20.

In another preferred embodiment, the disclosure provides the polymer conjugate of formula I, wherein the ratio of BS/polymer is 1; and wherein the sum of x+y+z is 30-80.

In another preferred embodiment, the disclosure provides the polymer conjugate of formula I, wherein HG1 and HG2 independently represent a hydrogen, a carboxyaryl, or a L-BS.

In another preferred embodiment, the disclosure provides the polymer conjugate of formula I, wherein HG1 and HG2 independently represent a halogen, a boronyl, a carboxyaryl, or a L-BS.

A preferred embodiment is a polymer conjugate of Formula II:

Formula II

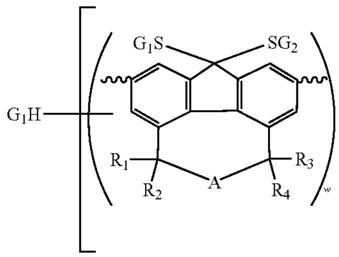

-continued

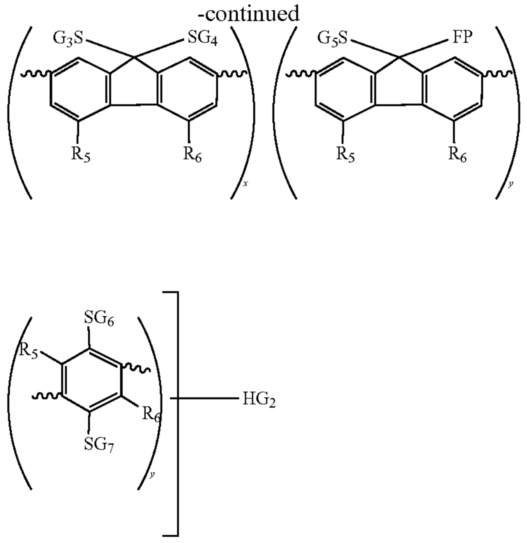

wherein the polymer conjugate comprises four monomer units that are randomly distributed along the polymer main chain; wherein fluorophore (FP) is a fluorescent dye that has absorption maximum longer than 370 nm, and emission maximum longer than 400 nm with fluorescence quantum yield larger than 5%; wherein A=N—$R_{10}$, P—$R_{11}$, O=P—$R_{11}$, O=P—ORni, $R_{11}$—C—$R_{12}$, $R_{11}$—Si—$R_{12}$, $R_{11}$—S—$R_{12}$, O=S—$R_{11}$, O=S(O)—$R_{11}$; R1 to R12 independently represent hydrogen, an alkyl, a PEG, an aryl, a heteroaryl group, or a L-BS; wherein L is an alkyl, a PEG or a FP; wherein SG1 to SG7 independently represent an alkyl, a water soluble group or a L-BS; wherein HG1 and HG2 independently represent an hydrogen, a halogen, a boronyl, an alkyl, an aryl, a heteroaryl group, or a L-BS; wherein w, x and z are integers from 0-100; and wherein y is an integer from 1 to 20, provided that (1) the ratio of BS/polymer is 0.2-3, (2) the ratio of w/(x+y+z) is >1, and (3) the sum of w+x+y+z is >10.

In another preferred embodiment, the disclosure provides the polymer conjugate of formula II, wherein FP is a fluorescein, a rhodamine, a rhodol, a cyanine, a BODIPY, a squaraine, a coumarin, a perylenediimide, a diketopyrrolopyrrole, a porphyrin or a phthalocyanine; wherein R1 to R6 independently represent hydrogen, methyl, or ethyl; wherein SG1 to SG7 independently represent a PEG, an alkyl, a carboxyalkyl, a sulfonylalkyl, a phosphonylalkyl, an aminoalkyl or a L-BS; wherein L is an alkyl chain, a FP or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; wherein w, x and z are integers from 0-80; and wherein y is an integer from 1 to 10, provided that (1) the ratio of BS/polymer is 1-2, (2) the ratio of w/(x+y+z) is >1, and (3) the sum of w+x+Y+z is >20.

In another preferred embodiment, the disclosure provides the polymer conjugate of formula II, wherein R1 to R6 are hydrogen.

In another preferred embodiment, the disclosure provides the polymer conjugate of formula II, wherein the ratio of BS/polymer is 1; wherein the sum of w+x+y+z is 30-80.

In another preferred embodiment, the disclosure provides the polymer conjugate of formula II, wherein FP is a fluorescein, a rhodamine, a cyanine, a BODIPY, a squaraine, a perylenediimide, or a phthalocyanine.

In another preferred embodiment, the disclosure provides the polymer conjugate of formula II, wherein FP is a rhodamine.

In another preferred embodiment, the disclosure provides the polymer conjugate of formula II, wherein FP is a cyanine.

In another preferred embodiment, the disclosure provides the polymer conjugate of formula II, wherein FP is a fluorescein, a rhodamine, a rhodol, a cyanine, a BODIPY, a squaraine, a coumarin, a perylenediimide, a diketopyrrolopyrrole, a porphyrin or a phthalocyanine; wherein R1 to R6 are hydrogen; wherein SG1 to SG7 independently represent a PEG, an alkyl, a carboxyalkyl, a sulfonylalkyl, a phosphonylalkyl, or an aminoalkyl; wherein HG1 and HG2 independently represent a hydrogen, an aryl, a halogen, a boronyl or a L-BS; wherein L is an alkyl chain, a FP or a PEG chain; wherein BS is an antibody, a peptide, a protein, an oligonucleotide, a nucleic acid or a carbohydrate; wherein w, x and z are integers from 0-80; and wherein y is an integer from 1 to 10, provided that (1) the ratio of BS/polymer is 1-2, (2) the ratio of w/(x+y+z) is >1, and (3) the sum of w+x+y+z is >20.

In another preferred embodiment, the disclosure provides the polymer conjugate of formula II, wherein the ratio of BS/polymer is 1; and wherein the sum of x+y+z is 30-80.

In another preferred embodiment, the disclosure provides the polymer conjugate of formula II, wherein HG1 and HG2 independently represent a hydrogen, a carboxyaryl, or a L-BS.

In another preferred embodiment, the disclosure provides the polymer conjugate of formula II, wherein HG1 and HG2 independently represent a halogen, a boronyl, a carboxyaryl, or a L-BS.

A preferred embodiment is a polymer conjugate of Formula III:

Formula III

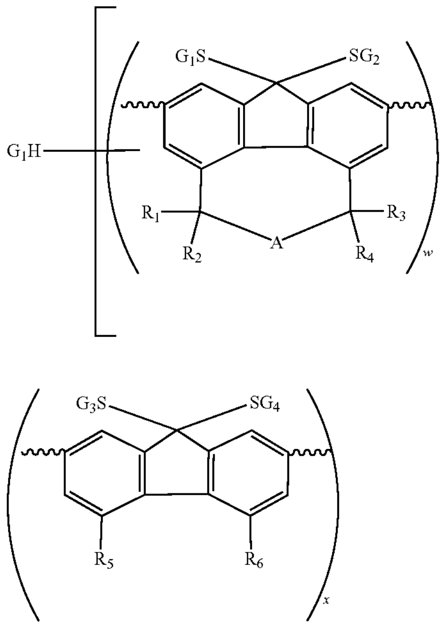

-continued

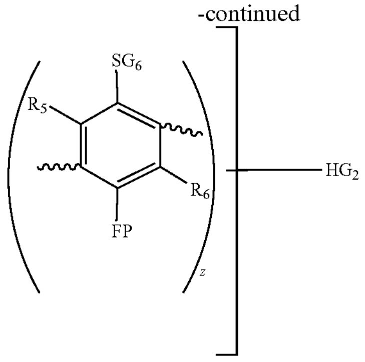

wherein the polymer conjugate comprises four monomer units that are randomly distributed along the polymer main chain; wherein fluorophore (FP) is a fluorescent dye that has absorption maximum longer than 370 nm, and emission maximum longer than 400 nm with fluorescence quantum yield larger than 5%; wherein A=N—$R_{10}$, P—$R_{11}$, O═P—$R_{11}$, O═P—O$R_{11}$, $R_{11}$—C—$R_{12}$, $R_{11}$—Si—$R_{11}$, $R_{11}$—S—$R_{12}$, O═S—$R_{11}$, O═S(O)—$R_{11}$; R1 to R12 independently represent hydrogen, an alkyl, a PEG, an aryl, a heteroaryl group, or a L-BS; wherein L is an alkyl, a PEG or a FP; wherein SG1 to SG6 independently represent an alkyl, a water soluble group or a L-BS; wherein HG1 and HG2 independently represent an hydrogen, a halogen, a boronyl, an alkyl, an aryl, a heteroaryl group, or a L-BS; wherein w, x and z are integers from 0-100; and wherein y is an integer from 1 to 20, provided that (1) the ratio of BS/polymer is 0.2-3, (2) the ratio of w/(x+z) is >1, and (3) the sum of w+x+z is >10.

In another preferred embodiment, the disclosure provides the polymer conjugate of formula III, wherein FP is a fluorescein, a rhodamine, a rhodol, a cyanine, a BODIPY, a squaraine, a coumarin, a perylenediimide, a diketopyrrolopyrrole, a porphyrin or a phthalocyanine; wherein R1 to R6 independently represent hydrogen, methyl, or ethyl; wherein SG1 to SG6 independently represent a PEG, an alkyl, a carboxyalkyl, a sulfonylalkyl, a phosphonylalkyl, an aminoalkyl or a L-BS; wherein L is an alkyl chain, a FP or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; wherein w, x and z are integers from 0-80; and wherein y is an integer from 1 to 10, provided that (1) the ratio of BS/polymer is 1-2, (2) the ratio of w/(x+z) is >1, and (3) the sum of w+x+z is >20.

In another preferred embodiment, the disclosure provides the polymer conjugate of formula III, wherein R1 to R6 are hydrogen.

In another preferred embodiment, the disclosure provides the polymer conjugate of formula III, wherein the ratio of BS/polymer is 1; wherein the sum of w+x+z is 30-80.

In another preferred embodiment, the disclosure provides the polymer conjugate of formula III, wherein FP is a fluorescein, a rhodamine, a cyanine, a BODIPY, a squaraine, a perylenediimide, or a phthalocyanine.

In another preferred embodiment, the disclosure provides the polymer conjugate of formula III, wherein FP is a rhodamine.

In another preferred embodiment, the disclosure provides the polymer conjugate of formula III, wherein FP is a cyanine.

In another preferred embodiment, the disclosure provides the polymer conjugate of formula III, wherein FP is a fluorescein, a rhodamine, a rhodol, a cyanine, a BODIPY, a squaraine, a coumarin, a perylenediimide, a diketopyrrolopyrrole, a porphyrin or a phthalocyanine; wherein R1 to R6 are hydrogen; wherein SG1 to SG6 independently represent a PEG, an alkyl, a carboxyalkyl, a sulfonylalkyl, a phosphonylalkyl, or an aminoalkyl; wherein HG1 and HG2 independently represent a hydrogen, an aryl, a halogen, a boronyl or a L-BS; wherein L is an alkyl chain, a FP or a PEG chain; wherein BS is an antibody, a peptide, a protein, an oligonucleotide, a nucleic acid or a carbohydrate; wherein w, x and z are integers from 0-80; and wherein y is an integer from 1 to 10, provided that (1) the ratio of BS/polymer is 1-2, (2) the ratio of w/(x+z) is >1, and (3) the sum of w+x+z is >20.

In another preferred embodiment, the disclosure provides the polymer conjugate of formula III, wherein the ratio of BS/polymer is 1; and wherein the sum of x+z is 30-80.

In another preferred embodiment, the disclosure provides the polymer conjugate of formula III, wherein HG1 and HG2 independently represent a hydrogen, a carboxyaryl, or a L-BS.

In another preferred embodiment, the disclosure provides the polymer conjugate of formula III, wherein HG1 and HG2 independently represent a halogen, a boronyl, a carboxyaryl, or a L-BS.

A preferred embodiment is a polymer conjugate of Formula IV:

Formula IV

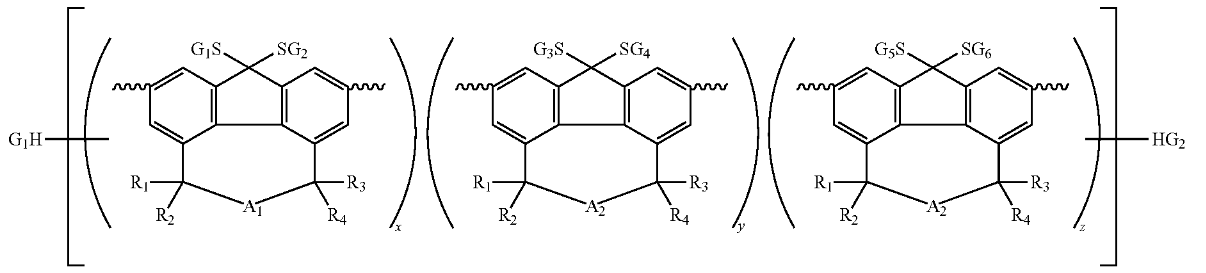

wherein the polymer conjugate comprises three monomer units that are randomly distributed along the polymer main chain; wherein A1, A2 or A3=N—$R_{10}$, P—$R_{11}$, O═P—$R_{11}$, O═P—O$R_{11}$, $R_{11}$—C—$R_{12}$, $R_{11}$—Si—$R_{12}$, $R_{11}$—S—$R_{12}$, O═S—$R_{11}$, O═S(O)—$R_{11}$; R1 to R12 independently represent hydrogen, an alkyl, a polyethylene glycol (PEG), an aryl, a heteroaryl group, or a linked biological substrate (L-BS); wherein linker (L) is an alkyl or a PEG; wherein SG1 to SG6 independently represent an alkyl, a water soluble group or a L-BS; wherein HG1 and HG2 independently represent a hydrogen, an aryl, a halogen or a boronyl, an aryl, a heteroaryl group, or a L-BS; and wherein x, y and z are integers from 0-100, provided that (1) the ratio of BS/polymer is 0.2-3, and (2) the sum of x+y+z is >10.

In another preferred embodiment, the disclosure provides the polymer conjugate of formula IV, wherein R1 to R4 independently represent hydrogen, methyl, or ethyl; wherein SG1 to SG6 independently represent a PEG, an alkyl, a carboxyalkyl, a sulfonylalkyl, a phosphonylalkyl, an aminoalkyl or L-BS; wherein L is an alkyl chain or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; and wherein x, y and z are integer from 0-80, provided that (1) the ratio of BS/polymer is 1-2, and (2) the sum of x+y+z is >20.

In another preferred embodiment, the disclosure provides the polymer conjugate of formula IV, wherein R1 to R4 are hydrogen; wherein SG1 and SG2 are PEG; wherein SG3 to SG6 independently represent a PEG, an alkyl, a carboxyalkyl, a sulfonylalkyl, a phosphonylalkyl, an aminoalkyl or a L-BS; wherein L is an alkyl chain or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; and wherein x, y and z are integer from 0-80, provided that (1) the ratio of BS/polymer is 1-2, and (2) the sum of x+y+z is >20.

In another preferred embodiment, the disclosure provides the polymer conjugate of formula IV, wherein SG3 to SG6 independently represent a PEG, an alkyl, a carboxyalkyl, or a L-BS.

In another preferred embodiment, the disclosure provides the polymer conjugate of formula IV, wherein SG3 to SG6 independently represent a PEG, an alkyl, an aminoalkyl or a L-BS.

In another preferred embodiment, the disclosure provides the polymer conjugate of formula IV, wherein the ratio of BS/polymer is 1; and wherein the sum of x+y+z is 30-80.

In another preferred embodiment, the disclosure provides the polymer conjugate of formula IV, wherein SG3 to SG6 independently represent a PEG, a methyl, a carboxyalkyl or a L-BS.

In another preferred embodiment, the disclosure provides the polymer conjugate of formula IV, wherein SG3 to SG6 independently represent a PEG, a methyl, an aminoalkyl or a L-BS.

In another preferred embodiment, the disclosure provides the polymer conjugate of formula IV, wherein R1 to R4 are hydrogen; wherein SG1 to SG6 independently represent a PEG, an alkyl, a carboxyalkyl, a sulfonylalkyl, a phosphonylalkyl, or an aminoalkyl; wherein HG1 and HG2 independently represent a hydrogen, an aryl, a halogen, a boronyl or or a L-BS; wherein L is an alkyl chain or a PEG chain; wherein BS is an antibody, a peptide, a protein, an oligonucleotide, a nucleic acid or a carbohydrate; and wherein x, y and z are integer from 0-80, provided that (1) the ratio of BS/polymer is 1-2, (2) the ratio of x/(y+z) is >1, and (3) the sum of x+y+z is >20.

In another preferred embodiment, the disclosure provides the polymer conjugate of formula IV, wherein the ratio of BS/polymer is 1; and wherein the sum of x+y+z is 30-80.

In another preferred embodiment, the disclosure provides the polymer conjugate of formula IV, wherein HG1 and HG2 independently represent a hydrogen, a carboxyaryl, or a L-BS.

In another preferred embodiment, the disclosure provides the polymer conjugate of formula IV, wherein HG1 and HG2 independently represent a halogen, a boronyl, a carboxyaryl, or a L-BS.

A preferred embodiment is a polymer conjugate of Formula V:

Formula V

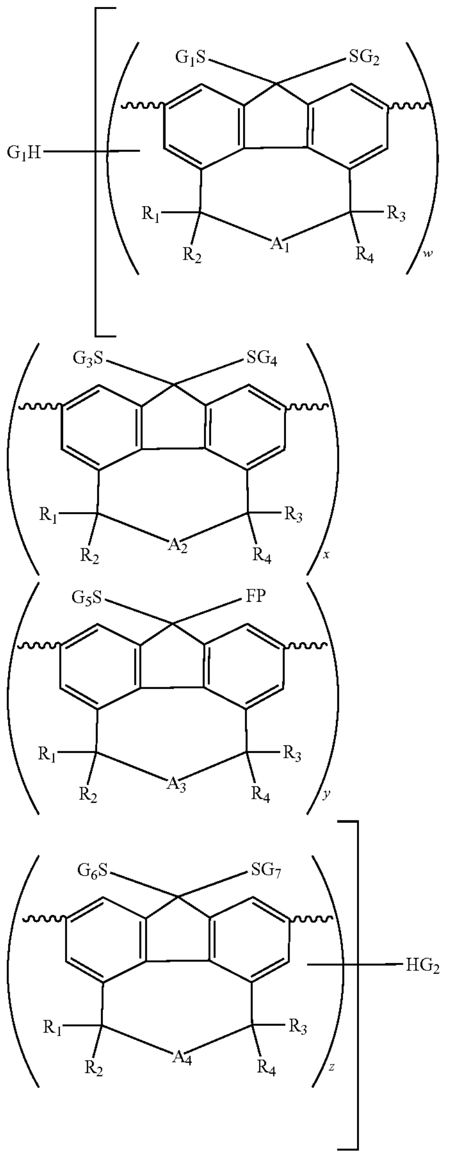

wherein the polymer conjugate comprises four monomer units that are randomly distributed along the polymer main chain; wherein fluorophore (FP) is a fluorescent dye that has absorption maximum longer than 370 nm, and emission maximum longer than 400 nm with fluorescence quantum yield larger than 5%; wherein A1, A2, A3 or A4=N—$R_{10}$, P—$R_{11}$, O═P—$R_{11}$, O═P—$OR_{11}$, $R_{11}$—C—$R_{12}$, $R_{11}$—Si—$R_{12}$, $R_{11}$—S—$R_{12}$, O═S—$R_{11}$, O═S(O)—$R_{11}$; R1 to R12 independently represent hydrogen, an alkyl, a PEG, an aryl, a heteroaryl group, or a L-BS wherein L is an alkyl, a PEG or a FP; wherein SG1 to SG7 independently represent an alkyl, a water soluble group or a L-BS; wherein HG1 and HG2 independently represent an hydrogen, a halogen, a boronyl, an alkyl, an aryl, a heteroaryl group, or a L-BS; wherein w, x and z are integers from 0-100; and wherein y is an integer from 1 to 20, provided that (1) the ratio of BS/polymer is 0.2-3, and (2) the sum of w+x+y+z is >10.

In another preferred embodiment, the disclosure provides the polymer conjugate of formula V, wherein FP is a fluorescein, a rhodamine, a rhodol, a cyanine, a BODIPY, a squaraine, a coumarin, a perylenediimide, a diketopyrrolopyrrole, a porphyrin or a phthalocyanine; wherein R1 to R4 independently represent hydrogen, methyl, or ethyl; wherein SG1 to SG7 independently represent a PEG, an alkyl, a carboxyalkyl, a sulfonylalkyl, a phosphonylalkyl, an aminoalkyl or a L-BS; wherein L is an alkyl chain, a FP or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; wherein w, x and z are integers from 0-80; and wherein y is an integer from 1 to 10, provided that (1) the ratio of BS/polymer is 1-2, and (2) the sum of w+x+y+z is >20.

In another preferred embodiment, the disclosure provides the polymer conjugate of formula V, wherein R1 to R4 are hydrogen.

In another preferred embodiment, the disclosure provides the polymer conjugate of formula V, wherein the ratio of BS/polymer is 1; and wherein the sum of w+x+y+z is 30-80.

In another preferred embodiment, the disclosure provides the polymer conjugate of formula V, wherein FP is a fluorescein, a rhodamine, a cyanine, a BODIPY, a squaraine, a perylenediimide, or a phthalocyanine.

In another preferred embodiment, the disclosure provides the polymer conjugate of formula V, wherein FP is a rhodamine.

In another preferred embodiment, the disclosure provides the polymer conjugate of formula V, wherein FP is a cyanine.

In another preferred embodiment, the disclosure provides the polymer conjugate of formula V, wherein FP is a fluorescein, a rhodamine, a rhodol, a cyanine, a BODIPY, a squaraine, a coumarin, a perylenediimide, a diketopyrrolopyrrole, a porphyrin or a phthalocyanine; wherein R1 to R4 are hydrogen; wherein SG1 to SG7 independently represent a PEG, an alkyl, a carboxyalkyl, a sulfonylalkyl, a phosphonylalkyl, or an aminoalkyl; wherein HG1 and HG2 independently represent a hydrogen, an aryl, a halogen, a boronyl or a L-BS; wherein L is an alkyl chain, a FP or a PEG chain; wherein BS is an antibody, a peptide, a protein, an oligonucleotide, a nucleic acid or a carbohydrate; wherein w, x and z are integers from 0-80; and wherein y is an integer from 1 to 10, provided that (1) the ratio of BS/polymer is 1-2, and (2) the sum of w+x+y+z is >20.

In another preferred embodiment, the disclosure provides the polymer conjugate of formula V, wherein the ratio of BS/polymer is 1; and wherein the sum of x+y+z is 30-80.

In another preferred embodiment, the disclosure provides the polymer conjugate of formula V, wherein HG1 and HG2 independently represent a hydrogen, a carboxyaryl, or a L-BS.

In another preferred embodiment, the disclosure provides the polymer conjugate of formula V, wherein HG1 and HG2 independently represent a halogen, a boronyl, a carboxyaryl, or a L-BS.

In another preferred embodiment, the disclosure further provides a method of detecting an analyte in a sample, comprising a) combining said sample with a detection reagent comprising a polymer conjugate having the structure of Formula I under conditions under which said detection reagent will bind said analyte; and
b) detecting the detection reagent bound analyte by fluorescence, wherein the polymer conjugate comprises three monomer units that are randomly distributed along the polymer main chain; wherein R1 to R6 independently represent hydrogen, an alkyl, a polyethylene glycol (PEG), an aryl, a heteroaryl group, or a linked biological substrate (L-BS); wherein linker (L) is an alkyl or a PEG; wherein SG1 to SG6 independently represent an alkyl, a water soluble group or a L-BS; wherein HG1 and HG2 independently represent a hydrogen, an aryl, a halogen or a boronyl, an aryl, a heteroaryl group, or a L-BS; and wherein x, y and z are integers from 0-100, provided that (1) the ratio of BS/polymer is 0.2-3, (2) the ratio of x/(y+z) is >1, and (3) the sum of x+y+z is >10.

In another preferred embodiment, the disclosure provides a method of detecting an analyte in a sample, comprising a) combining said sample with a detection reagent comprising a polymer conjugate having the structure of Formula II under conditions under which said detection reagent will bind said analyte; and
b) detecting the detection reagent bound analyte by fluorescence, wherein the polymer conjugate comprises four monomer units that are randomly distributed along the polymer main chain; wherein fluorophore (FP) is a fluorescent dye that has absorption maximum longer than 370 nm, and emission maximum longer than 400 nm with fluorescence quantum yield larger than 5%; wherein R1 to R6 independently represent hydrogen, an alkyl, a PEG, an aryl, a heteroaryl group, or a L-BS; wherein L is an alkyl, a PEG or a FP; wherein SG1 to SG7 independently represent an alkyl, a water soluble group or a L-BS; wherein HG1 and HG2 independently represent an hydrogen, a halogen, a boronyl, an alkyl, an aryl, a heteroaryl group, or a L-BS; wherein w, x and z are integers from 0-100; and wherein y is an integer from 1 to 20, provided that (1) the ratio of BS/polymer is 0.2-3, (2) the ratio of w/(x+y+z) is >1, and (3) the sum of w+x+y+z is >10.

In another preferred embodiment, the disclosure further provides a method of detecting an analyte in a sample, comprising a) combining said sample with a detection reagent comprising a polymer conjugate having the structure of Formula III under conditions under which said detection reagent will bind said analyte; and
b) detecting the detection reagent bound analyte by fluorescence, wherein the polymer conjugate comprises three monomer units that are randomly distributed along the polymer main chain; wherein R1 to R4 independently represent hydrogen, an alkyl, a polyethylene glycol (PEG), an aryl, a heteroaryl group, or a linked biological substrate (L-BS); wherein linker (L) is an alkyl or a PEG; wherein SG1 to SG6 independently represent an alkyl, a water soluble group or a L-BS; wherein HG1 and HG2 independently represent a hydrogen, an aryl, a halogen or a boronyl, an aryl, a heteroaryl group, or a L-BS; and wherein x, y and z are integers from 0-100, provided that (1) the ratio of BS/polymer is 0.2-3, and (2) the sum of x+y+z is >10.

In another preferred embodiment, the disclosure provides a method of detecting an analyte in a sample, comprising a) combining said sample with a detection reagent comprising a polymer conjugate having the structure of Formula IV under conditions under which said detection reagent will bind said analyte; and
b) detecting the detection reagent bound analyte by fluorescence, wherein the polymer conjugate comprises four monomer units that are randomly distributed along the polymer main chain; wherein fluorophore (FP) is a fluorescent dye that has absorption maximum longer than 370 nm, and emission maximum longer than 400 nm with fluorescence quantum yield larger than 5%; wherein R1 to R4 independently represent hydrogen, an alkyl, a PEG, an aryl, a heteroaryl group, or a L-BS; wherein L is an alkyl, a PEG or a FP; wherein SG1 to SG7 independently represent an alkyl, a water soluble group or a L-BS; wherein HG1 and HG2 independently represent an hydrogen, a halogen, a boronyl, an alkyl, an aryl, a heteroaryl group, or a L-BS; wherein x, y and z are integers from 0-100; and wherein y is an integer from 1 to 20, provided that (1) the ratio of BS/polymer is 0.2-3, and (2) the sum of x+y+z is >10.

In another preferred embodiment, the disclosure provides a method of detecting an analyte in a sample, comprising a) combining said sample with a detection reagent comprising a polymer conjugate having the structure of Formula V under conditions under which said detection reagent will bind said analyte; and
b) detecting the detection reagent bound analyte by fluorescence, wherein the polymer conjugate comprises four monomer units that are randomly distributed along the polymer main chain; wherein fluorophore (FP) is a fluorescent dye that has absorption maximum longer than 370 nm, and emission maximum longer than 400 nm with fluorescence quantum yield larger than 5%; wherein R1 to R4 independently represent hydrogen, an alkyl, a PEG, an aryl, a heteroaryl group, or a L-BS; wherein L is an alkyl, a PEG or a FP; wherein SG1 to SG7 independently represent an alkyl, a water soluble group or a L-BS; wherein HG1 and HG2 independently represent an hydrogen, a halogen, a boronyl, an alkyl, an aryl, a heteroaryl group, or a L-BS; wherein w, x and z are integers from 0-100; and wherein y is an integer from 1 to 20, provided that (1) the ratio of BS/polymer is 0.2-3, and (2) the sum of w+x+y+z is >10.

In another preferred embodiment, the disclosure provides the polymer conjugate of formula I, II, III, IV or V, wherein BS is an antibody.

In another preferred embodiment, the disclosure provides the polymer conjugate of formula I, II, III, IV or V, wherein BS is an anti-digoxigenin antibody.

In yet another preferred embodiment, the disclosure provides the polymer conjugate of formula I, II, III, IV or V, wherein BS is a goat anti-mouse IgG antibody, goat anti-rabbit IgG antibody, goat anti-human IgG antibody, donkey anti-mouse IgG antibody, donkey anti-rabbit IgG antibody, donkey anti-human IgG antibody, chicken anti-mouse IgG antibody, chicken anti-rabbit IgG antibody, or chicken anti-human IgG antibody.

In another preferred embodiment, the disclosure provides the polymer conjugate of formula I, II, III, IV or V, wherein BS is an avidin, streptavidin, neutravidin, or avidin.

In another preferred embodiment, the disclosure provides the polymer conjugate of formula I, II, III, IV or V, wherein the analyte is a target protein expressed on a cell surface.

In another preferred embodiment, wherein FP is a fluorescent dye selected from Table 1; wherein R1 to R4 are hydrogen; wherein SG1 to SG7 independently represent a PEG, an alkyl, a carboxyalkyl, a sulfonylalkyl, a phosphonylalkyl, or an aminoalkyl; wherein HG1 and HG2 independently represent a hydrogen, an aryl, a halogen, a boronyl, or a L-BS; wherein L is an alkyl chain, a FP or a PEG chain; wherein BS is an antibody, a peptide, a protein, an oligonucleotide, a nucleic acid or a carbohydrate; wherein w, x and z are integers from 0-80; and wherein y is an integer from 1 to 10, provided that (1) the ratio of BS/polymer is 1, and (2) the sum of w+x+y+z is 30-80.

The fluorophore (FP) linked to the polymers of the invention is typically a fluorescent dye that has absorption maximum longer than 370 nm, and emission maximum longer than 400 nm with fluorescence quantum yield larger than 10%. They are typically selected from coumarins, fluoresceins, rhodamines, cyanines, BODIPYs or other polycyclic aromatics. Many of them are commercially available as selectively listed in Table 1 as some examples.

TABLE 1

The typical fluorophores that can be linked to the fluorene polymers

| Fluorophore | Absorption (nm) | Emission (nm) |
|---|---|---|
| ATTO 465 | 453 | 508 |
| ATTO 488 | 501 | 523 |
| ATTO 495 | 495 | 527 |
| ATTO 514 | 511 | 533 |
| ATTO 532 | 532 | 553 |
| ATTO 550 | 554 | 576 |
| ATTO 565 | 563 | 592 |
| ATTO 590 | 594 | 624 |
| ATTO 594 | 601 | 627 |
| ATTO 610 | 615 | 634 |
| ATTO 620 | 619 | 643 |
| ATTO 633 | 629 | 657 |
| ATTO 647 | 645 | 669 |
| ATTO 647N | 644 | 669 |
| ATTO 655 | 663 | 684 |
| ATTO 665 | 663 | 684 |
| ATTO 680 | 680 | 700 |
| ATTO 700 | 700 | 719 |
| ATTO 725 | 729 | 752 |
| ATTO 740 | 740 | 764 |
| 5-carboxy-2,7-dichlorofluorescein | 504 | 529 |
| 5-Carboxyfluorescein (5-FAM) | 492 | 518 |
| 5-Carboxynapthofluorescein | 598 | 668 |
| 5-Carboxytetramethylrhodamine (5-TAMRA) | 542 | 568 |
| 5-FAM (5-Carboxyfluorescein) | 492 | 518 |
| 5-ROX | 578 | 604 |
| 6-TAMRA | 548 | 568 |
| 6-Carboxyrhodamine 6G | 518 | 543 |
| 6-CR6G | 518 | 543 |
| 6-JOE | 520 | 548 |
| 6-FAM | 494 | 517 |
| 6-ROX | 570 | 591 |
| Alexa Fluor 488 | 492 | 520 |

TABLE 1-continued

| The typical fluorophores that can be linked to the fluorene polymers | | |
|---|---|---|
| Fluorophore | Absorption (nm) | Emission (nm) |
| Alexa Fluor 532 | 532 | 554 |
| Alexa Fluor 546 | 557 | 573 |
| Alexa Fluor 568 | 578 | 603 |
| Alexa Fluor 594 | 594 | 618 |
| Alexa Fluor 633 | 632 | 650 |
| Alexa Fluor 647 | 647 | 666 |
| Alexa Fluor 660 | 668 | 698 |
| Alexa Fluor 680 | 679 | 702 |
| BODIPY 492/515 | 490 | 515 |
| BODIPY 493/503 | 533 | 549 |
| BODIPY 500/510 | 509 | 515 |
| BODIPY 505/515 | 502 | 510 |
| BODIPY 530/550 | 528 | 547 |
| BODIPY 542/563 | 543 | 563 |
| BODIPY 558/568 | 558 | 569 |
| BODIPY 564/570 | 564 | 570 |
| BODIPY 576/589 | 579 | 590 |
| BODIPY 581/591 | 584 | 592 |
| BODIPY 630/650-X | 625 | 642 |
| BODIPY 650/665-X | 647 | 665 |
| BODIPY 665/676 | 605 | 676 |
| BODIPY F1 | 505 | 513 |
| BODIPY R6G SE | 528 | 547 |
| BODIPY TMR | 542 | 574 |
| BODIPY TR | 589 | 617 |
| CF 488A | 490 | 515 |
| CF 555 | 555 | 565 |
| CF 568 | 562 | 583 |
| CF 594ST | 593 | 614 |
| CF 633 | 630 | 650 |
| CF 640R | 642 | 662 |
| CF 647 | 650 | 665 |
| CF 660C | 667 | 685 |
| CF 680 | 681 | 698 |
| CF680R | 680 | 701 |
| CF 750 | 755 | 777 |
| CF 770 | 770 | 797 |
| CF 790 | 784 | 806 |
| CL-NERF | 504 | 540 |
| CMFDA | 494 | 520 |
| Cy2 | 489 | 506 |
| Cy3 | 554 | 568 |
| Cy3.5 | 581 | 598 |
| Cy5 | 649 | 666 |
| Cy5.5 | 675 | 695 |
| Cy7 | 743 | 767 |
| DDAO | 646 | 659 |
| DiA | 456 | 591 |
| DiD | 644 | 665 |
| DiI | 549 | 565 |
| DyLight 488 | 493 | 518 |
| DyLight 550 | 562 | 576 |
| DyLight 594 | 593 | 618 |
| DyLight 633 | 638 | 658 |
| DyLight 650 | 652 | 672 |
| DyLight 680 | 692 | 712 |
| DyLight 755 | 754 | 776 |
| DyLight 800 | 777 | 794 |
| DiO | 487 | 502 |
| DiR | 748 | 780 |
| DM-NERF | 497 | 540 |
| DsRed | 558 | 583 |
| DTAF | 494 | 520 |
| DY-490 | 491 | 515 |
| DY-495 | 494 | 521 |
| DY-505 | 507 | 528 |
| DY-530 | 533 | 554 |
| DY-547 | 558 | 573 |
| DY-548 | 558 | 572 |
| DY-549 | 562 | 577 |
| DY-549P1 | 563 | 578 |
| DY-550 | 562 | 577 |
| DY-554 | 544 | 570 |
| DY-555 | 547 | 573 |
| DY-556 | 548 | 574 |

TABLE 1-continued

| The typical fluorophores that can be linked to the fluorene polymers | | |
|---|---|---|
| Fluorophore | Absorption (nm) | Emission (nm) |
| DY-560 | 560 | 578 |
| DY-590 | 581 | 600 |
| DY-591 | 581 | 598 |
| DY-594 | 594 | 615 |
| DY-605 | 600 | 624 |
| DY-610 | 610 | 632 |
| DY-615 | 623 | 643 |
| DY-630 | 638 | 658 |
| DY-631 | 637 | 657 |
| DY-632 | 636 | 658 |
| DY-633 | 638 | 658 |
| DY-634 | 636 | 657 |
| DY-635 | 648 | 670 |
| DY-636 | 647 | 670 |
| DY-647 | 653 | 673 |
| DY-648 | 655 | 676 |
| DY-649 | 656 | 670 |
| DY-649P1 | 654 | 672 |
| DY-650 | 656 | 676 |
| D Y -651 | 655 | 677 |
| DY-652 | 653 | 676 |
| DY-654 | 653 | 677 |
| DY-675 | 675 | 699 |
| DY-676 | 675 | 699 |
| DY-677 | 674 | 698 |
| DY-678 | 674 | 694 |
| DY-679 | 679 | 698 |
| DY-679P1 | 679 | 697 |
| DY-680 | 691 | 709 |
| DY-681 | 692 | 709 |
| DY-682 | 692 | 709 |
| DY-700 | 707 | 728 |
| DY-701 | 709 | 730 |
| DY-703 | 705 | 721 |
| DY-704 | 706 | 721 |
| DY-730 | 734 | 755 |
| DY-731 | 736 | 755 |
| DY-732 | 735 | 756 |
| DY-734 | 733 | 755 |
| DY-749 | 759 | 780 |
| DY-750 | 751 | 774 |
| DY-751 | 752 | 772 |
| DY-752 | 750 | 771 |
| DY-754 | 748 | 771 |
| DY-776 | 772 | 787 |
| DY-777 | 770 | 788 |
| DY-778 | 767 | 787 |
| DY-780 | 783 | 799 |
| DY-781 | 784 | 796 |
| DY-782 | 785 | 794 |
| DY-800 | 777 | 791 |
| DY-831 | 844 | 875 |
| Eosin | 524 | 545 |
| Erythrosin | 529 | 555 |
| FITC | 490 | 520 |
| Fluo-3 | 506 | 520 |
| Fluo-4 | 494 | 516 |
| Fluor-Ruby | 555 | 582 |
| FluorX | 494 | 520 |
| FM 1-43 | 479 | 598 |
| FM 4-46 | 515 | 640 |
| *i*Fluor 488 | 498 | 520 |
| *i*Fluor 555 | 558 | 578 |
| *i*Fluor 594 | 588 | 610 |
| *i*Fluor 647 | 649 | 670 |
| *i*Fluor 680 | 686 | 702 |
| *i*Fluor 700 | 696 | 720 |
| *i*Fluor 750 | 755 | 785 |
| *i*Fluor 780 | 787 | 808 |
| Lyso Tracker Green | 504 | 511 |
| Lyso Tracker Yellow | 551 | 576 |
| Mitotracker Green | 490 | 516 |
| Mitotracker Orange | 551 | 576 |
| Mitotracker Red | 578 | 599 |
| NBD | 466 | 539 |

TABLE 1-continued

The typical fluorophores that can be linked to the fluorene polymers

| Fluorophore | Absorption (nm) | Emission (nm) |
|---|---|---|
| Oregon Green 488 | 494 | 517 |
| Oregon Green 514 | 506 | 526 |
| PKH26 | 551 | 567 |
| PKH67 | 496 | 520 |
| Resorufin | 571 | 584 |
| RH 414 | 532 | 716 |
| Rhod-2 | 552 | 576 |
| Rhodamine | 550 | 573 |
| Rhodamine 110 | 496 | 520 |
| Rhodamine 123 | 507 | 529 |
| Rhodamine 6G | 525 | 555 |
| Rhodamine B | 540 | 625 |
| Rhodamine Green | 502 | 527 |
| Rhodamine Red | 570 | 590 |
| Rose Bengal | 525 | 550 |
| Spectrum Green | 497 | 538 |
| Spectrum Orange | 559 | 588 |
| Spectrum Red | 587 | 612 |
| SYTO 11 | 508 | 527 |
| SYTO 12 | 499 | 522 |
| SYTO 13 | 488 | 509 |
| SYTO 14 | 517 | 549 |
| SYTO 15 | 516 | 546 |
| SYTO 16 | 488 | 518 |
| SYTO 17 | 621 | 634 |
| SYTO 18 | 490 | 507 |
| SYTO 20 | 512 | 530 |
| SYTO 21 | 494 | 517 |
| SYTO 22 | 515 | 535 |
| SYTO 23 | 499 | 520 |
| SYTO 24 | 490 | 515 |
| SYTO 25 | 521 | 556 |
| SYTO 40 | 420 | 441 |
| SYTO 41 | 430 | 454 |
| SYTO 42 | 433 | 460 |
| SYTO 43 | 436 | 467 |
| SYTO 44 | 446 | 471 |
| SYTO 45 | 452 | 484 |
| SYTO 59 | 622 | 645 |
| SYTO 60 | 652 | 678 |
| SYTO 61 | 628 | 645 |
| SYTO 62 | 652 | 676 |
| SYTO 63 | 657 | 673 |
| SYTO 64 | 599 | 619 |
| SYTO 80 | 531 | 545 |
| SYT0 81 | 530 | 544 |
| SYTO 82 | 541 | 560 |
| SYTO 83 | 543 | 559 |
| SYTO 84 | 567 | 582 |
| SYTO 85 | 567 | 583 |
| SYTOX Blue | 445 | 470 |
| SYTOX Green | 504 | 523 |
| SYTOX Orange | 547 | 570 |
| Texas Red | 595 | 620 |
| Tide Fluor 2 (TF2) | 500 | 527 |
| Tide Fluor 2WS (TF2WS) | 502 | 525 |
| Tide Fluor 3 (TF3) | 555 | 584 |
| Tide Fluor 3WS(TF3WS) | 555 | 565 |
| Tide Fluor 4 (TF4) | 590 | 618 |
| Tide Fluor 5WS (TF5WS) | 649 | 664 |
| Tide Fluor 6WS (TF6WS) | 676 | 695 |
| Tide Fluor 7WS (TF7WS) | 749 | 775 |
| Tide Fluor 8WS (TF8WS) | 775 | 807 |
| TRITC | 550 | 573 |
| XTRITC | 582 | 601 |

Many embodiments of the compounds of the invention possess an overall electronic charge. It is to be understood that when such electronic charges are shown to be present, they are balanced by the presence of appropriate counterions, which may or may not be explicitly identified. A biologically compatible counterion, which is preferred for some applications, is not toxic in biological applications, and does not have a substantially deleterious effect on biomolecules. Where the compound of the invention is positively charged, the counterion is typically selected from, but not limited to, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Where the compound of the invention is negatively charged, the counterion is typically selected from, but not limited to, alkali metal ions, alkaline earth metal ions, transition metal ions, ammonium or substituted ammonium or pyridinium ions. Preferably, any necessary counterion is biologically compatible, is not toxic as used, and does not have a substantially deleterious effect on biomolecules. Counterions are readily changed by methods well known in the art, such as ion-exchange chromatography, or selective precipitation.

It is to be understood that the polymer conjugates of the invention have been drawn in one or another particular electronic resonance structure. Every aspect of the instant invention applies equally to polymer conjugates that are formally drawn with other permitted resonance structures, as the electronic charge on the subject polymer conjugates is delocalized throughout the polymer conjugate itself.

In another preferred embodiment of the invention, the polymer conjugate contains at least one L-BS or L-FP-BS, where BS attached to the polymer by a well-known reaction as listed in Table 2 as examples. In certain embodiments, the covalent linkage attaching the polymer to BS contains multiple intervening atoms that serve as a Linker (L). The polymers can be used to label a wide variety of biological, organic or inorganic substances that contain or are modified to contain functional groups with suitable reactivity, resulting in chemical attachment of the conjugated substances.

TABLE 2

Examples of functional groups for preparing covalent linkages of L-BS or FP-BS

| Functional Group (FG) | Matching Functional Group | Resulting covalent Linkages |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thioethers |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |

TABLE 2-continued

| Examples of functional groups for preparing covalent linkages of L-BS or FP-BS | | |
|---|---|---|
| Functional Group (FG) | Matching Functional Group | Resulting covalent Linkages |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |
| azides | alkynes | 1,2,3-triazoles |
| 1,2,4,5-tetrazines | cyclooctynes | pyradazines |
| hydroxylamines | aldehydes/ketones | oxamines |
| hydrazines | aldehydes/ketones | hydrazones |
| cysteines | aldehydes/ketones | thiazolidines |
| aryl azides | methyl 2-dinhenylphosphinobenzon | 2-diphenylphosphonyl-benzoamides |
| Nitrile-N-oxides | cycloalkynes | isoxazoles |
| anthracenes | maleimides | succinimides |

Choice of the linkage used to attach the polymer to a biological substrate to be conjugated typically depends on the functional group on the biological substrate to be conjugated and the type or length of covalent linkage desired. The types of functional groups typically present on the organic or inorganic biological substrates include, but are not limited to, amines, amides, thiols, alcohols, phenols, aldehydes, ketones, phosphonates, imidazoles, hydrazines, hydroxylamines, disubstituted amines, halides, epoxides, carboxylate esters, sulfonate esters, purines, pyrimidines, carboxylic acids, olefinic bonds, azide, alkyne, tetrazine or a combination of these groups. A single type of reactive site may be available on the biological substrate (typical for polysaccharides), or a variety of sites may occur (e.g. amines, thiols, alcohols, phenols), as is typical for proteins. A conjugated biological substrate may be conjugated to more than one polymer conjugate, which may be the same or different, or to a biological substrate that is additionally modified by a hapten, such as biotin. Alternatively multiple substrates might be conjugated to a single polymer. Although some selectivity can be obtained by careful control of the reaction conditions, selectivity of labeling is best obtained by selection of an appropriate reactive polymer conjugate.

Typically, a polymer will react with an amine, a thiol, an alcohol, an aldehyde or a ketone. Preferably, a polymer reacts with an amine, a thiol functional or a click-reactive group. In certain embodiments, a polymer reacts with an acrylamide, a reactive amine (including a cadaverine or ethylenediamine), an activated ester of a carboxylic acid (typically a succinimidyl ester of a carboxylic acid), an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, tetrazine, azide, alkyne or a thiol group. By "reactive platinum complex" is particularly meant chemically reactive platinum complexes such as described in U.S. Pat. Nos. 5,580,990; 5,714,327 and 5,985,566.

Where the polymer is a photoactivatable, such as an azide, diazirinyl, azidoaryl, or psoralen derivative, the polymer becomes chemically reactive only after illumination with light of an appropriate wavelength. Where polymer is an activated ester of a carboxylic acid, the reactive polymer is particularly useful for preparing polymer conjugates of proteins, nucleotides, oligonucleotides, or haptens. Where polymer is a maleimide or haloacetamide the reactive polymer is particularly useful for conjugation to thiol-containing biological substrates. Where polymer is a hydrazide, the reactive polymer is particularly useful for conjugation to periodate-oxidized carbohydrates and glycoproteins, and in addition is an aldehyde-fixable polar tracer for cell microinjection. Where polymer is click-reactive, the reactive polymer is particularly useful for conjugation to the complementary click-reactive substrate. Preferably, polymer is a carboxylic acid, a succinimidyl ester of a carboxylic acid, a haloacetamide, a hydrazine, an isothiocyanate, a maleimide group, an aliphatic amine, a perfluorobenzamido, an azidoperfluorobenzamido group, or a psoralen. More preferably, polymer is a succinimidyl ester of a carboxylic acid, a maleimide, an iodoacetamide, or a reactive platinum complex.

Based on the above-mentioned attributes, the appropriate reactive polymers of the invention are selected for the preparation of the desired polymer conjugates, whose advantageous properties make them useful for a wide variety of applications. Particularly useful polymer conjugates include, among others, conjugates where substrate is a peptide, a nucleotide, an antigen, a steroid, a vitamin, a drug, a hapten, a metabolite, a toxin, an environmental pollutant, an amino acid, a protein, a nucleic acid, a nucleic acid polymer, a carbohydrate, a lipid, an ion-complexing moiety, a glass or a non-biological polymer. Alternatively, substrate is a cell, a cellular system, a cellular fragment, or a subcellular particle (e.g. inter alia), a virus particle, a bacterial particle, a virus component, a biological cell (such as animal cell, plant cell, bacteria, yeast, or protist), or a cellular component. Reactive polymers typically label functional groups at the cell surface, in cell membranes, organelles, or cytoplasm.

Typically substrate is an amino acid, a peptide, a protein, a tyramine, a polysaccharide, an ion-complexing moiety, a nucleoside, a nucleotide, an oligonucleotide, a nucleic acid, a hapten, a psoralen, a drug, a hormone, a lipid, a lipid assembly, a polymer, a polymeric microparticle, a biological cell or virus. More typically, substrate is a peptide, a protein, a nucleotide, an oligonucleotide, or a nucleic acid. When conjugating polymer conjugates of the invention to such biopolymers, it is possible to incorporate more polymers per molecule to increase the fluorescent signal. For polymer-antibody conjugates, one polymer conjugated to an antibody is preferred.

In one embodiment, substrate is an amino acid (including those that are protected or are substituted by phosphonates, carbohydrates, or $C_1$ to $C_{25}$ carboxylic acids), or is a polymer of amino acids such as a peptide or protein. Preferred conjugates of peptides contain at least five amino acids, more preferably 5 to 36 amino acids. Preferred peptides include, but are not limited to neuropeptides, cytokines, toxins, protease substrates, and protein kinase substrates. Preferred protein conjugates include enzymes, antibodies, lectins, glycoproteins, histones, albumins, lipoproteins, avidin, streptavidin, other avidin proteins, protein A, protein G, phycobiliproteins and other fluorescent proteins, hormones, toxins, chemokines and growth factors. In one preferred aspect, the conjugated protein is a polymer antibody conjugate.

In one aspect of the invention, the substrate is a conjugated biological substrate that is an antibody (including intact antibodies, antibody fragments, and antibody sera, etc.), an amino acid, an angiostatin or endostatin, an avidin or streptavidin, a biotin (e.g. an amidobiotin, a biocytin, a desthiobiotin, etc.), a blood component protein (e.g. an albumin, a fibrinogen, a plasminogen, etc.), a dextran, an enzyme, an enzyme inhibitor, an IgG-binding protein (e.g. a protein A, protein G, protein A/G, etc.), a fluorescent protein (e.g. a phycobiliprotein, an aequorin, a green fluorescent protein, etc.), a growth factor, a hormone, a lectin (e.g. a wheat germ agglutinin, a conconavalin A, etc.), a lipopolysaccharide, a metal-binding protein (e.g. a calmodulin, etc.), a microorganism or portion thereof (e.g. a bacteria, a virus, a yeast, etc.), a neuropeptide and other biologically active factors (e.g. a dermorphin, a deltropin, an endomorphin, an endorphin, a tumor necrosis factor etc.), a non-biological microparticle (e.g. of ferrofluid, gold, polystyrene, etc.), a nucleotide, an oligonucleotide, a peptide toxin (e.g. an apamin, a bungarotoxin, a phalloidin, etc.), a phospholipid-binding protein (e.g. an annexin, etc.), a small-molecule drug (e.g. a methotrexate, etc.), a structural protein (e.g. an actin, a fibronectin, a laminin, a microtubule-associated protein, a tublin, etc.), or a tyramide.

In another preferred embodiment, the biological substrate is a nucleic acid base, nucleoside, nucleotide or a nucleic acid polymer, including those that are modified to possess an additional linker or spacer for attachment of the polymer conjugates of the invention, such as an alkynyl linkage (U.S. Pat. No. 5,047,519), an aminoallyl linkage (U.S. Pat. No. 4,711,955), or a heteroatom-substituted linker (U.S. Pat. No. 5,684,142) or other linkage. In another preferred embodiment, the conjugated biological substrate is a nucleoside or nucleotide analog that links a purine or pyrimidine base to a phosphate or polyphosphate moiety through a noncyclic spacer. In another preferred embodiment, the polymer conjugate is conjugated to the carbohydrate portion of a nucleotide or nucleoside, typically through a hydroxyl group but additionally through a thiol or amino group (U.S. Pat. Nos. 5,659,025; 5,668,268; 5,679,785). Typically, the conjugated nucleotide is a nucleoside triphosphate or a deoxynucleoside triphosphate or a dideoxynucleoside triphosphate. Incorporation of methylene moieties or nitrogen or sulfur heteroatoms into the phosphate or polyphosphate moiety is also useful. Nonpurine and nonpyrimidine bases such as 7-deazapurines (U.S. Pat. No. 6,150,510) and nucleic acids containing such bases can also be coupled to polymer conjugates of the invention. Nucleic acid adducts prepared by reaction of depurinated nucleic acids with amine, hydrazide or hydroxylamine derivatives provide an additional means of labeling and detecting nucleic acids, e.g. "A method for detecting abasic sites in living cells: age-dependent changes in base excision repair." Atamna H, Cheung I, Ames B N. PROC. NATL. ACAD. SCI. U.S.A. 97, 686-691 (2000).

Preferred nucleic acid polymer conjugates are labeled, single- or multi-stranded, natural or synthetic DNA or RNA, DNA or RNA oligonucleotides, or DNA/RNA hybrids, or incorporate an unusual linker such as morpholine derivatized phosphates, or peptide nucleic acids such as N-(2-aminoethyl)glycine units. When the nucleic acid is a synthetic oligonucleotide, it typically contains fewer than 50 nucleotides, more typically fewer than 25 nucleotides. Conjugates of peptide nucleic acids (PNA) (Nielsen, et al. U.S. Pat. No. 5,539,082) may be preferred for some applications because of their generally faster hybridization rates.

In one embodiment, the conjugated oligonucleotides of the invention are aptamers for a particular target molecule, such as a metabolite, polymer conjugate, hapten, or protein. That is, the oligonucleotides have been selected to bind preferentially to the target molecule. Methods of preparing and screening aptamers for a given target molecule have been previously described and are known in the art [for example, U.S. Pat. No. 5,567,588 to Gold (1996)].

In another preferred embodiment, substrate is a carbohydrate that is typically a polysaccharide, such as a dextran, heparin, glycogen, amylopectin, mannan, inulin, starch, agarose and cellulose. Alternatively, the carbohydrate is a polysaccharide that is a lipopolysaccharide. Preferred polysaccharide conjugates are dextran, or lipopolysaccharide conjugates.

Conjugates having an ion-complexing moiety serve as indicators for calcium, sodium, magnesium, zinc, potassium, or other biologically important metal ions. Preferred ion-complexing moieties are crown ethers (U.S. Pat. No. 5,405,975); derivatives of 1,2-bis-(2-aminophenoxyethane)-N,N,N,N-tetraacetic acid (BAPTA chelators; U.S. Pat. Nos. 5,453,517; 5,516,911 and 5,049,673); derivatives of 2-carboxymethoxyaniline-N,N-di-acetic acid (APTRA chelators; AM. J. PHYSIOL., 256, C540 (1989)); or pyridine- and phenanthroline-based metal ion chelators (U.S. Pat. No. 5,648,270); or derivatives of nitrilotriacetic acid, see e.g. "Single-step synthesis and characterization of biotinylated nitrilotriacetic acid, a unique reagent for the detection of histidine-tagged proteins immobilized on nitrocellulose", McMahan S A and Burgess R R, ANAL. BIOCHEM., 236, 101-106 (1996). Preferably, the ion-complexing moiety is a crown ether chelator, a BAPTA chelator, an APTRA chelator or a derivative of nitrilotriacetic acid.

Other conjugates of non-biological materials include polymer conjugates of organic or inorganic polymers, polymeric films, polymeric wafers, polymeric membranes, polymeric particles, or polymeric microparticles (magnetic and non-magnetic microspheres); iron, gold or silver particles; conducting and non-conducting metals and non-metals; and glass and plastic surfaces and particles. Conjugates are optionally prepared by copolymerization of a polymer conjugate that contains an appropriate functionality while preparing the polymer, or by chemical modification of a polymer that contains functional groups with suitable chemical reactivity. Other types of reactions that are useful for preparing polymer conjugates include catalyzed polymerizations or copolymerizations of alkenes and reactions of dienes with dienophiles, transesterifications or transaminations. In another preferred embodiment, the conjugated biological substrate is a glass or silica, which may be formed into an optical fiber or other structure.

In one embodiment, conjugates of biological polymers such as peptides, proteins, oligonucleotides, nucleic acid polymers are also labeled with at least a second fluorescent dye conjugate, which is optionally an additional polymer conjugate of the present invention, to form an energy-transfer pair. In some aspects of the invention, the labeled conjugate functions as an enzyme substrate, and enzymatic hydrolysis disrupts the energy transfer. In another preferred embodiment of the invention, the energy-transfer pair that incorporates a polymer conjugate of the invention is conjugated to an oligonucleotide that displays efficient fluorescence quenching in its hairpin conformation, e.g., the so-called "molecular beacons" of Tyagi, et al., NATURE BIOTECHNOLOGY, 16, 49 (1998).

The preparation of polymer conjugates using reactive polymer conjugates is well documented, e.g. e.g. U.S. Pat. Nos. 8,158,444; 8,455,613; 8,354,239; 8,362,193; and 8,575,303 to Gaylord, et al.; also WO 2013/101902 to Chiu et al. The other biological applications of polyfluorene polymers have been well documented by Thomas I I I et al. (Chem. Rev. 2007, 107, 1339); Zhu et al (Chem. Rev. 2012, 112, 4687) and Zhu et al. (Chem. Soc. Rev., 2011, 40, 3509). Conjugates typically result from mixing appropriate reactive polymers and biological substrate to be conjugated in a suitable solvent in which both are soluble. The polymer conjugates of the invention are readily soluble in aqueous solutions, facilitating conjugation reactions with most biological materials. For those reactive polymer conjugates that are photoactivated, conjugation requires illumination of the reaction mixture to activate the reactive polymer conjugates.

Reactive Polymer Synthesis

Synthesis of the reactive polymers of the invention depends on initial preparation of certain key intermediates as illustrated in FIG. 1. For simplicity, all but a few of the possible substituents are shown as hydrogen. These basic structures are optionally further substituted, during or after synthesis, to give the corresponding polymer conjugate substituents as defined above. It is recognized that there are many possible variations that may yield equivalent results. The methods for the synthesis of polymers that contain a variety of reactive functional groups such as those described in Table 2 are well documented in the art. Particularly useful are amine-reactive polymer conjugates such as "activated esters" of carboxylic acids, which are typically synthesized by coupling a carboxylic acid to a relatively acidic "leaving group". Other preferred amine-reactive groups include sulfonyl halides, which are prepared from sulfonic acids using a halogenating agent such as $PCl_5$ or $POCl_3$; halotriazines, which are prepared by the reaction of cyanuric halides with amines; and isocyanates or isothiocyanates, which are prepared from amines and phosgene or thiophosgene, respectively. Polymers containing azide, alkyne and tetrazine are particularly useful for conjugation to click-reactive group modified substrates such as the antibodies modified by a click-reactive group containing activated esters.

Polymers containing amines and hydrazides are particularly useful for conjugation to carboxylic acids, aldehydes and ketones. Most often these are synthesized by reaction of an activated ester of a carboxylic acid or a sulfonyl halide with a diamine, such as cadaverine, or with a hydrazine. Alternatively, aromatic amines are commonly synthesized by chemical reduction of a nitroaromatic compound. Amines and hydrazines are particularly useful precursors for synthesis of thiol-reactive haloacetamides or maleimides by standard methods.

Applications and Methods of Use

In one aspect of the invention, the polymer conjugates of the invention are used to directly stain or label a sample so that the sample can be identified or quantitated. For instance, such polymer conjugates may be added as part of an assay for a biological target analyte, as a detectable tracer element in a biological or non-biological fluid; or for such purposes as photodynamic therapy of tumors, in which a polymer conjugated sample is irradiated to selectively destroy tumor cells and tissues; or to photoablate arterial plaque or cells, usually through the photosensitized production of singlet oxygen. In one preferred embodiment, polymer conjugate is used to stain a sample that comprises a ligand for which the conjugated biological substrate is a complementary member of a specific binding pair (e.g. Table 3).

Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biopsies, filaments, biofilms, etc.

Alternatively, the sample is a solid, optionally a smear or scrape or a retentate removed from a liquid or vapor by filtration. In one aspect of the invention, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids. Alternatively, the sample is obtained from an environmental source such as soil, water, or air; or from an industrial source such as taken from a waste stream, a water source, a supply line, or a production lot.

TABLE 3

Representative specific binding pairs

| Antigen | Antibody |
|---|---|
| Biotin | Anti-biotin or avidin or streptavidin or neutravidin |
| IgG* | Protein A or protein G or anti-IgG antibody |
| Drug | Drug receptor |
| Toxin | Toxin receptor |
| Carbohydrate | Lectin or carbohydrate receptor |
| Peptide | Peptide receptor |
| Nucleotide | Complimentary nucleotide |
| Protein | Protein receptor |
| Enzyme substrate | Enzyme |
| DNA (RNA) | aDNA (aRNA)** |
| Hormone | Hormone receptor |
| Psoralen | Nucleic acid |
| Target molecule | RNA or DNA aptamer |
| Ion | Ion chelator |

*IgG is an immunoglobulin;
**aDNA and aRNA are the antisense (complementary) strands used for hybridization In yet another embodiment, the sample is present on or in solid or semi-solid matrix. In one aspect of the invention, the matrix is a membrane. In another aspect, the matrix is an electrophoretic gel, such as is used for separating and characterizing nucleic acids or proteins, or is a blot prepared by transfer from an electrophoretic gel to a membrane. In another aspect, the matrix is a silicon chip or glass slide, and the analyte of interest has been immobilized on the chip or slide in an array (e.g. the sample comprises proteins or nucleic acid polymers in a microarray). In yet another aspect, the matrix is a microwell plate or microfluidic chip, and the sample is analyzed by automated methods, typically by various methods of high-throughput screening, such as drug screening.

The polymer conjugates of the invention are generally utilized by combining a polymer conjugate of the invention as described above with the sample of interest under conditions selected to yield a detectable optical response. The term "polymer conjugate" is used herein to refer to all aspects of the claimed polymer conjugates. The polymer conjugate typically forms a covalent association or complex with an element of the sample, or is simply present within the bounds of the sample or portion of the sample. The sample is then illuminated at a wavelength selected to elicit the optical response. Typically, staining the sample is used to determine a specified characteristic of the sample by further comparing the optical response with a standard or expected response.

A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic.

For biological applications, the polymer conjugates of the invention are typically used in an aqueous, mostly aqueous or aqueous-miscible solution prepared according to methods generally known in the art. The exact concentration of polymer conjugate is dependent upon the experimental conditions and the desired results. The optimal concentration is determined by systematic variation until satisfactory results with minimal background fluorescence are accomplished.

The polymer conjugates are most advantageously used to stain samples with biological components. The sample may comprise heterogeneous mixtures of components (including intact cells, cell extracts, bacteria, viruses, organelles, and mixtures thereof), or a single component or homogeneous group of components (e.g. natural or synthetic amino acids, nucleic acids or carbohydrate polymers, or lipid membrane complexes). These polymer conjugates are generally nontoxic to living cells and other biological components, within the concentrations of use.

The polymer conjugate is combined with the sample in any way that facilitates contact between the polymer conjugate and the sample components of interest. Typically, the polymer conjugate or a solution containing the polymer conjugate is simply added to the sample. Various protocols for cellular staining with polymer conjugates, e.g., antibody polymer conjugate staining for use in flow cytometry, can be employed. Such protocols include protocols for intracellular staining of target antigens of interest inside the cells of the sample with polymer conjugates. Treatments that permeabilize the plasma membrane, such as electroporation, shock treatments or high extracellular ATP can be used to introduce selected polymer conjugates into cells. Alternatively, selected polymer conjugates can be physically inserted into cells, e.g. by pressure microinjection, scrape loading, patch clamp methods, or phagocytosis.

Polymer conjugates that incorporate an aliphatic amine or a hydrazine residue can be microinjected into cells, where they can be fixed in place by aldehyde fixatives such as formaldehyde or glutaraldehyde. This fixability makes such polymer conjugates useful for intracellular applications such as neuronal tracing.

Polymer conjugates that possess a lipophilic substituent, such as phospholipids, will non-covalently incorporate into lipid assemblies, e.g. for use as probes for membrane structure; or for incorporation in liposomes, lipoproteins, films, plastics, lipophilic microspheres or similar materials; or for tracing. Lipophilic polymer conjugates are useful as fluorescent probes of membrane structure.

Using polymer conjugates to label active sites on the surface of cells, in cell membranes or in intracellular compartments such as organelles, or in the cell's cytoplasm, permits the determination of their presence or quantity, accessibility, or their spatial and temporal distribution in the sample. Photoreactive polymer conjugates can be used similarly to photolabel components of the outer membrane of biological cells or as photo-fixable polar tracers for cells.

Optionally, the sample is washed after staining to remove residual, excess or unbound polymer conjugate. The sample is optionally combined with one or more other solutions in the course of staining, including wash solutions, permeabilization and/or fixation solutions, and solutions containing additional detection reagents. An additional detection reagent typically produces a detectable response due to the presence of a specific cell component, intracellular biological substrate, or cellular condition, according to methods generally known in the art. Where the additional detection reagent has, or yields a product with, spectral properties that differ from those of the subject polymer conjugates, multicolor applications are possible. This is particularly useful where the additional detection reagent is a polymer conjugate or polymer conjugate-conjugate of the present invention having spectral properties that are detectably distinct from those of the staining polymer conjugate.

The polymer conjugate conjugates of the invention are used according to methods extensively known in the art; e.g. use of antibody conjugates in microscopy and immunofluorescent assays; and nucleotide or oligonucleotide conjugates for nucleic acid hybridization assays and nucleic acid sequencing (e.g., U.S. Pat. No. 5,332,666 to Prober, et al. (1994); U.S. Pat. No. 5,171,534 to Smith, et al. (1992); U.S. Pat. No. 4,997,928 to Hobbs (1991); and WO Appl. 94/05688 to Menchen, et al.). Polymer conjugate-conjugates of multiple independent polymer conjugates of the invention possess utility for multi-color applications.

At any time after or during staining, the sample is illuminated with a wavelength of light selected to give a detectable optical response, and observed with a means for detecting the optical response. Equipment that is useful for illuminating the polymer conjugates of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors. Preferred embodiments of the invention are polymer conjugates that are be excitable at or near the wavelengths 405 nm.

The optical response is optionally detected by visual inspection, or by use of any of the following devices: CCD cameras, video cameras, photographic films, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

One aspect of the instant invention is the formulation of kits that facilitate the practice of various assays using any of the polymer conjugates of the invention, as described above. The kits of the invention typically comprise a fluorescent polymer conjugate of the invention where the conjugated biological substrate is a specific binding pair member, or a nucleoside, a nucleotide, an oligonucleotide, a nucleic acid polymer, a peptide, or a protein. The kit optionally further comprises one or more buffering agents, typically present as an aqueous solution. The kits of the invention optionally further comprise additional detection reagents, a purification medium for purifying the resulting labeled biological substrate, luminescence standards, enzymes, enzyme inhibitors, organic solvent, or instructions for carrying out an assay of the invention.

EXAMPLES

Examples of some synthetic strategies for selected polymer conjugates of the invention, as well as their characterization, synthetic precursors, conjugates and method of use are provided in the examples below. Further modifications and permutations will be obvious to one skilled in the art. The examples below are given so as to illustrate the practice of this invention. They are not intended to limit or define the entire scope of this invention. It is to be understood that this invention is not limited to particular aspects described, as such may vary. It is also to be understood that the terminology used herein is for the purpose of describing particular aspects only, and is not intended to be limiting since the scope of the present invention will be limited only by the appended claims. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Example 1. The Preparation of Compound 2

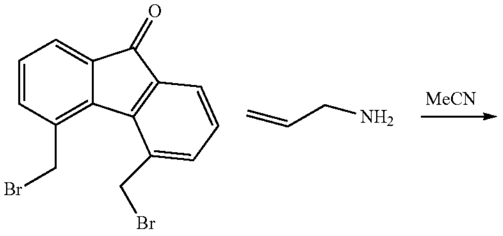

1

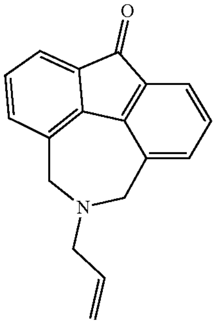

2

Compound 1 (36.6 g, Tianjin Biolite) is suspended in 400 mL MeCN. Allyl amine (30 mL, 4 eq) is added quickly. The mixture is stirred at room temperature for 40 minutes, and concentrated. To the residue is added 10 g $NaHCO_3$ and brine, and the mixture is extracted by DCM three times. The organic layer is collected, dried by $Na_2SO_4$, concentrated and purified by flash chromatography on silica gel to give the product 2 as a yellow solid (21.75 g).

Example 2. The Preparation of Compound 3

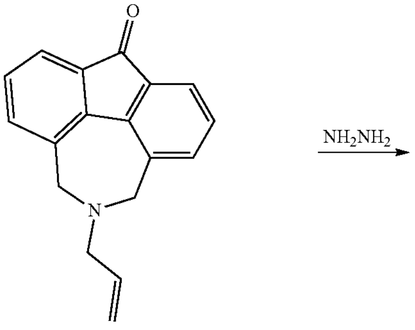

2

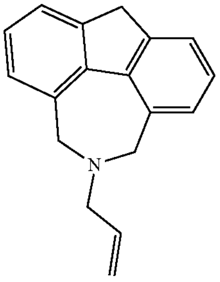

3

Compound 2 (4.7 g) is added to KOH (3 g) solution in diethylene glycol (60 mL). The mixture is heated at 180° C. for 1 hour before being cooled to room temperature and diluted with water. The solid precipitated is collected by filtration and purified by flash chromatography on silica gel to give the product 3 as a pale yellow solid (3.75 g).

Example 3. The Preparation of Compound 4

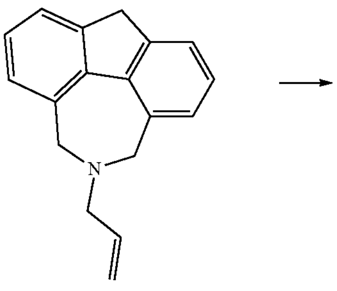

3

-continued

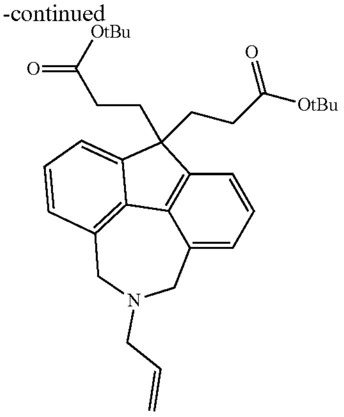

4

To a mixture of Compound 3 (4.94 g) and TBAB (0.644 g, 0.1 eq) is added toluene (50 mL) and 50% NaOH (28 mL) in ice bath. The mixture is stirred under Argon at room temperature for 16 hours before being diluted by icy water. The mixture is extracted by DCM twice. The organic phase is combined and washed by water. The collected solution is dried by $Na_2SO_4$, concentrated and purified by flash chromatography on silica gel to give the product 4 as a yellow orange solid (9.36 g).

Example 4. The Preparation of Compound 5

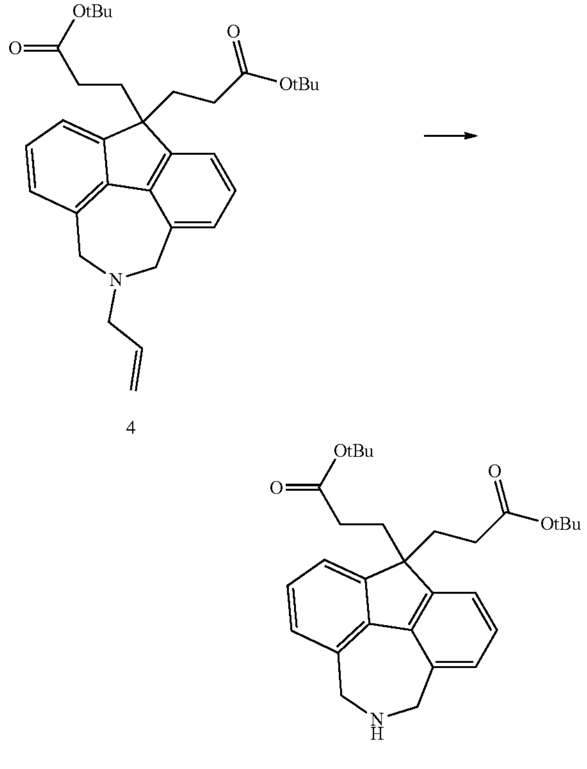

4

5

Compound 4 (9.2 g) is mixed with $Pd(OAc)_2$ (0.205 g, 0.05 eq), $PPh_3$ (1.10 g, 0.23 eq) and 1,3-Dimethylbarbituric acid (8.56 g, 3 eq) in 250 mL DCM. The reaction is stirred at 35° C. for 2 hours. The reaction mixture is washed by $NaHCO_3$ solution and brine, dried by $Na_2SO_4$, concentrated and purified by flash chromatography on silica gel to give the product 5 as a yellow solid (9.44 g).

Example 5. The Preparation of Compound 6

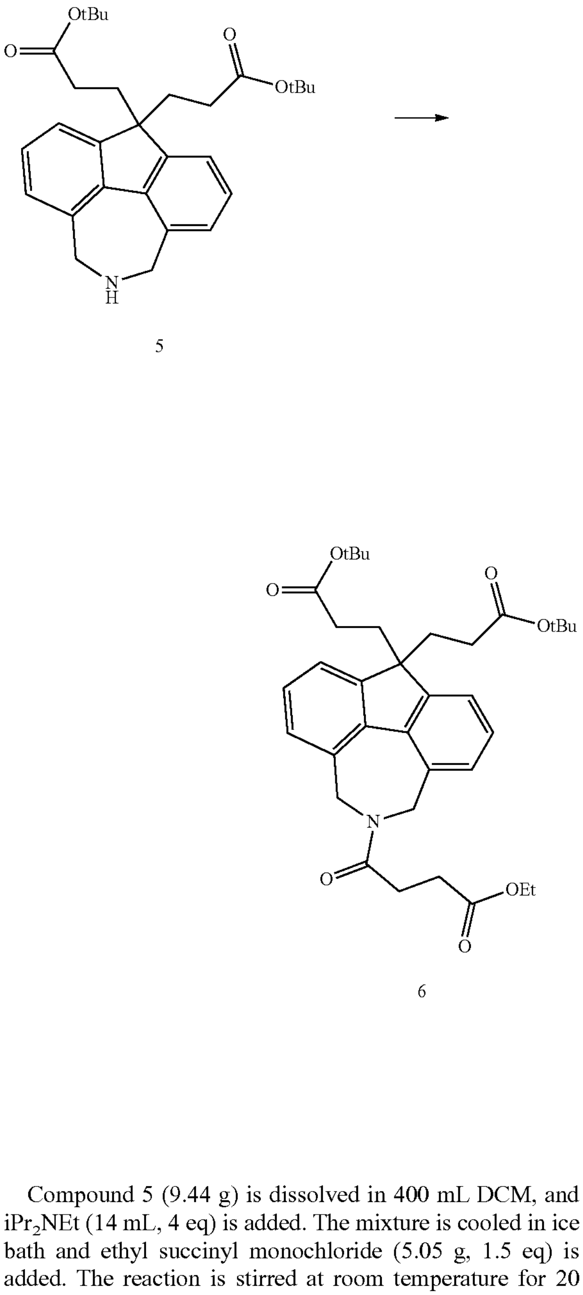

5

6

Compound 5 (9.44 g) is dissolved in 400 mL DCM, and $iPr_2NEt$ (14 mL, 4 eq) is added. The mixture is cooled in ice bath and ethyl succinyl monochloride (5.05 g, 1.5 eq) is added. The reaction is stirred at room temperature for 20 minutes before being quenched with brine. The organic phase is separated, dried by $Na_2SO_4$, concentrated and purified by flash chromatography on silica gel to give the product 6 as a yellow brown solid (9.83 g).

Example 6. The Preparation of Compound 7

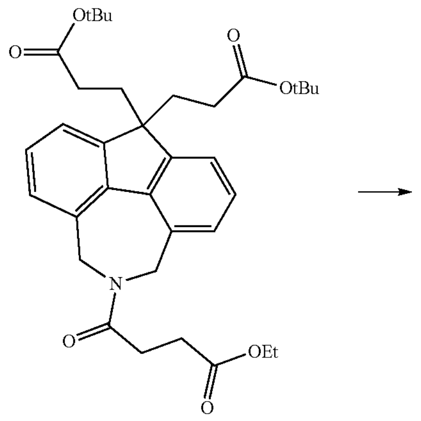

6

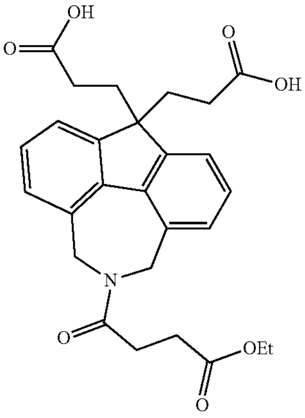

7

Compound 6 (9.8 g) in 30 mL DCM is added 15 mL TFA. The reaction is stirred at room temperature for 1.5 h. The mixture is concentrated, azeotroped with DCM, tolune and finally hexane and DCM to give product 7 (7.32 g) as a yellow solid.

Example 7. The Preparation of Compound 8

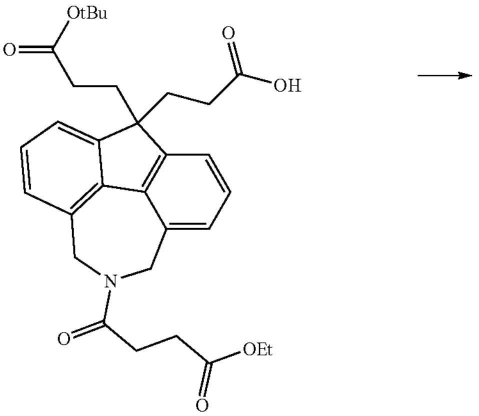

7

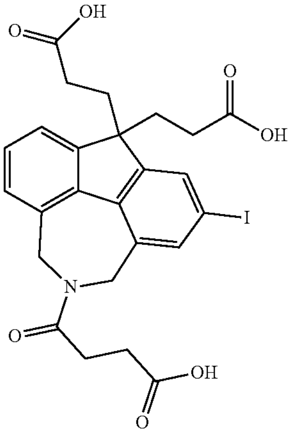

8

Compound 7 (2.93 g) is dissolved in 20 mL AcOH. Iodine (0.6 g, 0.4 eq), $KIO_3$ (0.32 g, 0.24 eq) and 2.5 mL 33% $H_2SO_4$ are added. The reaction is stirred at 50° C. for 4.5 hours before being diluted with water. 25 mL $NaHCO_3$ (saturated) is added to give a solution, which is purified by reverse phase HPLC C18 column and lyophilized to give the product 8 (1.95 g).

Example 8. The Preparation of Compound 9

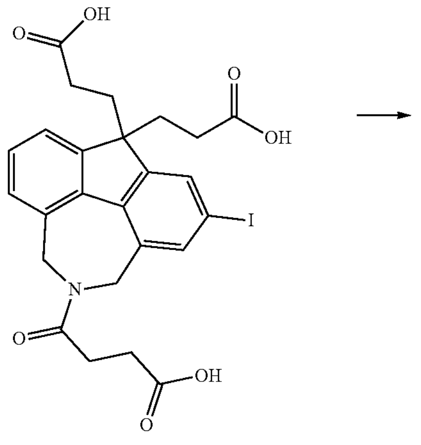

8

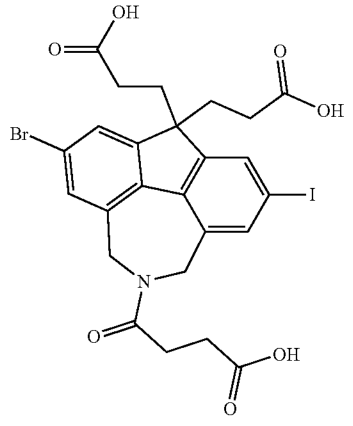

9

Compound 8 (1.95 g) is dissolved in 20 mL DMF, and added 0.15 mL bromine (2 eq). The mixture is stirred at room temperature for 30 hours. The reaction is quenched with $Na_2SO_3$ solution. $NaHCO_3$ (saturated, 25 mL) is added to give a solution, which is purified by reverse phase HPLC C18 column and lyophilized to give the product 9 (1.8 g).

Example 9. The Preparation of Compound 10

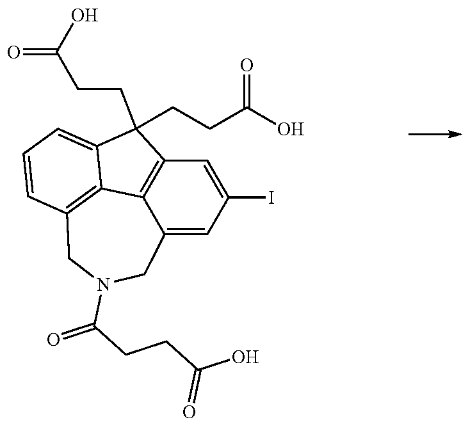

9

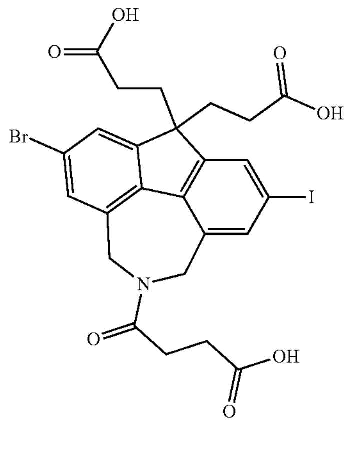

10

At 0° C., to the mixture of compound 9 (1.8 g) in THE (20 mL), $Et_3N$ (1.4 mL, 6 eq) is added, followed by ethyl chloroformate (0.63 mL, 4 eq) dropwise. The mixture is stirred at room temperature for 30 min. The white precipitate is filtered, and the filtrate is concentrated. After drying for 1 hour under high vacuum, at 0° C., THF (20 mL) is added, followed by sodium borohydride (0.37 g, 6 eq) in water (2 mL) dropwise. The mixture is stirred at 0° C. for 30 min. The reaction is quenched with $NH_4Cl$ solution. More $H_2O$ is added to dissolve all the precipitate. The mixture is concentrated to remove the THE and extracted with EtOAc (3×50 mL) until no product is in the water layer. The organic phase is dried by $Na_2SO_4$, concentrated and purified by flash chromatography on silica gel to give the product 10 as a white solid (1 g).

Example 10. The Preparation of Compound 11

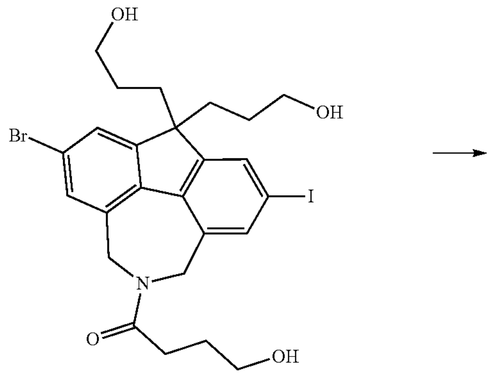

10

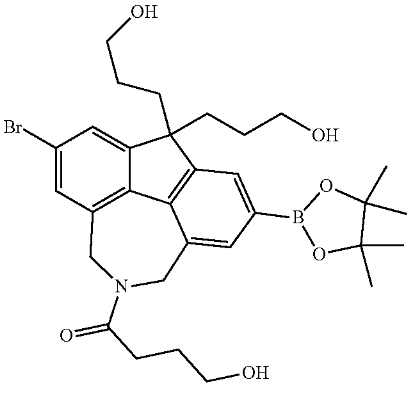

11

Compound 10 (1.0 g) is dissolved in 10 mL DMF and bis(pinacolato)diboron (0.413 g, 1.4 eq) is added, followed by $Pd(dppf)Cl_2$ (0.04 g, 0.05 eq) and potassium acetate (0.47 g, 4 eq). The mixture is degassed with Argon for 10 min. The reaction is stirred at 80° C. for 2 hours. At room temperature, EtOAc (100 mL) is added and quenched with brine. The organic phase is separated, dried by $Na_2SO_4$, concentrated and purified by flash chromatography on silica gel to give the product 11 as a light brown solid (0.9 g).

Example 11. The Preparation of Compound 12

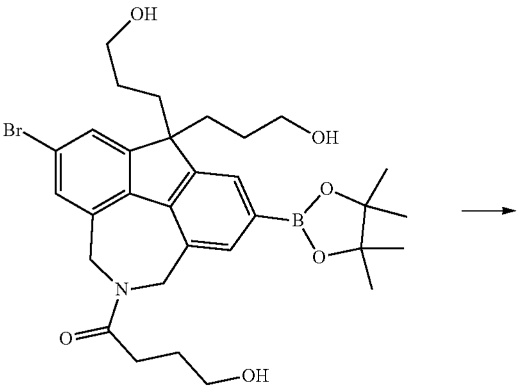

11

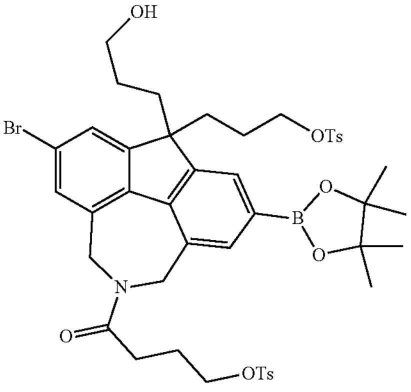

12

Compound 11 (0.9 g) is dissolved in THE (10 mL), $Et_3N$ (1.22 mL, 6 eq) is added, followed by TsCl (1.12 g, 4 eq). The reaction is stirred at room temperature for 18 hours. The mixture is concentrated and purified by flash chromatography on silica gel to give the product 12 as a light brown solid (1.5 g).

Example 12. The Preparation of Compound 13

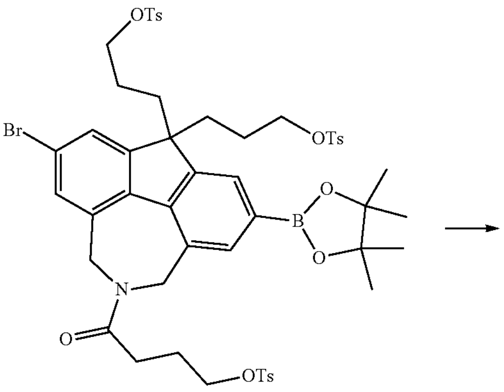

12

-continued

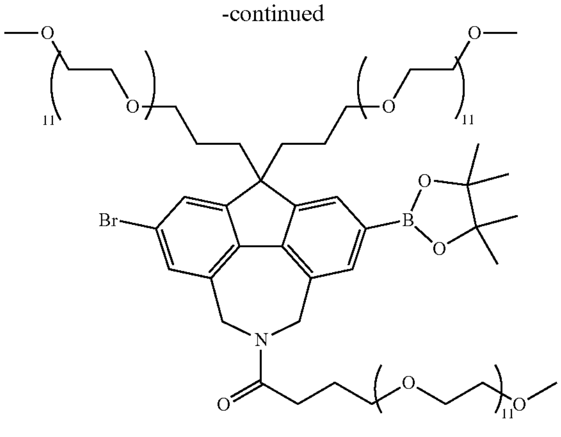

13

At 0° C., to the mixture of NaH (0.33 g, 6 eq) in dry THE (40 mL), $PEG_{11}$-OH (4.34 g, 6 eq) is added. After 10 min at 0° C., the solution of Compound 12 (1.5 g) in dry THE (20 mL) is added dropwise. The reaction is stirred at room temperature for 18 hours. The mixture is concentrated and chloroform (100 mL) is added. The organic phase is washed by $H_2O$ (100 ml), separated, dried by $Na_2SO_4$, concentrated and purified by flash chromatography on silica gel to give the product 13 as a colorless liquid (3 g).

Example 13. The Preparation of Compound 14

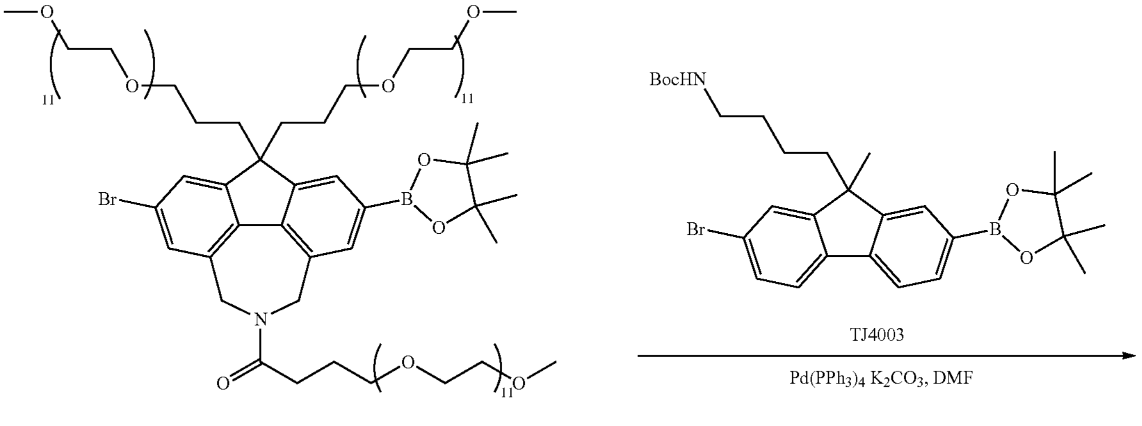

13

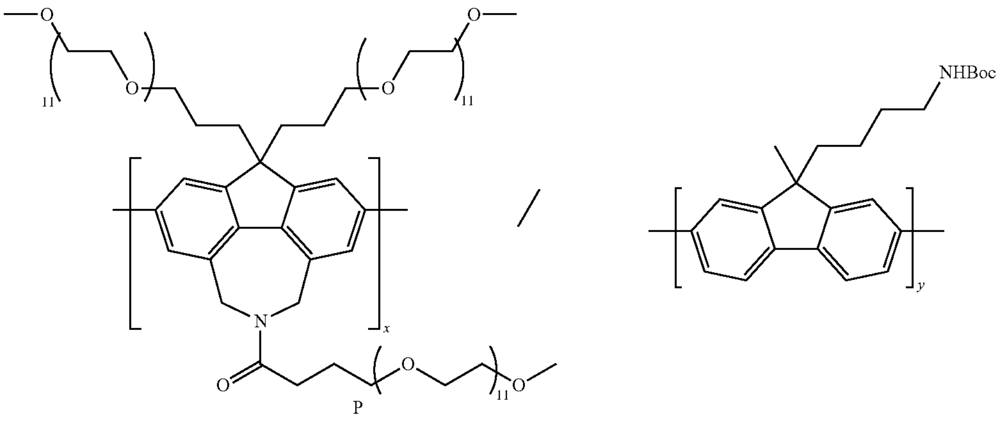

14

Under the argon, to the solution of Compound 13 (0.8 g) and Compound TJ4003 (0.029 g, Tianjin Biolite) in DMF (6 mL) in a Schlenk flask, $K_2CO_3$ in water (2 M, 4 mL) is added, followed by palladium tetrakis(triphenylphosphine) (0.015 g, 0.03 eq). The mixture is degassed via three freeze-pump-thaw cycles, and heated to 80° C. for 4 hours. At room temperature, to the reaction mixture, phenylboronic acid pinacol ester (0.043 g, 0.1 eq) is added under the argon, and heated to 80° C. for 2 hours. At room temperature, to the reaction mixture, EDTA (0.1 g) in 20% EtOH/$H_2O$ (20 mL) is added and stirred at room temperature for 2 hours. The resulting mixture is filtered through a 0.45 μm cup filter. The filtered solution is diluted to the concentration of 2 mg/mL using 20% EtOH/$H_2O$. The resulting dilution is dialyzed into 20% EtOH/$H_2O$ using a tangential flow filtration system with 30 kD and 750 kD molecular weight cutoff membrane until there is less than 0.1 mg/mL of polymer in the elutant. The solution is concentrated and lyophilized to give Compound 14 (0.5 g) as a yellow semi-solid.

Example 14. The Preparation of Compound 15

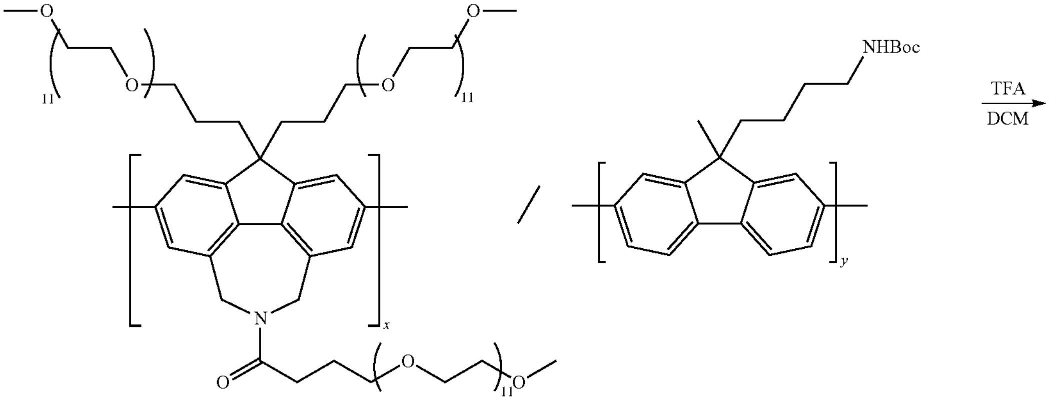

14

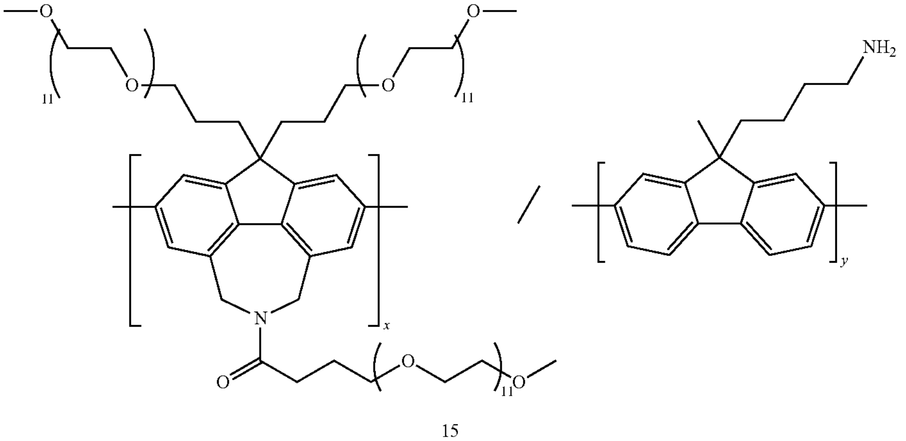

15

At room temperature, to the solution of Compound 14 (500 mg) in dichloromethane (13 ml), trifluoroacetic acid (7 mL) is added, followed by anisole (0.08 mL). The reaction mixture is stirred at room temperature for 2-3 hours. The solvent is removed and dried under high vacuum overnight to give Compound 15 (400 mg) as pale yellow oil.

Example 15. The Preparation of Compound 16

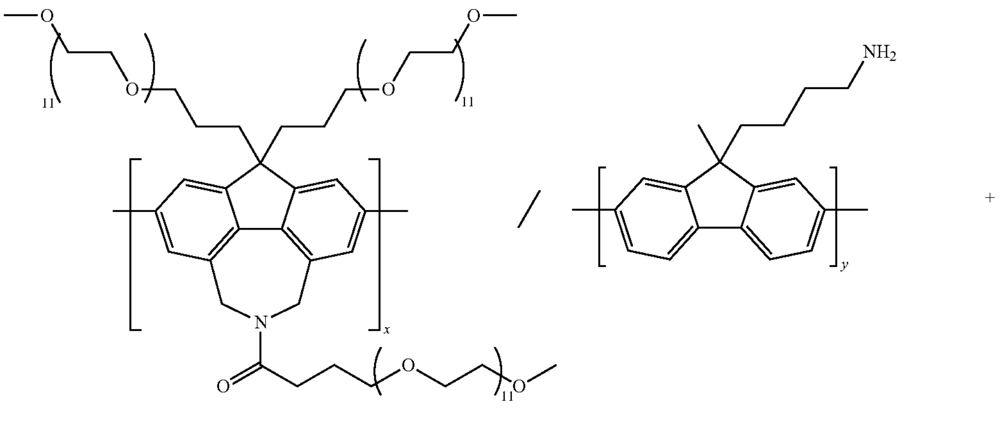

15

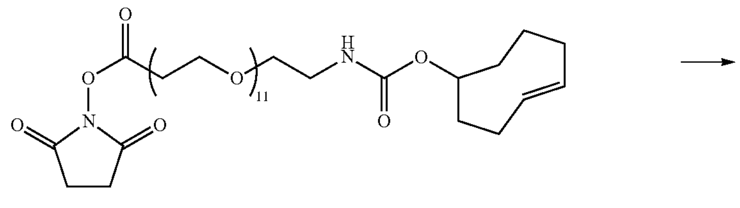

TJ4100

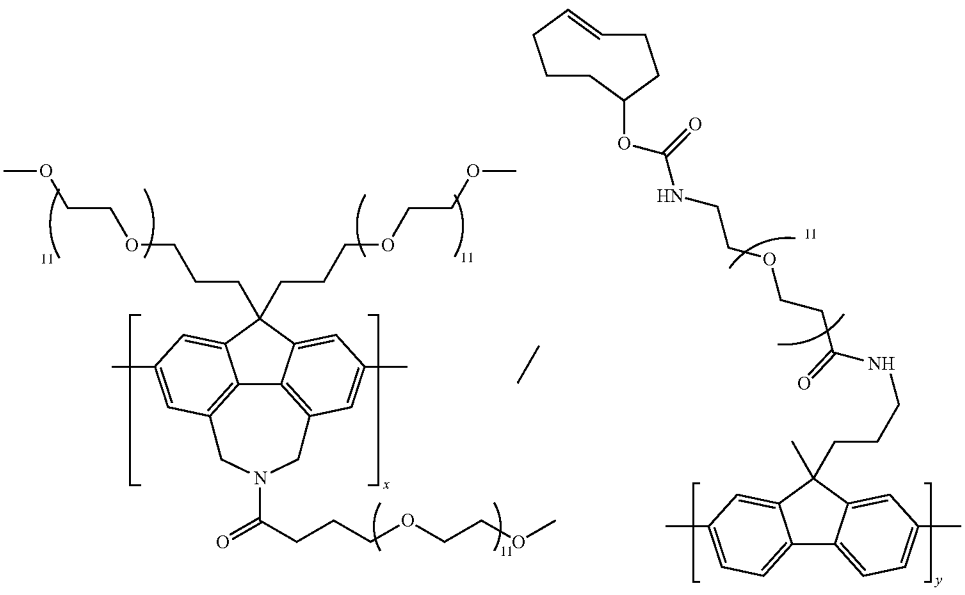

16

At room temperature, to the solution of Compound 15 (120 mg) in DMF (3 mL), triethylamine (0.033 mL) is added, followed by TJ4100 (2.1 mg, Tianjin Biolite). The mixture is stirred at room temperature for 1-2 hours. Ice water (3-6 g) is added to quench the reaction. The mixture is purified by P6DG column chromatography (water as solvent) to give a yellow solution. The final product 16 is aliquoted according to the extinction coefficient.

Example 16. The Preparation of Fluorene Polymer Succinimidyl Ester (Compound 17)

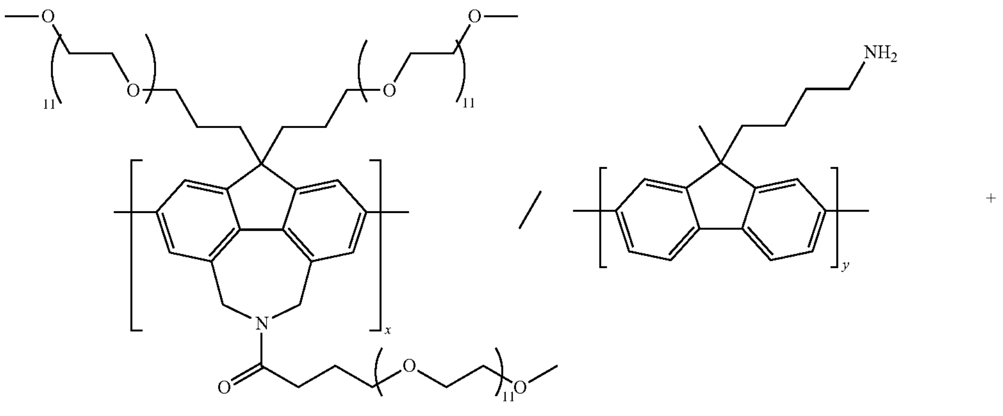

15

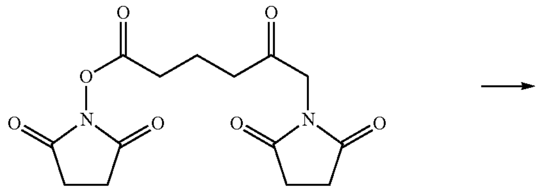

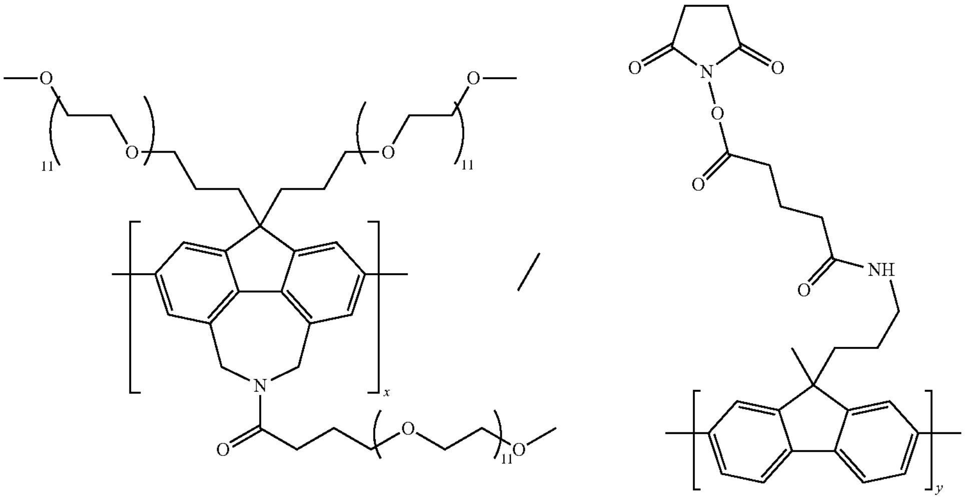

17

To the solution of Compound 15 (100 mg) in DMF (10 ml) is added 0.1 ml DMF solution of di(N-succinimidyl) glutarate (1 mg, AAT Bioquest) and 10 μl triethylamine. The reaction mixture is stirred at room temperature for 2 hours, and concentrated under high vacuum to remove DMF. The residue is washed with ether for multiple times until most of the unreacted di(N-succinimidyl) glutarate is removed. The residue is quickly dissolved in cold acidic water (pH=5), and extracted with ether for three times. The aqueous solution is frozen and dried to give the desired fluorene polymer succinimidyl ester as Compound 17.

Example 17. The Preparation of Fluorene Polymer Maleimide (Compound 18)

To the solution of Compound 15 (100 mg) in DMF (10 ml) is added 0.1 ml DMF solution of 3-maleimidopropionic acid N-hydroxysuccinimide ester (1 mg, AAT Bioquest) and 10 μl triethylamine. The reaction mixture is stirred at room temperature for 2 hours, and concentrated under high vacuum to remove DMF. The residue is dissolved in acidic water (pH=5), and extracted with ethyl acetate for three times. The aqueous solution is frozen and dried to give the desired fluorene polymer maleimide as Compound 18.

The above examples of some synthetic strategies for the selected polymers of the invention, as well as their characterization, synthetic precursors, conjugates and methods of use are provided in the examples for illustration. Their further modifications and permutations are obvious to one skilled in the art. For example, the second fluorophores (such as Cy3.5, Cy5, TAMRA and Texas Red in the above examples) conjugated to the polymers of the invention can be readily replaced with the commercial dyes listed in Table 1 to make the polymers have the different desired spectral properties. In addition, the polymers of the invention can be further functionalized with a different reactive functional group pairs as listed in Table 2. The well-known click-reactive groups can also be added to the polymers of the invention for the biorthogonal chemistry-based conjugations (see P. Agarwal and R. Bertozzi, Bioconjugate Chem., 2015, 26, 176-192; K. Lang and J. Chin, Chem. Reviews, 2014, 114, 4764-4806; M. D. Best, Biochemistry, 2009, 48, 6571-6584). Some other alternative methods for polymer functionalization were well described in the literature (see U.S. Pat. Nos. 8,158,444; 8,455,613; 8,354,239; 8,362,193; and 8,575,303 to Gaylord, et al.; also WO 2013/101902 to Chiu et al).

Example 18. Preparation of Goat Anti-Mouse IgG-Fluorene Polymer Dye Conjugates

Goat Anti-Mouse IgG (GAM) is dissolved in 10 mM $NaHCO_3$ (pH 8.2) buffer to make a 5 mg/mL solution. To the aqueous GAM protein solution is added to the DMF solution of Compound 17 (20 equivalents). The solution is rotated at room temperature for 3 hours and the reaction mixture is transferred to an Amicon Ultra filter (MWCO=10 kDa) to remove DMF. The protein is recovered into the initial volume with PBS buffer.

Cation exchange chromatography is used to remove free polymer. Conjugation mixture is loaded to UNOsphere™ S resin (Bio-Rad) in low salt buffer [50 mM MES Buffer (pH=5.0)], and incubated at room temperature for 10 minutes, repeatedly loading the sample for 3 times to get the maximum binding. After loading, the medium is washed with low salt buffer to the baseline (until the absorbance at 414 nm is lower than 0.01) to remove all free polymer. The retained fluorene polymer dye-GAM conjugate on the cation exchange resin is released by elevating both the pH and ionic strength with high salt phosphate buffer [10 mM phosphate buffer (pH=7.4)+1.0M NaCl buffer/methanol, 90/10]. Protein A and Protein G affinity resins can also be used to remove free polymer with comparable results. A HiTrap Protein G HP 1 mL column (GE Lifesciences) is pre-equilibrated with 10 mM Phosphate buffer, pH 7.4, and the SEC-purified product is slowly injected at <1 mg/mL and allowed to incubate for 30 minutes to bind. The column is washed with >10 column volumes of 10 mM Phosphate buffer to wash unbound polymer material off while monitoring absorption of the eluate at 280 nm and 414 nm to ensure all excess material is removed. The conjugate is eluted by washing the column with 4 column volumes of 0.1 M Glycine pH 2.3. The eluted fractions were combined and pH-adjusted back to neutral using 1 M Tris pH 8. After free polymer is removed, the conjugate solution is concentrated with Amicon Ultra Filter (MWCO=30 kD) and loaded to a size exclusion column (Superdex 200, GE life sciences) to separate conjugated and unconjugated antibody. The column is equilibrated with PBS buffer, and the fluorene polymer-antibody conjugate is eluted before free antibodies.

For effective labeling, the degree of substitution should fall between 1-3 moles of fluorene polymer dye to one mole of antibody for most antibodies. As is well known in the art, the optimal ratio of polymer dye/protein depends on the properties of antibody to be labeled. The optimal labeling ratio of polymer dye/protein is determined empirically by preparing a series of dye-conjugates over a range of ratio of polymer dye/protein and comparing the desired signal/background. In some cases, a higher ratio of polymer dye/protein may provide bright signal while in other cases higher ratio of polymer dye/protein could reduce the affinity of the antibody to be labeled.

Example 19. Fluorene Polymer Conjugates for Use in Flow Cytometry

Analyte-specific antibodies conjugated to a fluorene polymer dye of the present invention (i.e, labeled antibodies) are useful for the analysis of blood cells (for example, in whole blood samples) by flow cytometry. The labeled-antibodies were used to stain cellular proteins, and the labeled cells were detected using a flow cytometer. Fluorene polymer bioconjugates were evaluated by Stain Index, as defined by BD Biosciences on a flow cytometer. See, e.g., H. Maeker and J. Trotter, BD Biosciences Application Note: "Selecting Reagents for Multicolour Flow Cytometry", September 2009. The stain index reports a measure of the polymer's brightness, nonspecific binding. Flow cytometry provides a method through which to measure cells of a specific phenotype or analytes of interest on specific microspheres. This can be done with direct labeling of a primary antibody or, if signal amplification is desired, through a secondary antibody or the avidin-biotin complexation with avidin-polymer conjugates. Cells of interest were taken up in sufficient quantity, spun down, washed in DPBS+0.2% BSA and 0.05% $NaN_3$, then resuspended in staining buffer of Fluorene polymer conjugates.

For primary incubation, cells were incubated with a primary conjugate specific to an antigen of interest, negative cells served as a negative non-specific binding reference. A control population or an established commercial conjugate was used as a positive control. Primary antibody-polymer conjugates were incubated at concentrations with volume dilutions from 10-500 nM for 30 minutes.

For secondary antibody labeling, an unlabeled primary antibody to the antigen of interest was incubated at 1-50 μg/ml, or other titrated amount. Following primary incubation, cells were rinsed with 5 volumes staining buffer and spun down for 3-5 minutes. Species reactive secondary fluorene polymer conjugates were incubated at concentrations with volume dilutions from 10-500 nM for 30-60 minutes. Following secondary incubation, cells were rinsed with 3-5 volumes staining buffer and spun down for 3-5 minutes. Cells were resuspended for testing in DPBS+0.2% BSA, 0.05% sodium azide.

For streptavidin-polymer conjugate labeling, cells were incubated with a biotinylated primary antibody to the marker of interest, as detailed above for the secondary antibody labeling, instead of an unlabeled primary. Following the primary washing, cells were resuspended and incubated with streptavidin-polymer conjugates at 1-100 nM volume dilutions for 30 minutes. Following secondary incubation, cells were rinsed with 5 volumes staining buffer and spun down for 3-5 minutes. Cells were resuspended for testing. If further signal amplification was desired, cells could be incubated with an unlabeled primary antibody and then subsequently followed with a species reactive biotinylated secondary antibody prior to incubation with streptavidin conjugates.

It will be understood that the particular antibody conjugate used and the specific reaction components and particular reaction conditions used can have an effect on the results obtained. Routine experimentation should be carried out to determine preferred reaction components, such as buffers or lyse solutions, and reaction conditions, including staining times and temperatures. Such routine optimization of assay conditions is standard practice in the field of immunostaining-based assays.

Example 20. MTA-Modification (Amine)

Antibody was dissolved at 10 mg/mL in 0.1 M Sodium Bicarbonate pH 8.5, and 1 mg antibody in solution was transferred to a microcentrifuge vial. Tetrazine succinimidyl was dissolved at 10 mg/mL in anhydrous DMSO and 1.08 uL was added to the antibody solution at room temperature. The reaction mixture was vortexed briefly to mix, and then placed on the vortex shaker at low speed to react for 1 hour. At the end of 1 hour, the modified antibody was purified from free tetrazine succinimidyl by desalting over a PD-10 column into a 3 mM Phosphate Buffer, 35 mM NaCl pH 7.4 and collected into an Amicon Ultra-4 30 k molecular weight concentrator and concentrated down to >5 mg/mL. The modified antibody was stored at 4° C. until conjugation.

Example 21. MTA-Modification (Sulfhydryl)

Antibody was dissolved at 10 mg/mL in 10 mM Phosphate Buffer, pH 7.4 and 1 mg of antibody in solution was transferred to a microcentrifuge vial. The antibody was reduced by adding 1 mL of a 1M Dithiothreitol (DTT) solution, vortexing briefly and allowing to sit for 30 minutes at room temperature. The solution was then de-salted to remove the DTT over a PD-10 column (GE Lifesciences) into 3 mM Phosphate buffer, pH 7.4. The de-salted reduced antibody was then concentrated over a 30 kDa concentrator (Millipore Amicon Ultra) to 10 mg/mL. To the reduced antibody solution was added 2.3 mL of a 10 mg/mL maleimide-MTA solution in DMSO. The solution was vortexed briefly and placed onto a vortex shaker to react for 90 min at RT. After 90 minutes, the modified antibody was purified from free Maleimide-MTA by desalting over a PD-10 column into a 3 mM Phosphate Buffer, 35 mM NaCl pH 7.4 and collected into an Amicon Ultra-4 30 k molecular weight concentrator and concentrated down to >5 mg/mL. The modified antibody was stored at 4° C. until conjugation.

Example 22. Bioorthogonal Polymer-Antibody Conjugation

Cyclooctene-reactive polymer was stored at 5 mg/mL in DI H2O at −20° C. and thawed immediately before use. MTA-modified antibody (1 mg, 0.167 mL) was transferred to a microcentrifuge vial containing 0.104 mL of 3 mM Phosphate buffer, pH 7.4. Polymer solution (0.133 mL, 0.67 mg polymer) was added to the followed by the addition of ethanol (0.1 mL). The solution was mixed rapidly by pipette. The reaction mixture was placed onto a vortex shaker to react at room temperature for 2 hours, protected from the light. After 2 hours, the reaction mixture was quenched by the addition of 6.7 mL of a 10 mM cyclooctene-quencher and allowed to shake for another 10 minutes before purification.

Example 23. Size Exclusion (SEC) Purification

Figure 2B:
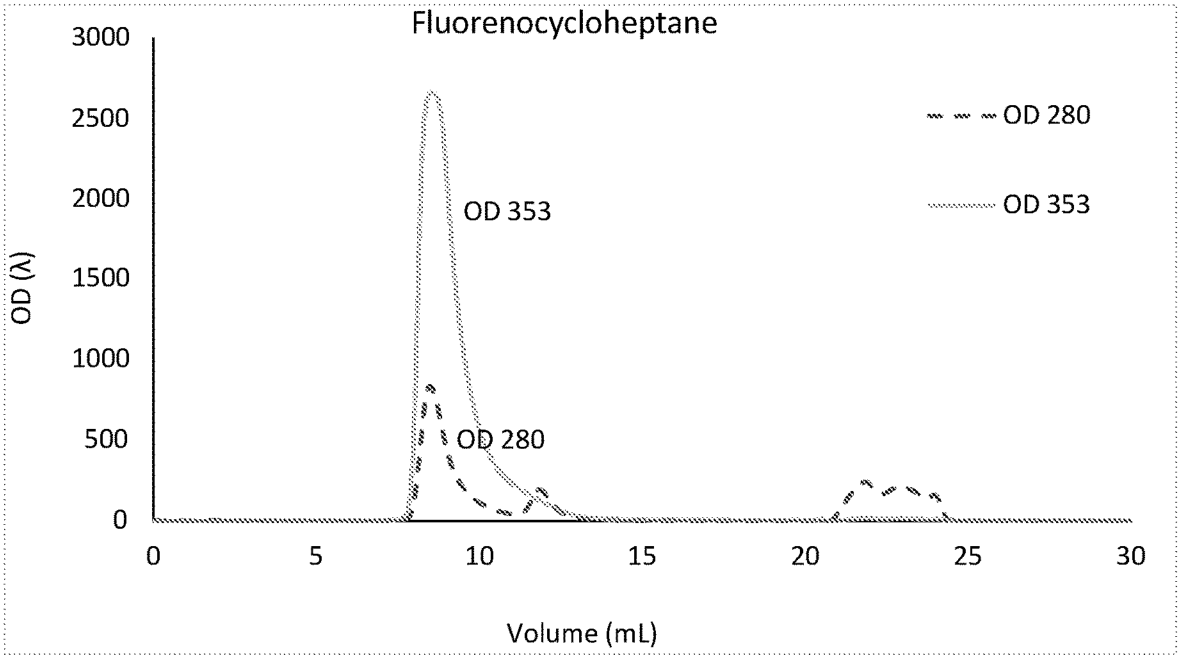
Figure 2C:
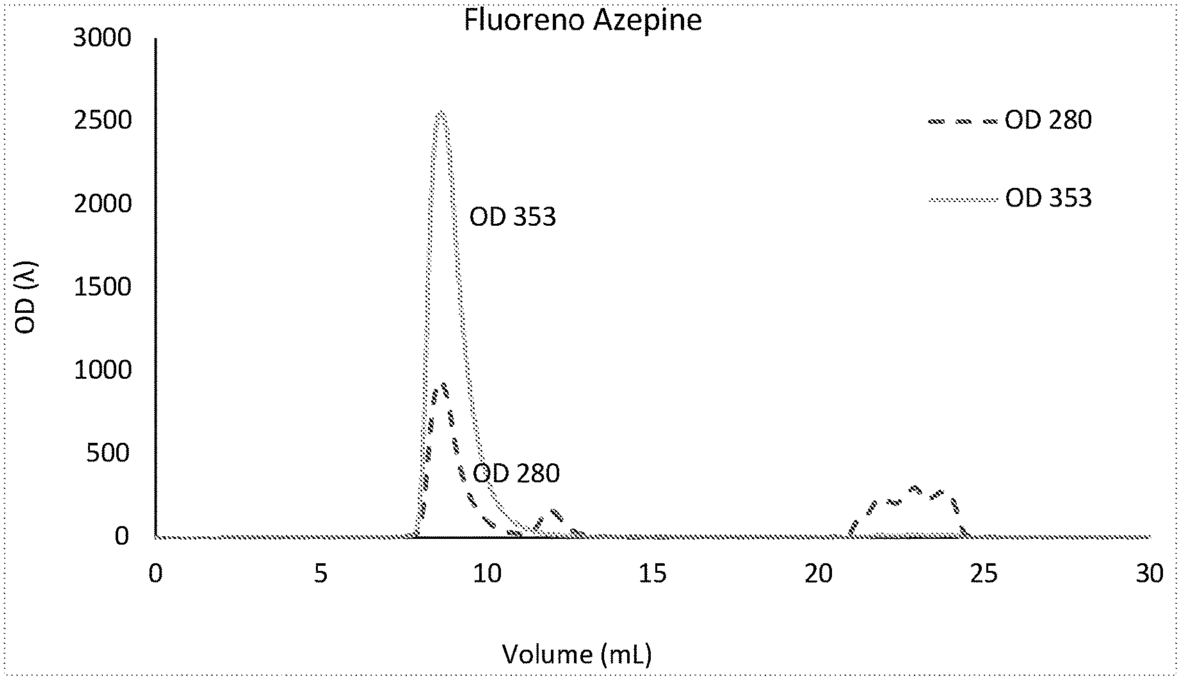
Figure 3A:
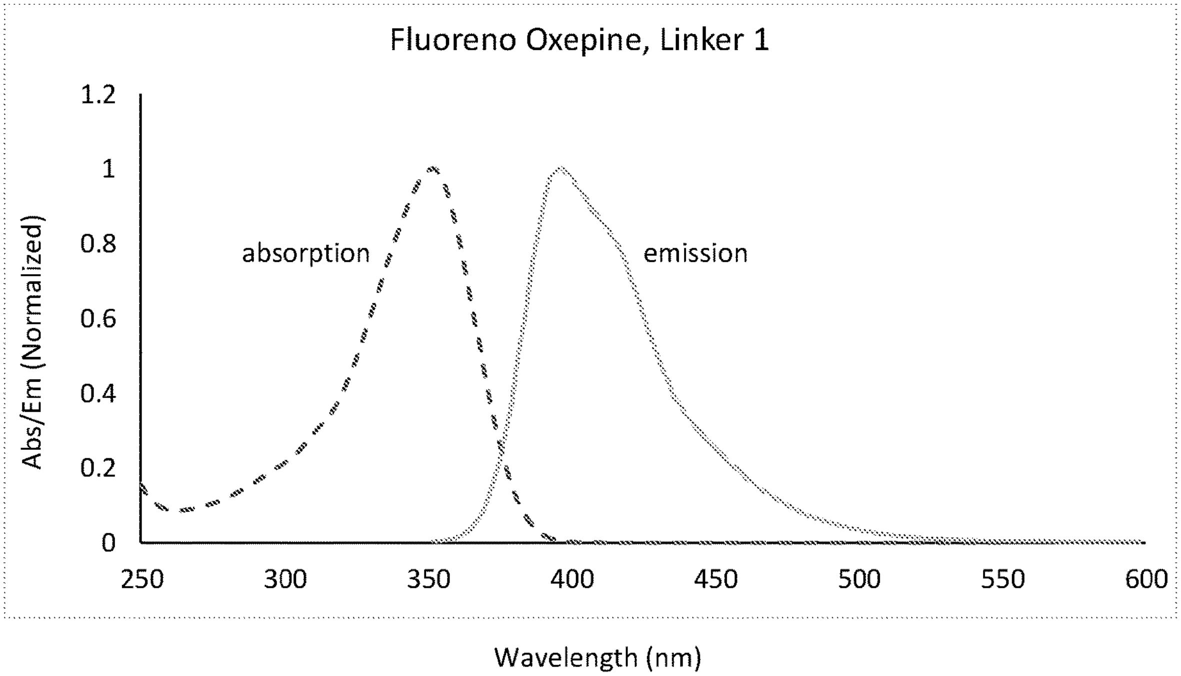
FIGS. 3A-3B. Optical properties of the fluoreno oxepine foundation polymer, with phenyl-based linker attachment.
Figure 3B:
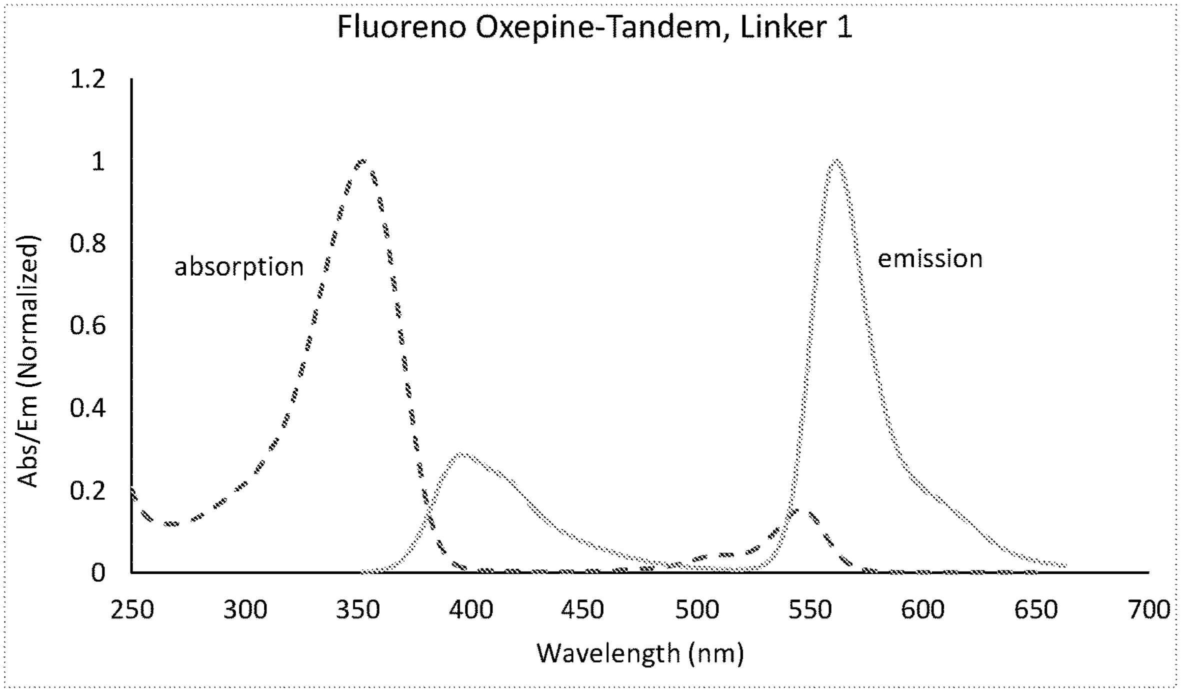
Figure 4A:
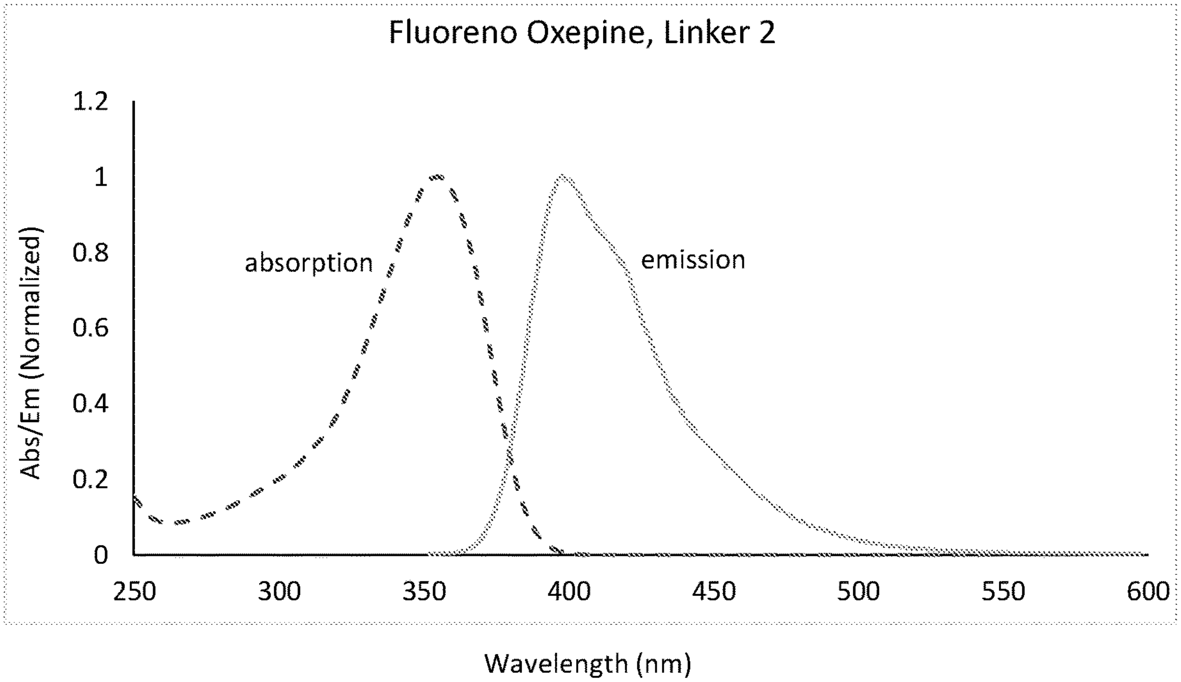
FIGS. 4A-4B. Optical properties of the fluoreno oxepine foundation polymer, with azepine monomer-based linker attachment.
Figure 4B:
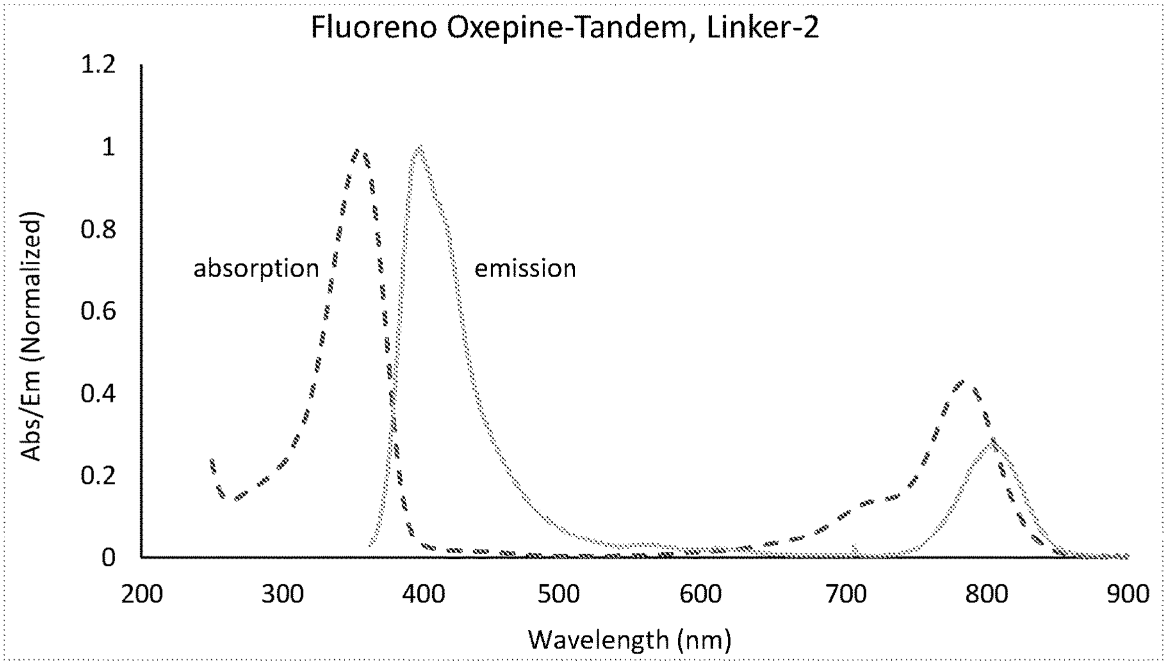
Figure 5A:
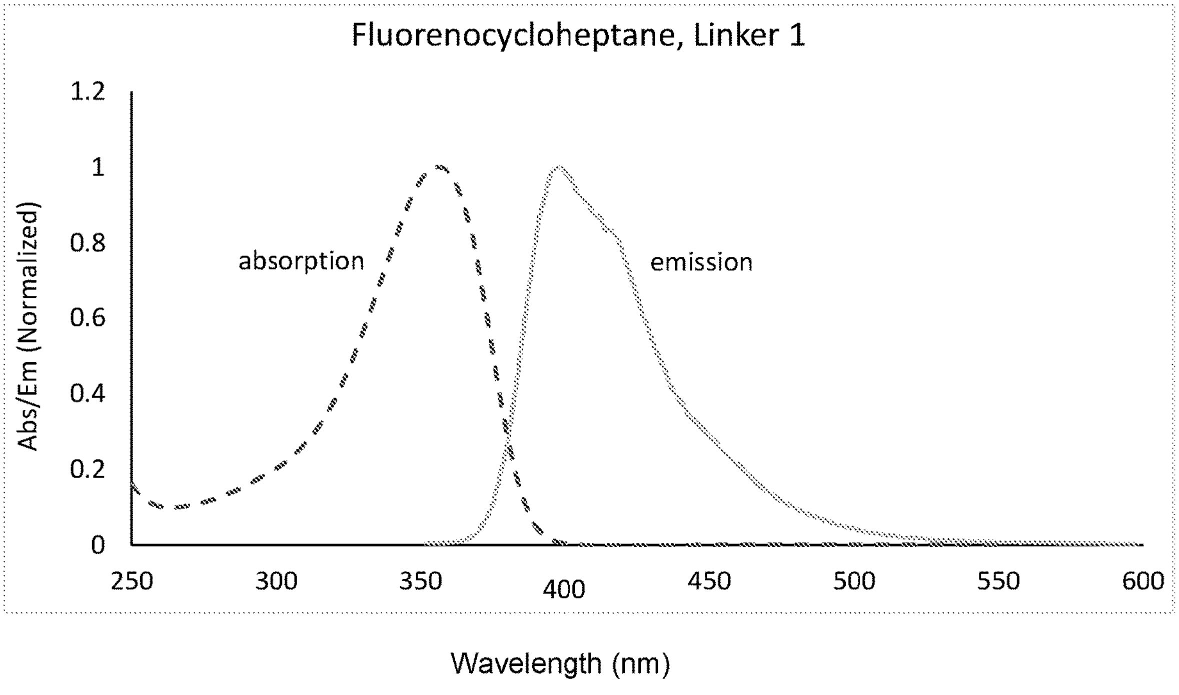
FIGS. 5A-5B. Optical properties of the fluorenocycloheptane foundation polymer, with azepine monomer-based linker attachment.
Figure 5B:
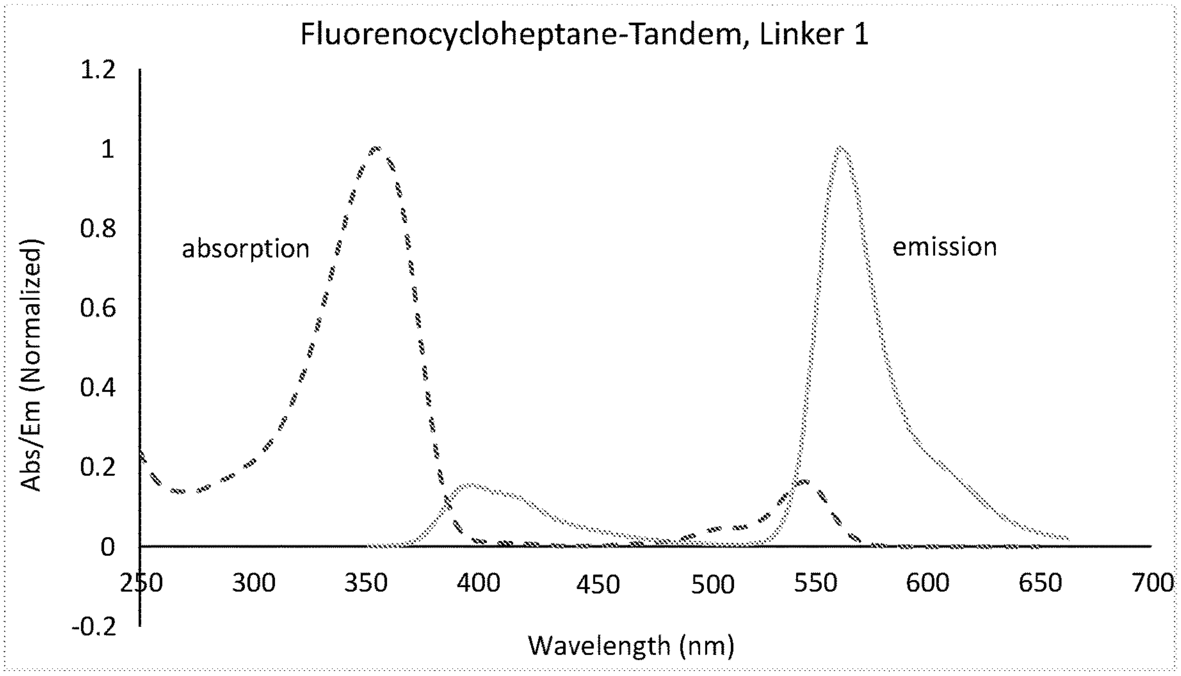
Figure 6A:
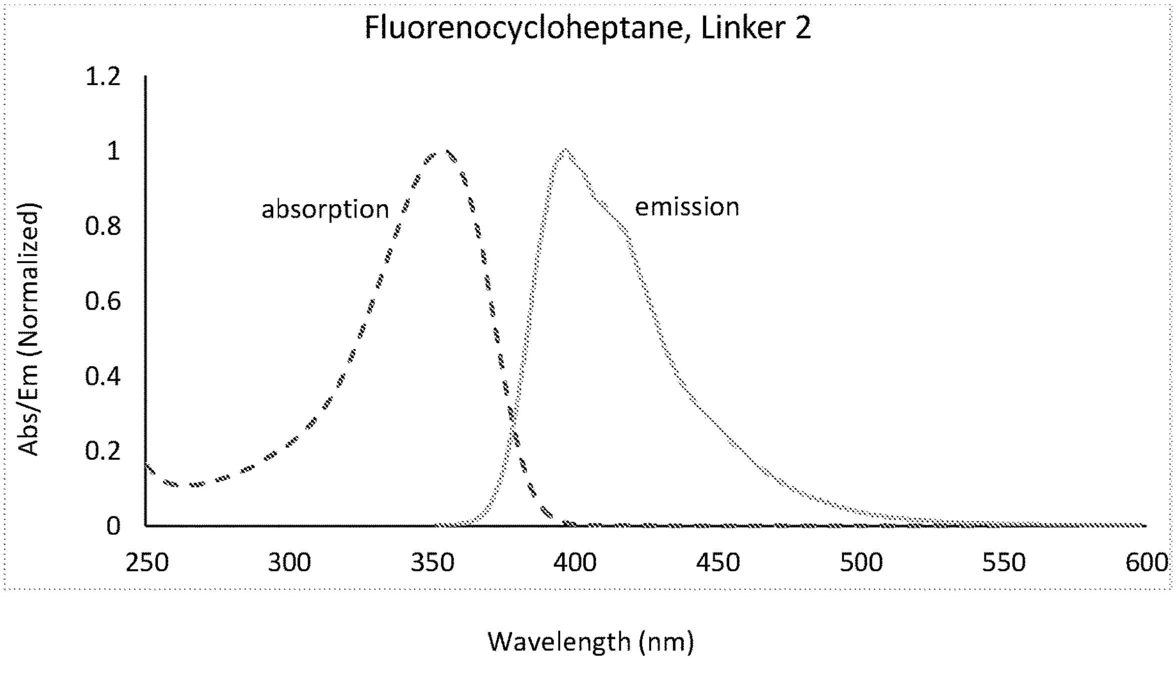
FIGS. 6A-6B. Optical properties of the fluorenocycloheptane foundation polymer, with phenyl-based linker attachment.
Figure 6B:
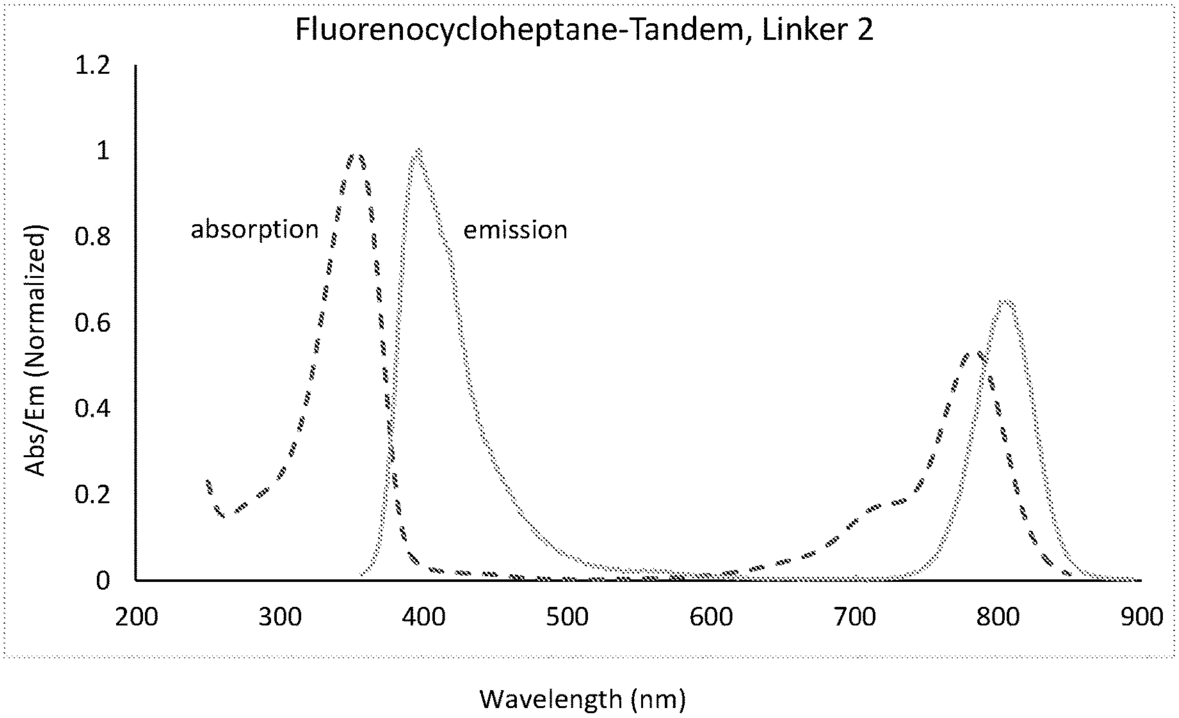
Figure 7A:
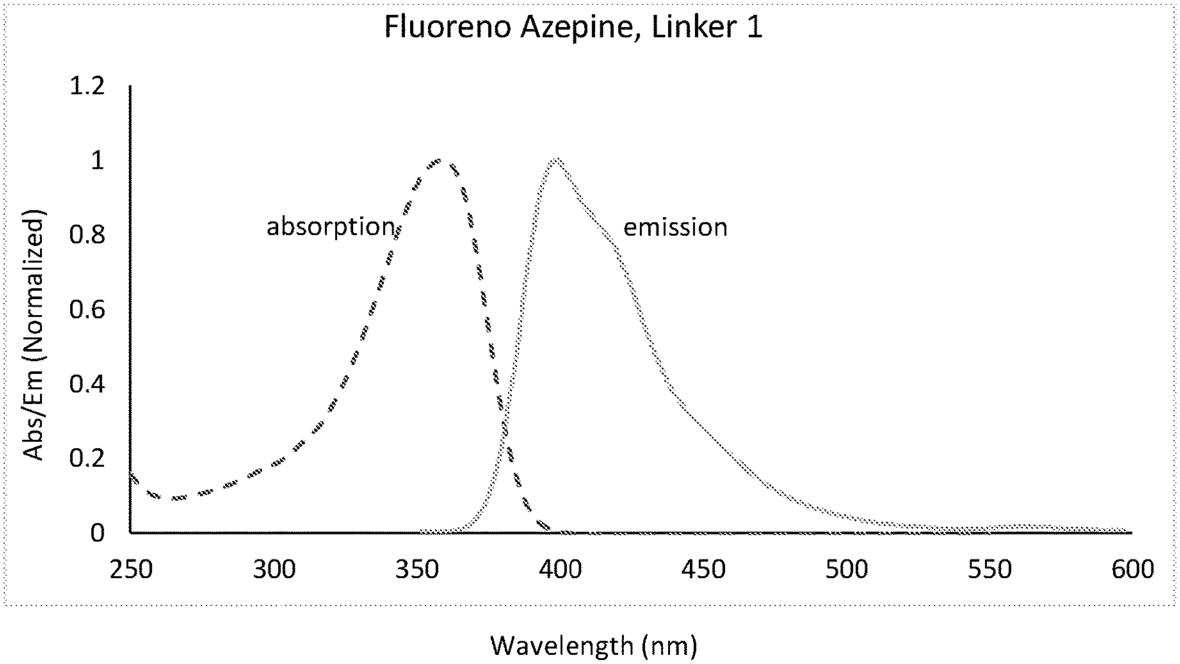
FIGS. 7A-7B. Optical properties of the fluoreno azepine foundation polymer, with azepine monomer-based linker attachment.
Figure 7B:
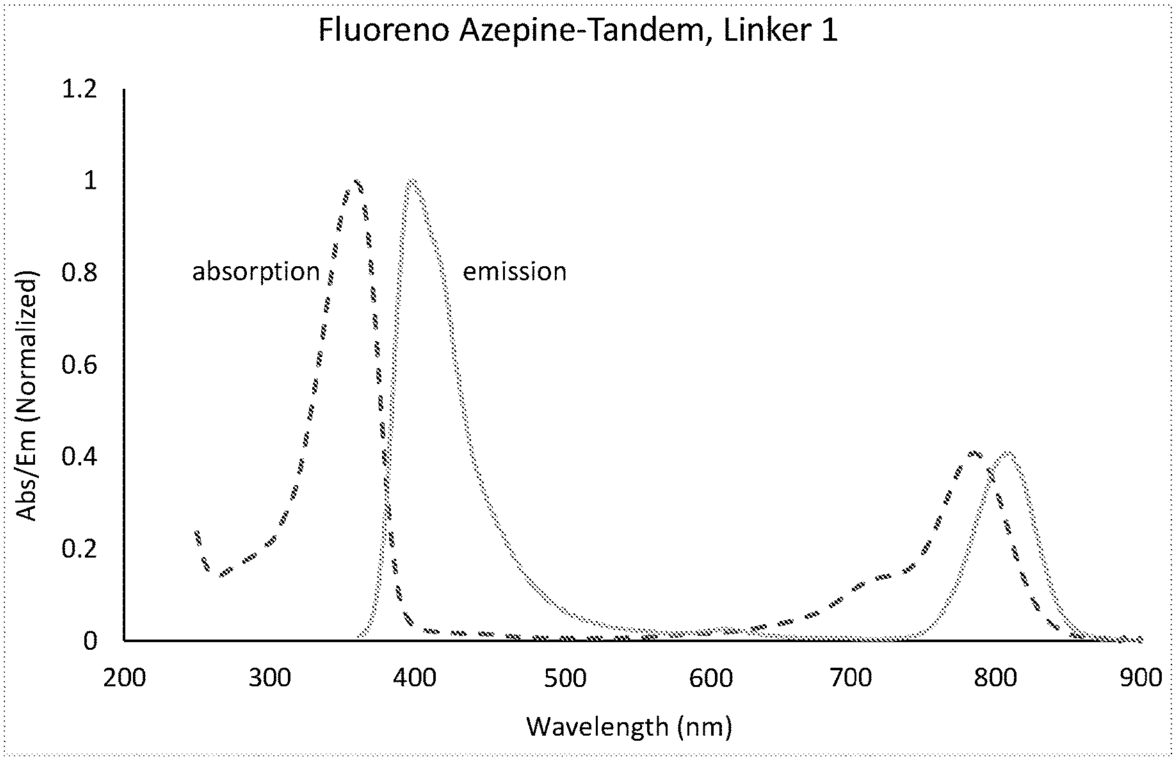
Figure 8A:
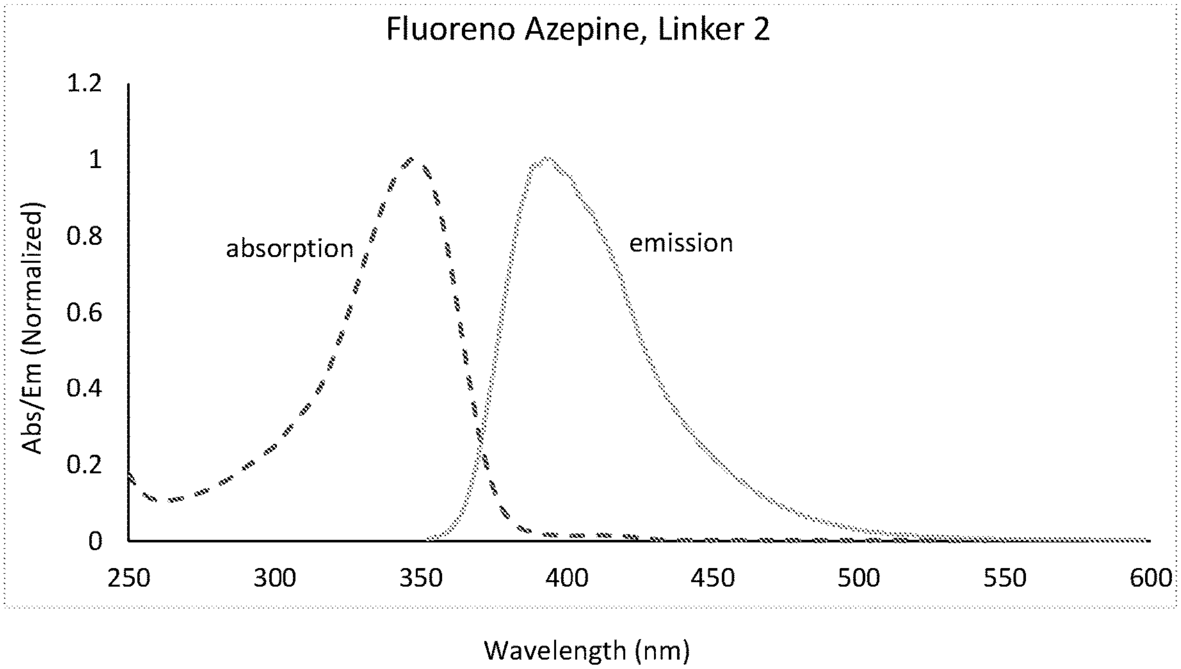
FIG. 8A-8B. Optical properties of the fluoreno azepine foundation polymer, with phenyl-based linker attachment.
Figure 8B:
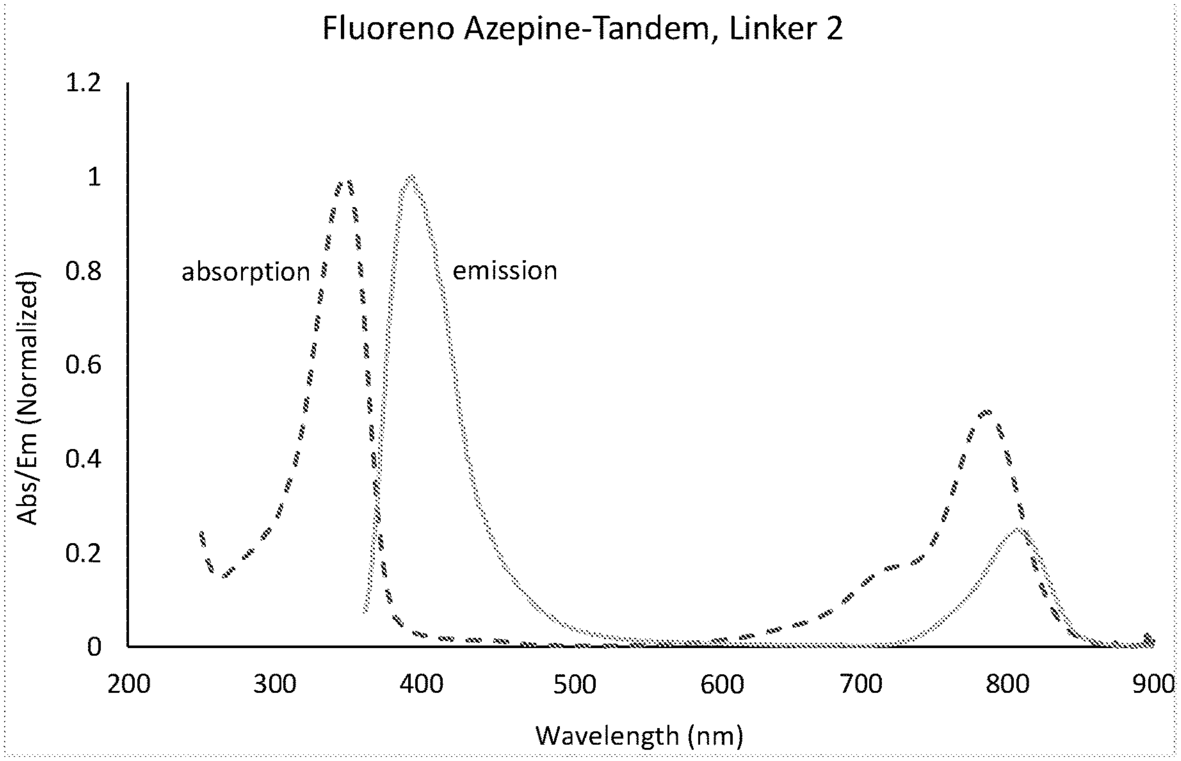
Figure 9A:
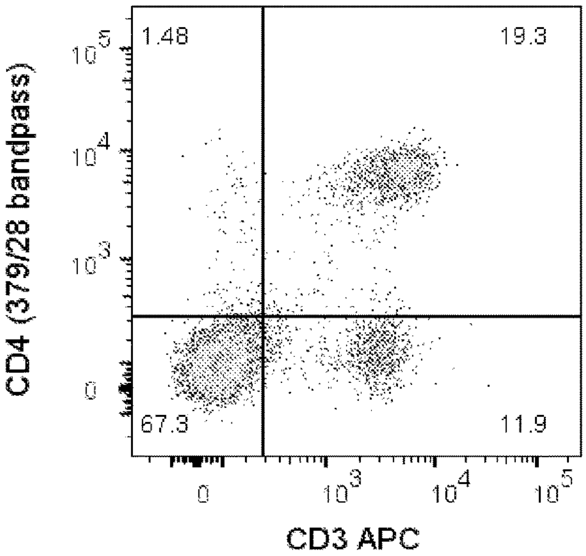
FIGS. 9A-9D. Performance of fluoreno oxepine-based polymer-conjugated antibodies in flow cytometric analysis.
Figure 9B:
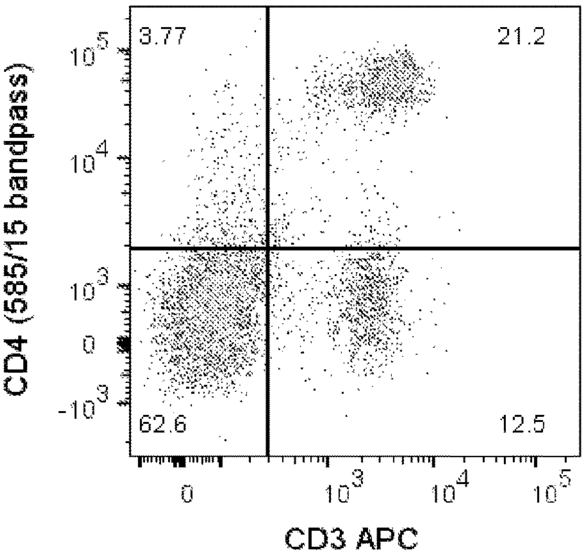
Figure 9C:
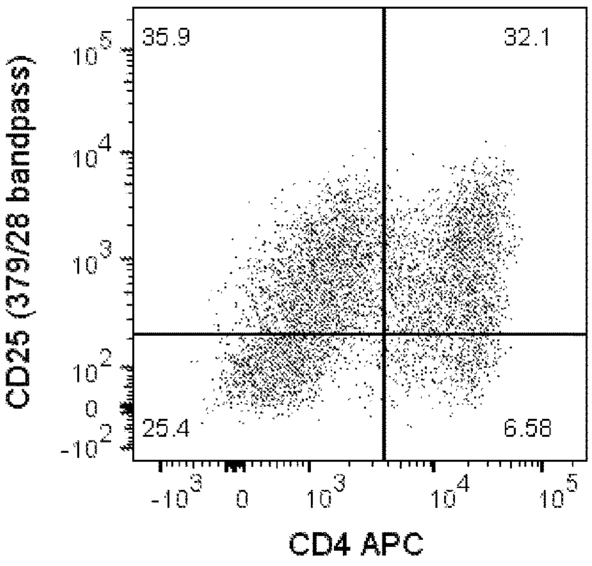
Figure 9D:
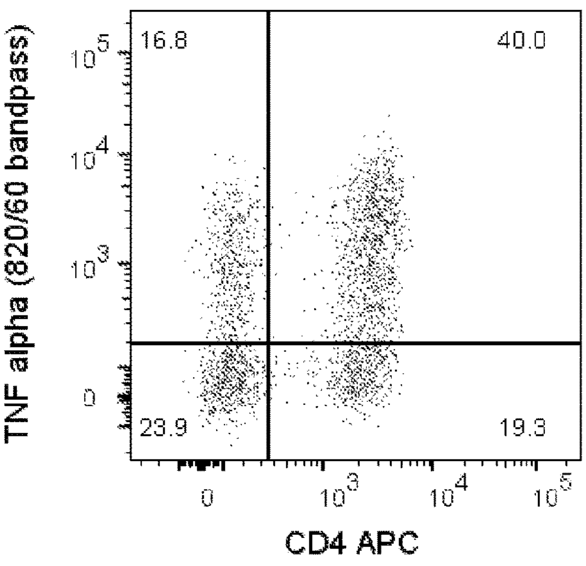
Figure 10A:
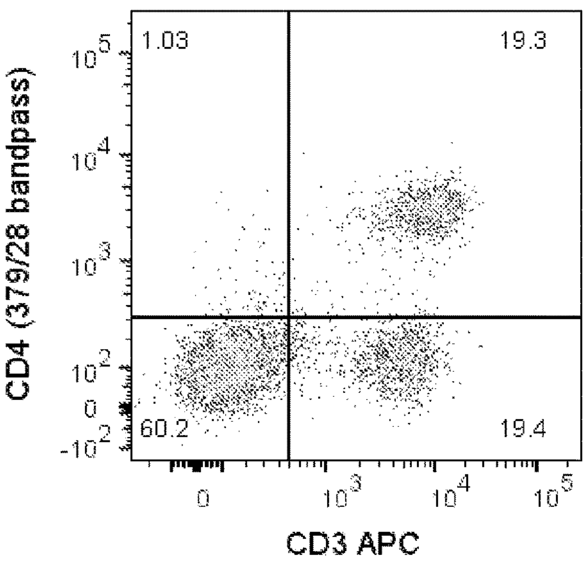
FIGS. 10A-10D. Performance of fluorenocycloheptane-based polymer-conjugated antibodies in flow cytometric analysis.
Figure 10B:
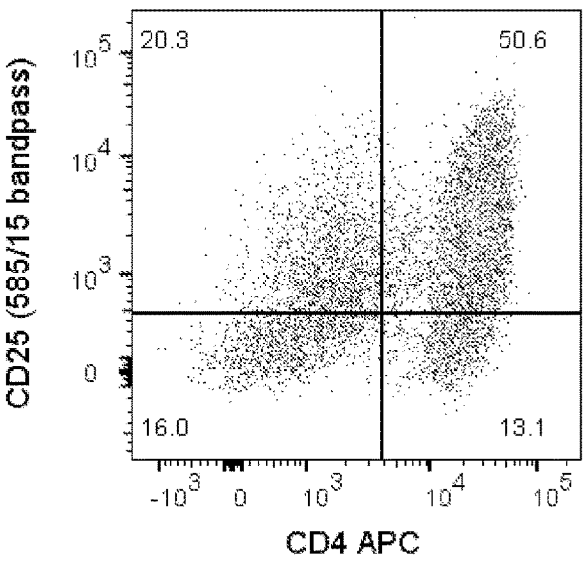
Figure 10C:
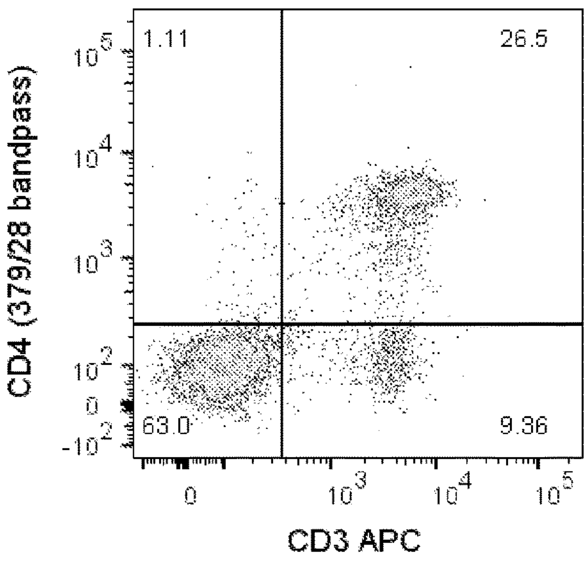
Figure 10D:
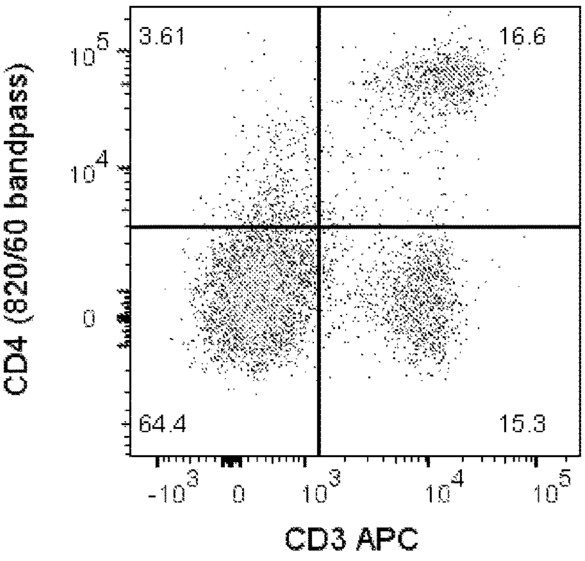
Figure 11A:
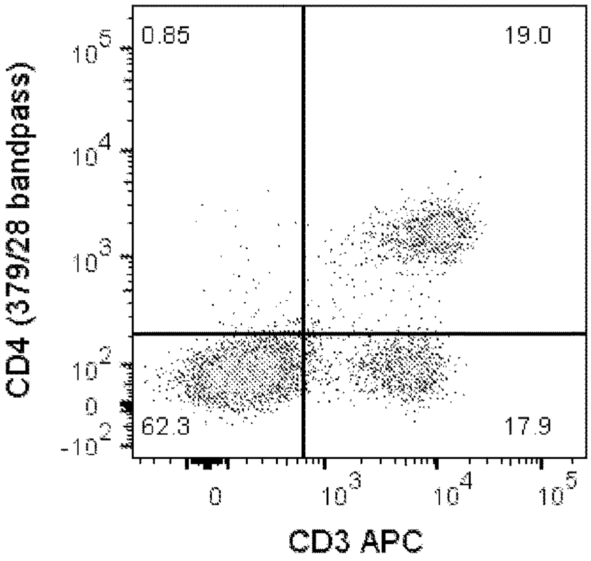
FIGS. 11A-11D. Performance of fluoreno azepine-based polymer-conjugated antibodies in flow cytometric analysis.
Figure 11B:
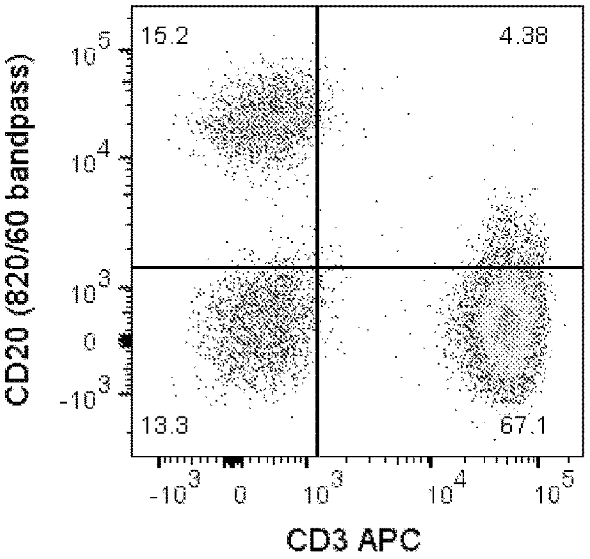
Figure 11C:
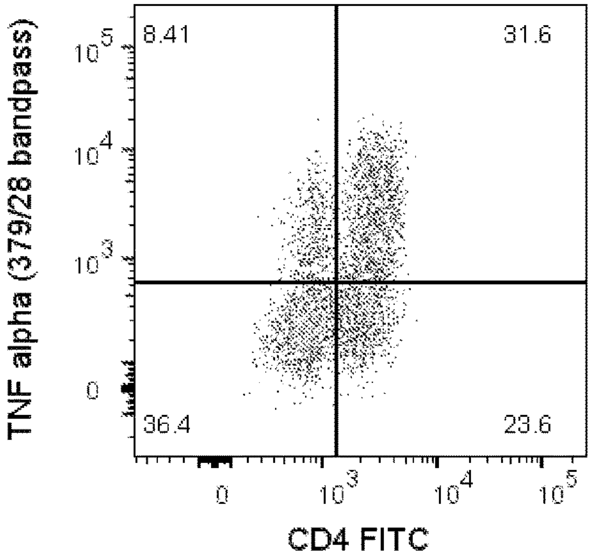
Figure 11D:
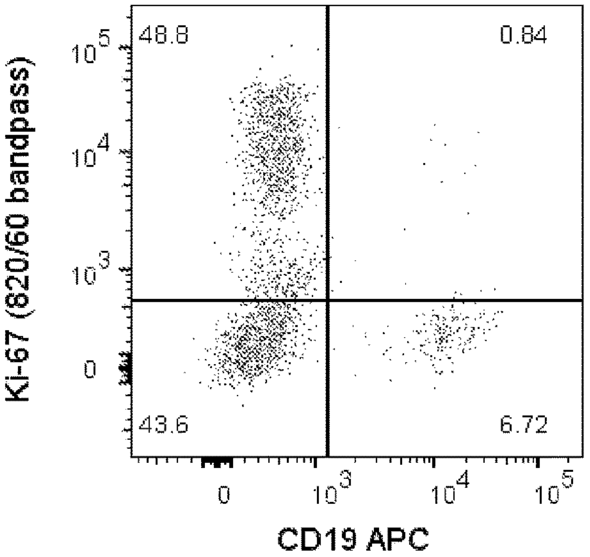

The antibody-polymer conjugate was purified from the free antibody over a Superdex 200 Increase Size Exclusion Chromatography column (24 mL) using a Bio-Rad NGC FPLC chromatography system. The conjugate was first spun at 20,238 rcf for 5 minutes to pellet any precipitated or cross-linked conjugate. The supernatant was then injected onto a 24 mL Superdex 200 Increase 10/300 GL column (GE Lifesciences) at <1.5% v/v and eluted at 1.0 mL/min with 10 mM Phosphate Buffer, pH 7.4. The first elution peak at 280 nm is collected, which contains the antibody-polymer conjugate and any free polymer and any subsequent peaks are discarded. (See FIG. 2) The optical properties of the linker attached polymers are shown in FIGS. 3-8.

Example 24. Cell Stimulations

Detection of some antigens require the stimulation of cells to upregulate expression. For CD25, normal human peripheral blood cells were cultured in RPMI-1640 containing 10% fetal bovine serum, 1:100 penicillin/streptomycin, 1:100 sodium pyruvate, and 1:1000 2-mercaptoethanol (cRPMI), and phytohemagluttinin was added at a 1:500 dilution for 3 days. For TNF alpha, normal human peripheral blood cells were cultured in cRPMI with a 1:500 dilution of a mixture containing phorbol myristate acetate, ionomycin, brefeldin A, and monensin for 4-6 hours. For Ki-67, normal human peripheral blood cells were cultured in cRPMI with plate-bound anti-human CD3 and soluble anti-human CD28 monoclonal antibodies for 3 days. After the indicated duration of stimulation, cells were harvested and washed in flow cytometry staining buffer before proceeding with antibody staining.

Example 25. Surface Staining for Mouse CD4 (Clone RM4-5), Human CD20 (Clone 2H7), and Human CD25 (Clone BC96)

For staining antigens found on the cell surface, single cell suspensions of mouse splenocytes or normal human peripheral blood cells were resuspended at 107 cells per mL in phosphate buffered saline containing 3% fetal calf serum and 0.09% sodium azide (flow cytometry staining buffer). One hundred microliters of the cell suspensions were aliquoted into 12×75 mm tubes and allophycocyanin (APC)-conjugated antibodies were added at optimal concentrations as recommended by the manufacturer. Polymer-conjugated antibodies were added to the cells at final concentrations from 0.0006-0.01 mg/mL. The mixture of cells and antibodies were incubated for 30 minutes at 4° C. and then 3 mL of flow cytometry staining buffer was added to the cells. The cells were centrifuged for 5 minutes at 600×g and the supernatant discarded. Cell pellets were resuspended in up to 0.4 mL of flow cytometry staining buffer, and then cells were analyzed on a LSRFortessa® SORP flow cytometer (Becton, Dickinson and Company) equipped with UV (355 nm) and red (640 nm) laser lines and bandpass filters appropriate for detection of APC (670/14), and the foundation and tandem polymer dyes (379/28, and 585/15 and 820/60, respectively). A minimum of 10,000 lymphocytes were collected. Data were analyzed using FlowJo software (Becton, Dickinson and Company).

Example 26. Intracellular Staining for Human TNF Alpha (Clone MAb11)

For intracellular staining and detection of TNF alpha, single cell suspensions of stimulated normal human peripheral blood cells were resuspended at 107 cells per mL in flow cytometry staining buffer. One hundred microliters of the cell suspensions were aliquoted into 12×75 mm tubes and 0.1 mL of a formaldehyde-based fixation buffer was added. Cells were incubated for 20-30 minutes at room temperature and then 3 mL of a detergent-based permeabilization buffer was added and the cells were centrifuged for 5 minutes at 600 xg and the supernatant discarded. An additional wash with 3 mL of permeabilization buffer was performed. Cells were resuspended in 0.1 mL of permeabilization buffer and then APC- or fluorescein isothiocyanate (FITC)-conjugated antibodies were added at optimal concentrations as recommended by the manufacturer, polymer-conjugated antibodies were added to the cells at final concentrations from 0.0006-0.01 mg/mL, and then the samples were incubated for 30 minutes at room temperature. Samples were washed two times with 3 mL of permeabilization buffer. After the last wash, cell pellets were resuspended in up to 0.4 mL of flow cytometry staining buffer, and then the samples were analyzed on a LSRFortessa® SORP flow cytometer (Becton, Dickinson and Company) equipped with UV (355 nm), red (640 nm), and blue (488 nm) laser lines and bandpass filters appropriate for detection of APC (670/14), FITC (530/30) and the foundation and tandem polymer dyes (379/28 and 820/60, respectively). A minimum of 10,000 lymphocytes were collected. Data were analyzed using FlowJo software (Becton, Dickinson and Company).

Example 27. Intracellular Staining for Human Ki-67 (clone 20Raj1)

For intracellular staining and detection of Ki-67, single cell suspensions of stimulated normal human peripheral blood cells were resuspended at 107 cells per mL in flow cytometry staining buffer. One hundred microliters of the cell suspensions were aliquoted into 12×75 mm tubes and 1 mL of a formaldehyde- and detergent-based fixation/permeabilization buffer was added. Cells were incubated for 20-30 minutes at room temperature and then 3 mL of a detergent-based permeabilization buffer was added and the cells were centrifuged for 5 minutes at 600 xg and the supernatant discarded. An additional wash with 3 mL of permeabilization buffer was performed. Cells were resuspended in 0.1 mL of permeabilization buffer and then APC-conjugated antibodies were added at optimal concentrations as recommended by the manufacturer, polymer-conjugated antibodies were added to the cells at final concentrations from 0.0006-0.01 mg/mL, and then the samples were incubated for 30 minutes at room temperature. Samples were washed two times with 3 mL of permeabilization buffer. After the last wash, cell pellets were resuspended in up to 0.4 mL of flow cytometry staining buffer, and then the samples were analyzed on a LSRFortessa® SORP flow cytometer (Becton, Dickinson and Company) equipped with UV (355 nm) and red (640 nm) laser lines and bandpass filters appropriate for detection of APC (670/14) and the tandem polymer dye (820/60). A minimum of 10,000 lymphocytes were collected. Data were analyzed using FlowJo software (Becton, Dickinson and Company).

The performances of fluoreno oxepine-, fluoreno azepine and fluorenocycloheptane-based polymer-conjugated antibodies in flow cytometric analysis are shown in FIGS. 9-11.

TABLE 4

Representative fluorene based polymers

| Monomer base | Bridging atom | Linker* | Polymers** |
|---|---|---|---|
| Fluoreno oxepine | Oxygen | Linker 1 | OPT-2 |
| Fluoreno oxepine | Oxygen | Linker 2 | OPT-3 |
| Fluorenocycloheptane | Carbon | Linker 1 | OPT-4 |
| Fluorenocycloheptane | Carbon | Linker 2 | OPT-6 |
| Fluoreno azepine | Nitrogen | Linker 1 | OPT-5 |
| Fluoreno azepine | Nitrogen | Linker 2 | OPT-5.1 |

*Linker 1 is methylene, linker 2 is PEG4.

**The structures of the polymers in the above table are as follows:

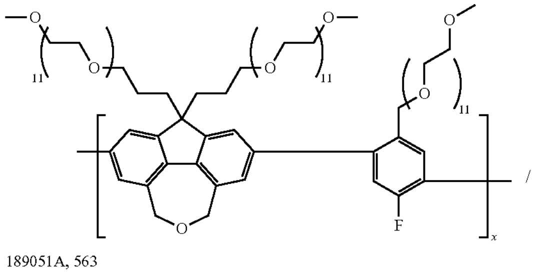

189051A, 563

TABLE 4-continued
Representative fluorene based polymers
| Monomer base | Bridging atom | Linker* | Polymers** |
|---|---|---|---|
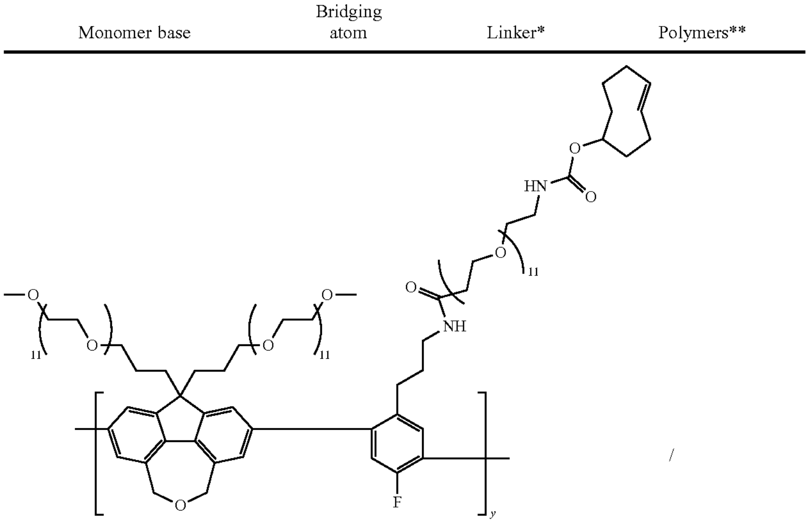
/
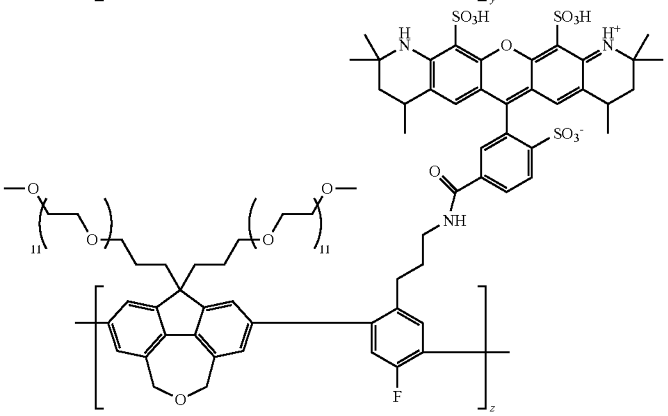
OPT-2
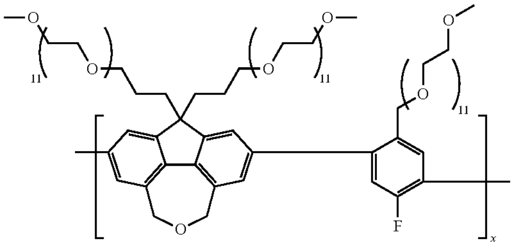
/
180628R1E, 805
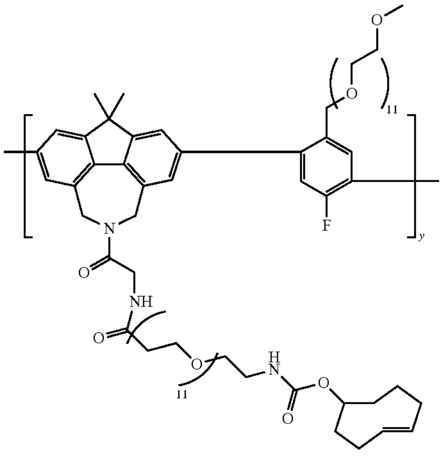
/

TABLE 4-continued
| Representative fluorene based polymers | | | |
|---|---|---|---|
| Monomer base | Bridging atom | Linker* | Polymers** |
| 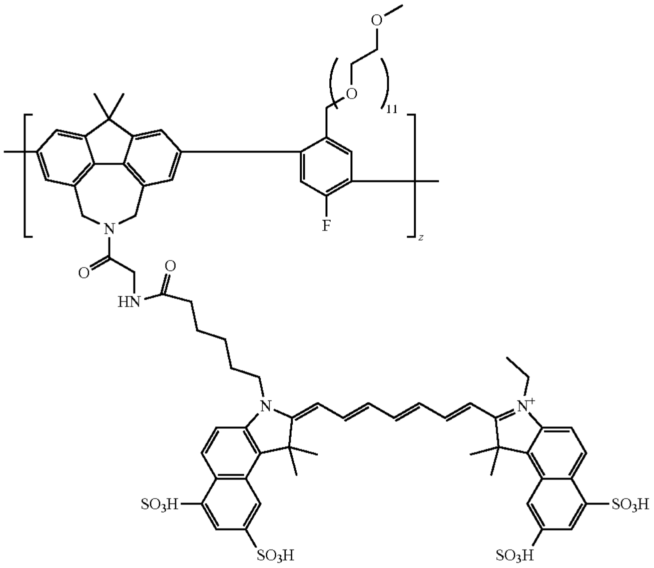 | | | OPT-3 |
| 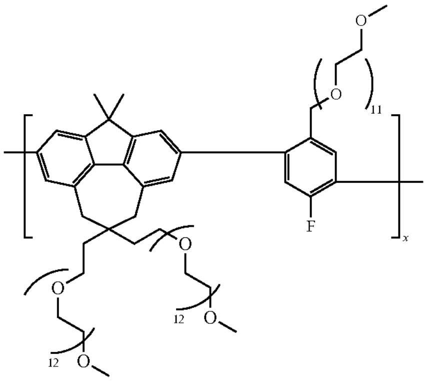 / | | | |
| 180725R1A | | | |
| 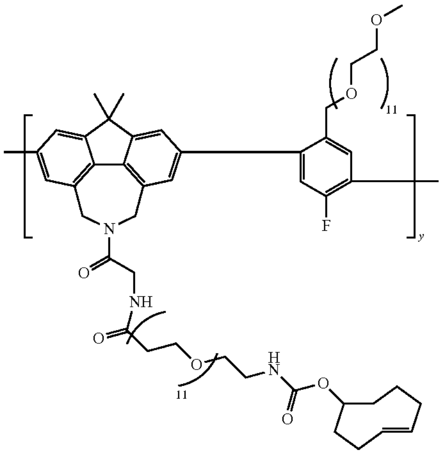 / | | | |

TABLE 4-continued
| Representative fluorene based polymers | | | |
|---|---|---|---|
| Monomer base | Bridging atom | Linker* | Polymers** |
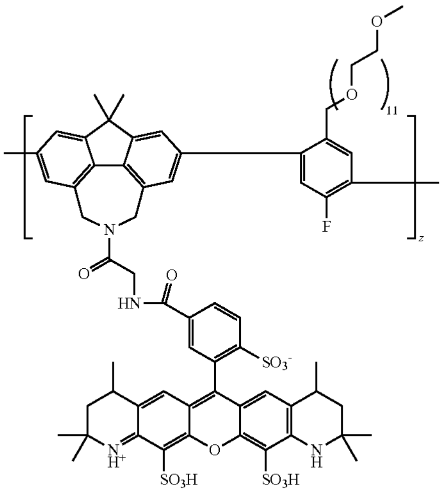
OPT-4
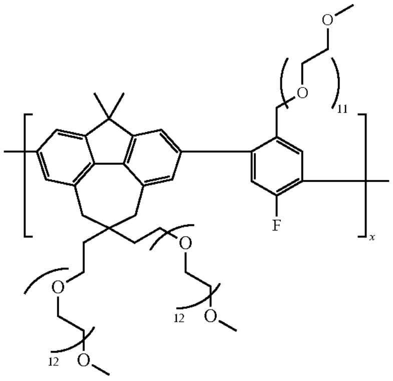
/
HG180802R1H, 805
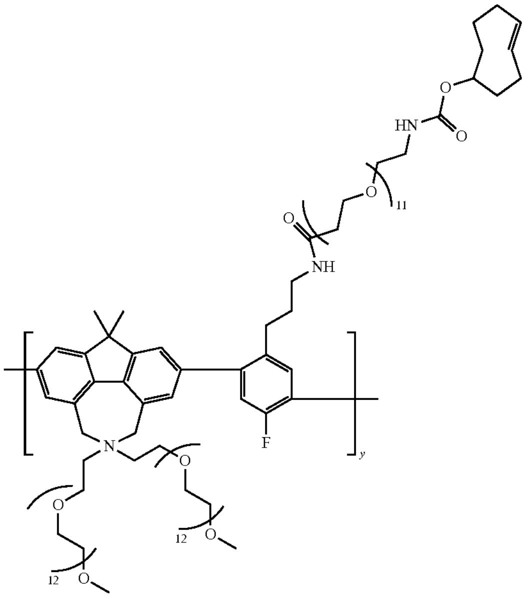
/

TABLE 4-continued
| Representative fluorene based polymers | | | |
|---|---|---|---|
| Monomer base | Bridging atom | Linker* | Polymers** |
| 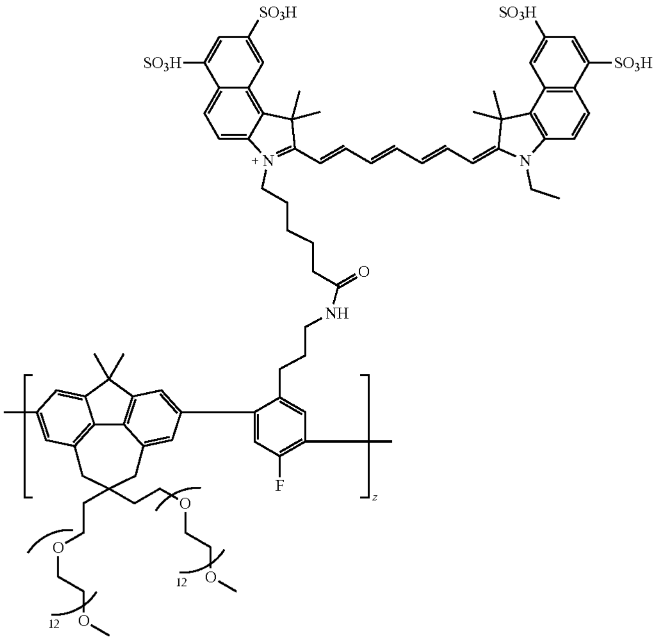 | | | OPT-6 |
| 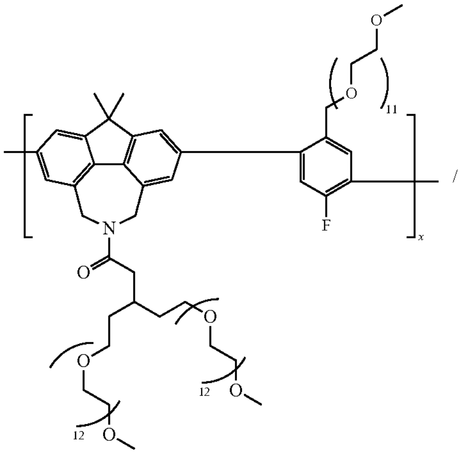<br>1800712R1B, 805<br>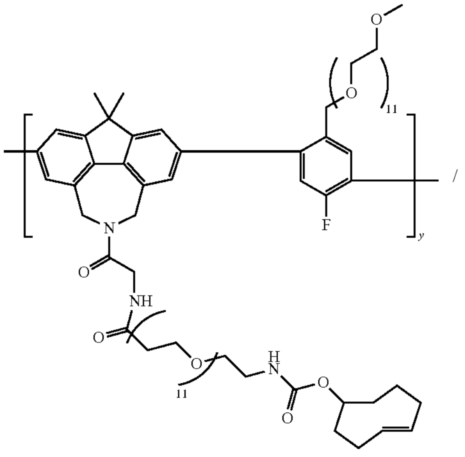 | | | |

TABLE 4-continued
| Representative fluorene based polymers | | | |
|---|---|---|---|
| Monomer base | Bridging atom | Linker* | Polymers** |
| 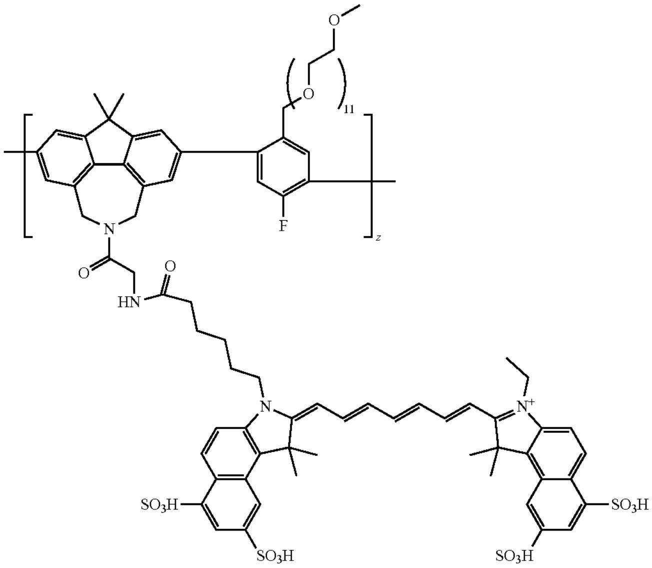 | | | OPT-5 |
| 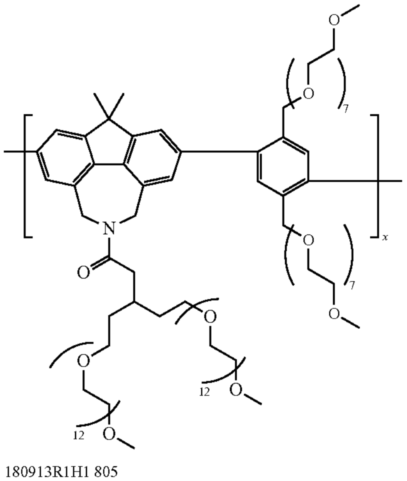 / | | | |
180913R1H1 805

TABLE 4-continued
| Representative fluorene based polymers | | | |
|---|---|---|---|
| Monomer base | Bridging atom | Linker* | Polymers** |
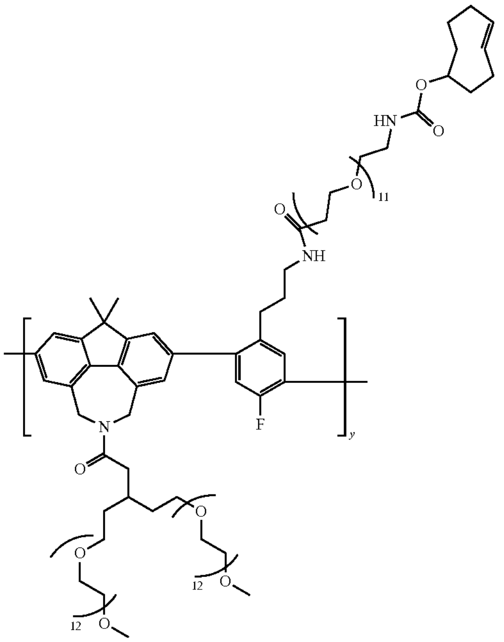
/
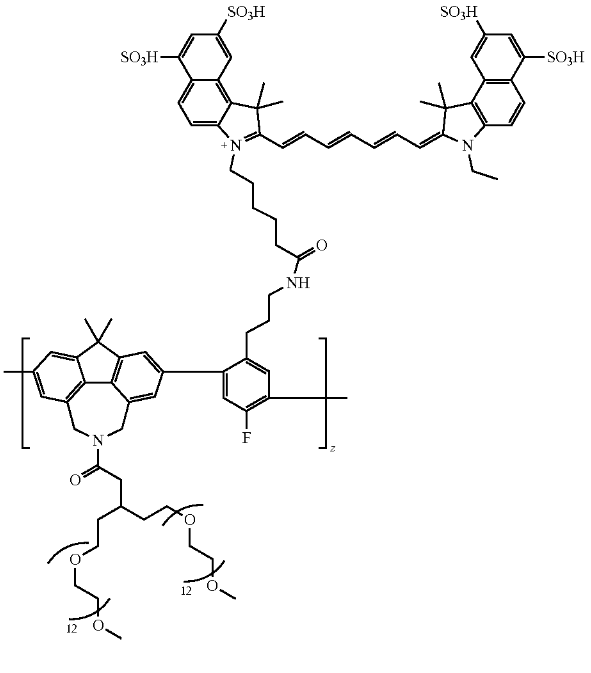
OPT-5.1

What is claimed is:

1. A polymer comprising monomer units of formula A

A

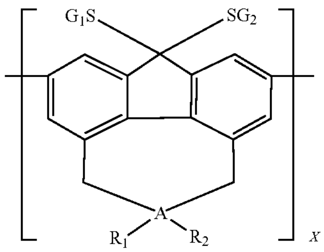

wherein X is the number of monomer units of formula A in the polymer wherein the monomer units of formula A are consecutive or nonconsecutive, and one or more monomer units of formula B

B

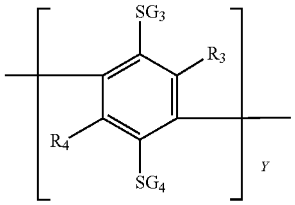

wherein Y is the number of monomer units of formula B in the polymer wherein the monomer units of formula B are consecutive or nonconsecutive, and, optionally one or more monomer units of formula C

C

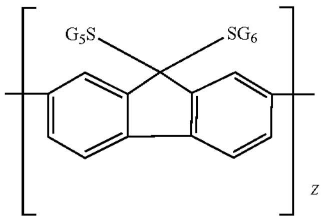

wherein Z is the number of monomer units of formula C in the polymer wherein the monomer units of formula C are consecutive or nonconsecutive, wherein A is N;

wherein $SG_1$, $SG_2$, $SG_5$, $SG_6$, each independently is a hydrogen, an alkyl, an amino, a sulfo, a polyethylene glycol (PEG), a water solubilizing group, an acceptor, a linker (L), and/or a biological substrate conjugated via a linker (L-BS);

wherein $R_1$ is non-existent or a hydrogen, an alkyl, an amino, a sulfo, a polyethylene glycol (PEG), a water solubilizing group, an acceptor, a linker (L), and/or a biological substrate conjugated via a linker (L-BS);

wherein $R_2$ is a hydrogen, an alkyl, an amino, a sulfo, a polyethylene glycol (PEG), a water solubilizing group, an acceptor, a linker (L), and/or a biological substrate conjugated via a linker (L-BS);

wherein $SG_3$, $SG_4$, $R_3$ and $R_4$ each independently is a hydrogen, a halogen, an amino, a PEG, a linker (L), an acceptor, or a biological substrate conjugated via a linker (L-BS);

wherein the acceptor is a fluorophore or a fluorescent dye;

wherein each polymer end independently is a hydrogen, an alkyl, a halogen, a boronyl, an aryl, a heteroaryl group or a L-BS; and wherein X, Y and Z are integers such that X+Y+Z is from 15 to 50, X is at least 10, and a ratio of X to Y+Z is 0.3-1.0.

2. The polymer of claim 1, wherein the excitation peak of the polymer is close to 350 nm.

3. The polymer of claim 1, wherein the monomer units of formulas A and B, and also of formula C, if formula C is present, are directly connected to one another.

4. The polymer of claim 1, wherein a ratio of the acceptor to polymer is 0.01-0.2.

5. The polymer of claim 1, wherein the linker is an alkyl or a PEG, optionally further comprising a carboxamide, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamide, a sulfonate ester, a 1,2,3-triazole, a pyradazine, a thiazolidine, a 2-diphenylphosphonyl-benzoamide, an isoxazole, a succinimide group, or a combination thereof.

6. The polymer according to claim 1, wherein:

(i) $SG_1$, $SG_2$, $SG_5$ and $SG_6$ independently represent a PEG, an alkyl, a carboxyalkyl, a sulfonylalkyl, a phosphonylalkyl, an aminoalkyl or L-BS; and/or (ii) $SG_3$, $SG_4$, $R_3$ and $R_4$ independently represent a hydrogen, a halogen, a PEG, or a linker (L), and/or (iii) L is an alkyl chain or a PEG chain; and/or (iv) BS is an antibody, a peptide, a protein, an oligonucleotide, a nucleic acid or a carbohydrate; and/or (v) X, Y and Z are selected to provide a ratio of X to Y+Z is >0.4.

7. The polymer according to claim 1, wherein $SG_1$, $SG_2$, $SG_5$ and $SG_6$ are independently PEG3 to PEG30.

8. The polymer according to claim 1, wherein: $SG_1$-$SG_6$ and $R_1$-$R_4$ independently represent a hydrogen, a carboxyaryl, or a L-BS.

9. The polymer of claim 1, wherein $SG_3$, $SG_4$, $R_3$ and $R_4$ each independently is an alkyl, fluoro, hydrogen, a polyethylene glycol (PEG), or an acceptor.

10. The polymer of claim 1, wherein the acceptor is a fluorescein, a rhodamine, a rhodol, a cyanine, a BODIPY, a squaraine, a coumarin, a perylenediimide, a diketopyrrolopyrrole, a porphyrin or a phthalocyanine.

11. The polymer of claim 1, wherein formula A comprises:

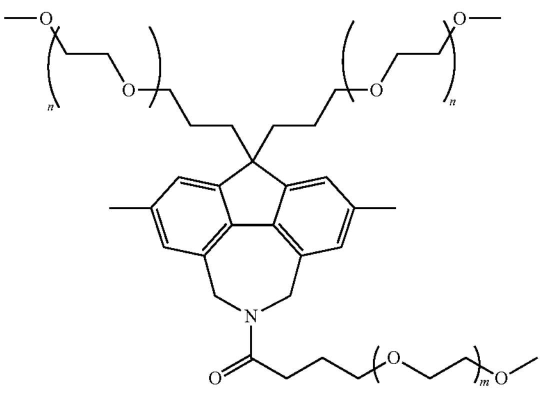

or

-continued
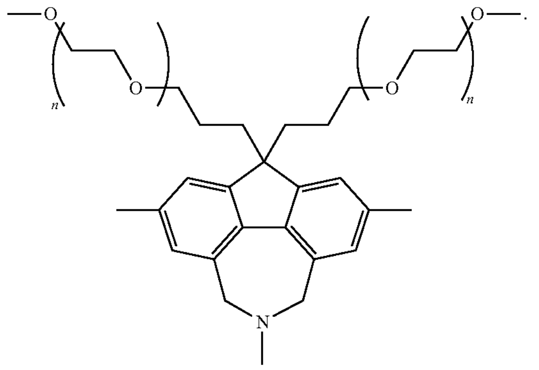
12. The polymer of claim 1, wherein formula B is
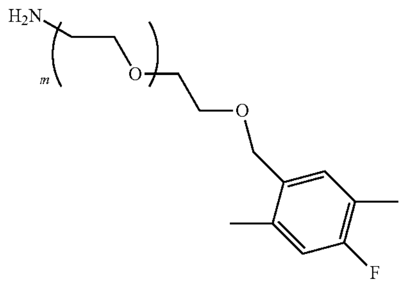
,
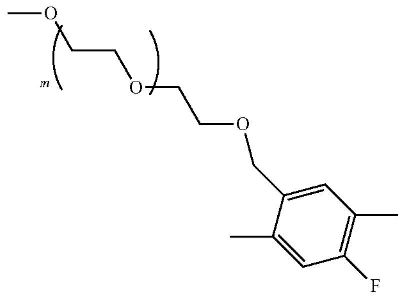
,
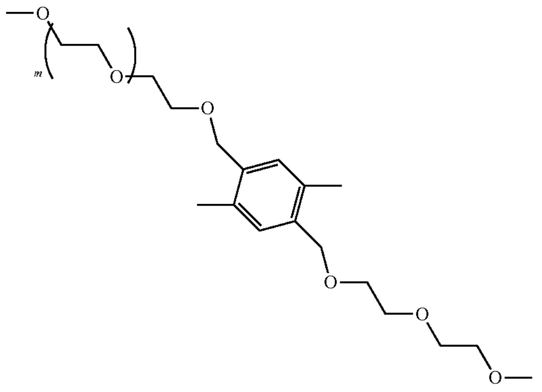
, or
-continued
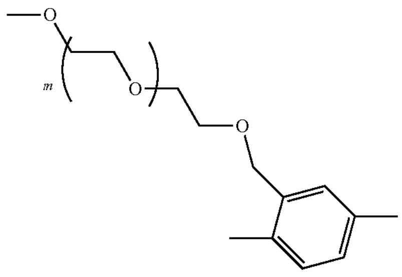
wherein m is from 5 to 20.
13. The polymer of claim 1, wherein the acceptor comprises:
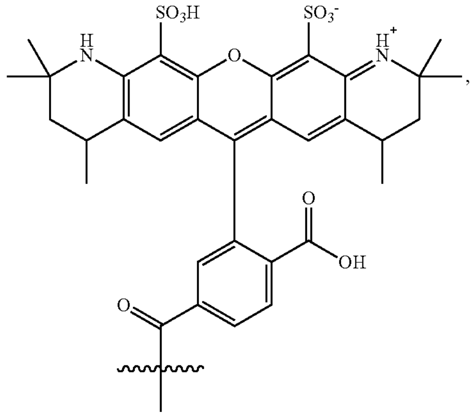
,
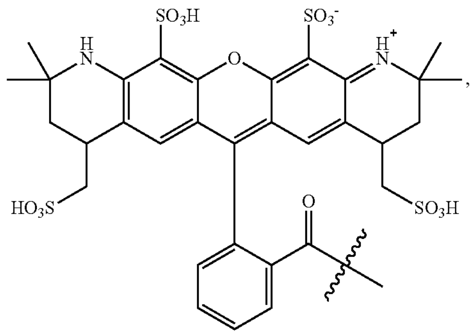
,
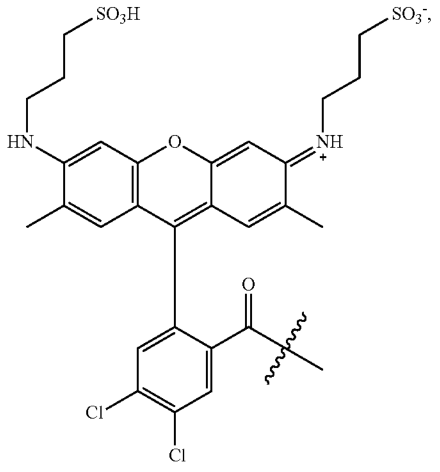

-continued

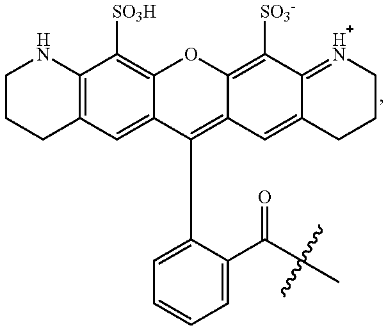

,

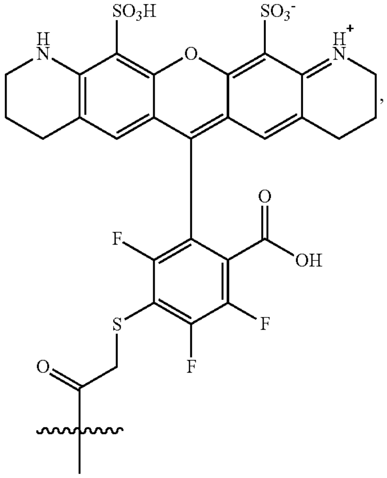

,

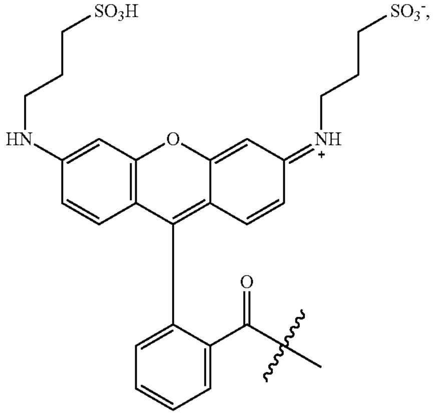

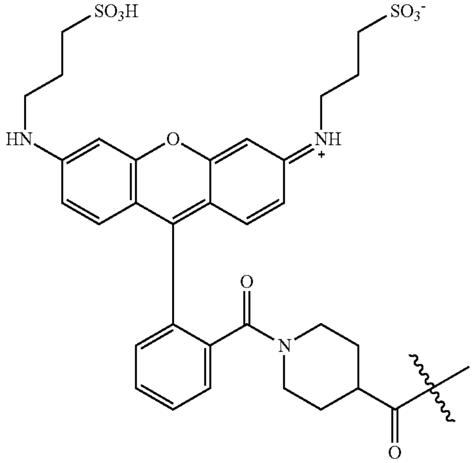

,

-continued

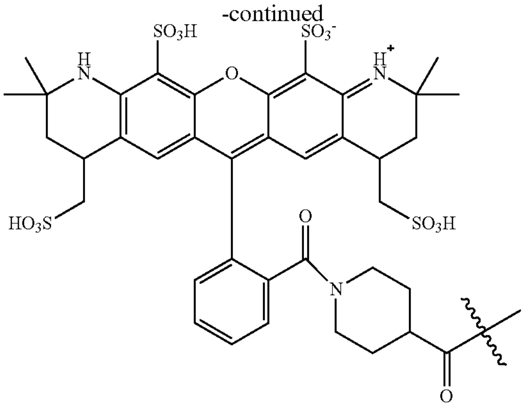

,

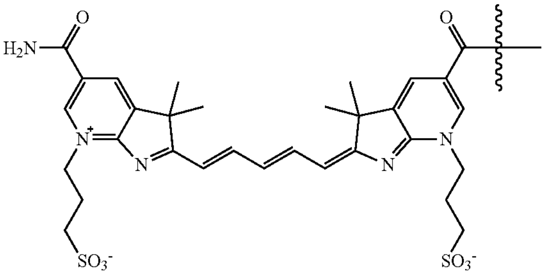

,

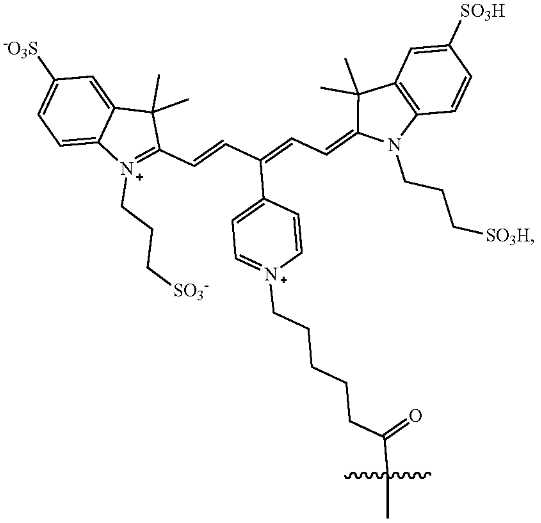

or

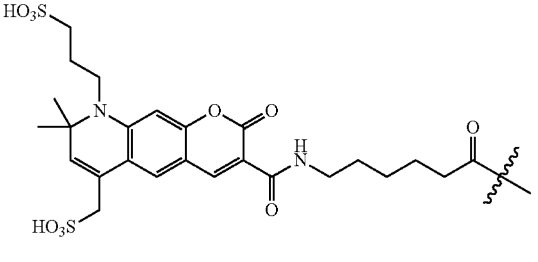

.

14. A polymer-antibody conjugate, comprising one or more polymers according to claim 1 and an antibody, wherein the one or more polymers are conjugated to the antibody.

15. A method of detecting an analyte in a sample, comprising a) combining said sample with a detection reagent comprising a polymer under conditions under which said detection reagent will bind said analyte; and b) detecting the detection reagent bound analyte by fluorescence, wherein the polymer is optionally bound to an antibody, wherein the polymer comprises monomer units of formula A

A

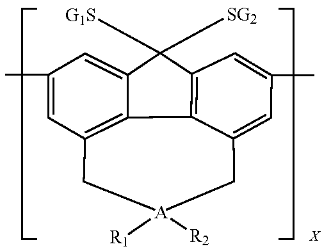

wherein X is the number of monomer units of formula A in the polymer wherein the monomer units of formula A are consecutive or nonconsecutive, and one or more monomer units of formula B

B

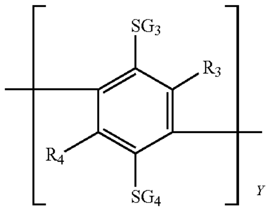

wherein Y is the number of monomer units of formula B in the polymer wherein the monomer units of formula B are consecutive or nonconsecutive, and, optionally one or more monomer units of formula C

C

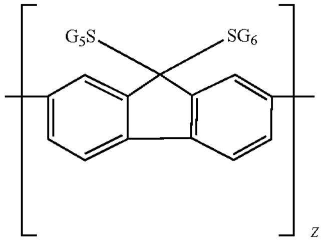

wherein Z is the number of monomer units of formula C in the polymer wherein the monomer units of formula C are consecutive or nonconsecutive, wherein A is N;

wherein $SG_1$, $SG_2$, $SG_5$, $SG_6$, each independently is a hydrogen, an alkyl, an amino, a sulfo, a polyethylene glycol (PEG), a water solubilizing group, an acceptor, a linker (L), and/or a biological substrate conjugated via a linker (L-BS);

wherein $R_1$ is non-existent or a hydrogen, an alkyl, an amino, a sulfo, a polyethylene glycol (PEG), a water solubilizing group, an acceptor, a linker (L), and/or a biological substrate conjugated via a linker (L-BS);

wherein $R_2$ is a hydrogen, an alkyl, an amino, a sulfo, a polyethylene glycol (PEG), a water solubilizing group, an acceptor, a linker (L), and/or a biological substrate conjugated via a linker (L-BS);

wherein $SG_3$, $SG_4$, $R_3$ and $R_4$ each independently is a hydrogen, a halogen, an amino, a PEG, a linker (L), an acceptor, or a biological substrate conjugated via a linker (L-BS);

wherein the acceptor is a fluorophore or a fluorescent dye;

wherein each polymer end independently is a hydrogen, an alkyl, a halogen, a boronyl, an aryl, a heteroaryl group or a L-BS; and wherein X, Y and Z are integers such that X+Y+Z is from 15 to 50, X is at least 10, and a ratio of X to Y+Z is 0.3-1.0.

16. A system for detecting an analyte in a sample, comprising a detection reagent comprising a polymer-antibody conjugate according to claim 14, one or more cells, and an optical response device.

17. A kit comprising a polymer comprising a conjugated biological substrate selected from the group consisting of a specific binding pair member, a nucleoside, a nucleotide, an oligonucleotide, a nucleic acid polymer, a peptide, and a protein to result in a labeled biological substrate, and one or more buffering agents, wherein the polymer comprises monomer units of formula A

A

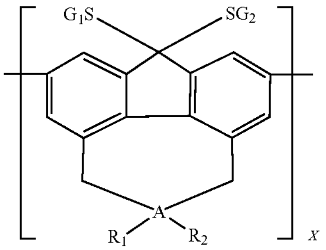

wherein X is the number of monomer units of formula A in the polymer wherein the monomer units of formula A are consecutive or nonconsecutive, and one or more monomer units of formula B

B

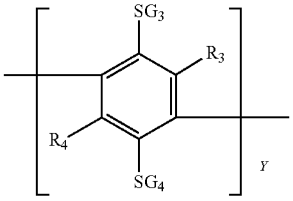

wherein Y is the number of monomer units of formula B in the polymer wherein the monomer units of formula B are consecutive or nonconsecutive, and, optionally one or more monomer units of formula C

C

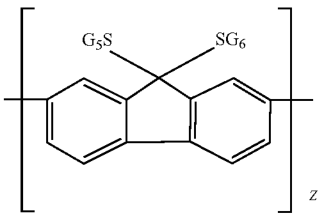

wherein Z is the number of monomer units of formula C in the polymer wherein the monomer units of formula C are consecutive or nonconsecutive, wherein A is N;

wherein $SG_1$, $SG_2$, $SG_5$, $SG_6$, each independently is a hydrogen, an alkyl, an amino, a sulfo, a polyethylene glycol (PEG), a water solubilizing group, an acceptor, a linker (L), and/or a biological substrate conjugated via a linker (L-BS);

wherein $R_1$ is non-existent or a hydrogen, an alkyl, an amino, a sulfo, a polyethylene glycol (PEG), a water solubilizing group, an acceptor, a linker (L), and/or a biological substrate conjugated via a linker (L-BS);

wherein $R_2$ is a hydrogen, an alkyl, an amino, a sulfo, a polyethylene glycol (PEG), a water solubilizing group, an acceptor, a linker (L), and/or a biological substrate conjugated via a linker (L-BS);

wherein $SG_3$, $SG_4$, $R_3$ and $R_4$ each independently is a hydrogen, a halogen, an amino, a PEG, a linker (L), an acceptor, or a biological substrate conjugated via a linker (L-BS);

wherein the acceptor is a fluorophore or a fluorescent dye;

wherein each polymer end independently is a hydrogen, an alkyl, a halogen, a boronyl, an aryl, a heteroaryl group or a L-BS; and wherein X, Y and Z are integers such that X+Y+Z is from 15 to 50, X is at least 10, and a ratio of X to Y+Z is 0.3-1.0.

18. A polymer comprising monomer units of formula A

A

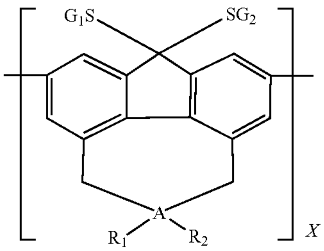

wherein X is the number of monomer units of formula A in the polymer wherein the monomer units of formula A are consecutive or nonconsecutive, and one or more monomer units of formula B

B

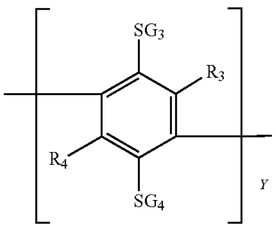

wherein Y is the number of monomer units of formula B in the polymer wherein the monomer units of formula B are consecutive or nonconsecutive, and, optionally one or more monomer units of formula C

C

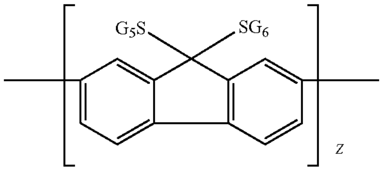

wherein Z is the number of monomer units of formula C in the polymer wherein the monomer units of formula C are consecutive or nonconsecutive, wherein A is N;

wherein $SG_1$, $SG_2$, $SG_5$, $SG_6$, each independently is a hydrogen, an alkyl, an amino, a sulfo, a polyethylene glycol (PEG), a water solubilizing group, a fluorophore or fluorescent dye, a linker (L), and/or a biological substrate conjugated via a linker (L-BS);

wherein $R_1$ is non-existent;

wherein $R_2$ is

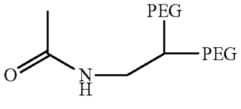

or

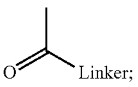

wherein $SG_3$, $SG_4$, $R_3$ and $R_4$ each independently is a hydrogen, a halogen, an amino, a PEG, a linker (L), an acceptor, or a biological substrate conjugated via a linker (L-BS);

wherein the acceptor is a fluorophore or a fluorescent dye;

wherein each polymer end independently is a hydrogen, an alkyl, a halogen, a boronyl, an aryl, a heteroaryl group or a L-BS; and wherein X, Y and Z are integers such that X+Y+Z is from 15 to 50, X is at least 10, and a ratio of X to Y+Z is 0.3-1.0.

19. The polymer of claim 18, wherein the linker is an alkyl or a PEG, optionally further comprising a carboxamide, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamide, a sulfonate ester, a 1,2,3-triazole, a pyradazine, a thiazolidine, a 2-diphenylphosphonyl-benzoamide, an isoxazole, a succinimide group, or a combination thereof.

* * * * *